(12) United States Patent
Horton et al.

(10) Patent No.: US 8,945,235 B2
(45) Date of Patent: Feb. 3, 2015

(54) REMOVABLE DEPLOYMENT DEVICE, SYSTEM, AND METHOD FOR IMPLANTABLE PROSTHESES

(71) Applicant: Atrium Medical Corporation, Hudson, NH (US)

(72) Inventors: Anthony R. Horton, Manchester, NH (US); David Filipiak, Nashua, NH (US); Albert A. LePage, Jr., Nashua, NH (US)

(73) Assignee: Atrium Medical Corporation, Hudson, NH (US)

( * ) Notice: Subject to any disclaimer, the term of this patent is extended or adjusted under 35 U.S.C. 154(b) by 0 days.

(21) Appl. No.: 13/829,987

(22) Filed: Mar. 14, 2013

(65) Prior Publication Data
US 2014/0025093 A1    Jan. 23, 2014

Related U.S. Application Data

(60) Provisional application No. 61/616,150, filed on Mar. 27, 2012.

(51) Int. Cl.
  *A61F 2/02*    (2006.01)
  *A61B 17/08*   (2006.01)
  *A61F 2/00*    (2006.01)

(52) U.S. Cl.
  CPC ............ *A61F 2/0063* (2013.01); *A61F 2/02* (2013.01)
  USPC ...................................... 623/23.72; 606/151

(58) Field of Classification Search
  CPC .............................. A61F 2/0063; A61F 2/02
  USPC ................... 606/151, 213; 623/11.11, 23.72; 600/29, 30, 37
  See application file for complete search history.

(56) References Cited

U.S. PATENT DOCUMENTS

| 5,366,460 | A | 11/1994 | Eberbach |
| 5,370,650 | A | 12/1994 | Tovey et al. |
| 6,551,356 | B2 | 4/2003 | Rousseau |

(Continued)

FOREIGN PATENT DOCUMENTS

| WO | WO 2011/043795 | 4/2011 |
| WO | WO 2011/128903 | 10/2011 |

OTHER PUBLICATIONS

International Search Report for International Application PCT/US2013/034121, dated Jun. 5, 2013.

(Continued)

*Primary Examiner* — Julian W Woo

(57) ABSTRACT

A prosthesis includes an enclosure. A flexible support structure is situated at least partially within the enclosure and is removable therefrom. The flexible support structure occupies a total circumferential area and has a stiffness that is sufficient to allow the prosthesis to assume a deployed (e.g., generally planar) configuration. A tab is adjoined with the flexible support structure and extends external to the enclosure. Pulling the tab directionally away from the prosthesis causes a reconfiguration of the flexible support structure sufficient to enable the flexible support structure to pass through an opening in the prosthesis having a total circumferential area that is less than the total circumferential area occupied by the flexible support structure when the prosthesis is in the deployed (e.g., generally planar) configuration, enabling removal of the flexible support structure from the enclosure.

23 Claims, 47 Drawing Sheets

(56) References Cited

U.S. PATENT DOCUMENTS

| | | |
|---|---|---|
| 6,575,988 B2 | 6/2003 | Rousseau |
| 6,669,735 B1 | 12/2003 | Pelissier |
| 6,814,743 B2 | 11/2004 | Chin et al. |
| 7,101,381 B2 | 9/2006 | Ford et al. |
| 7,544,203 B2 | 6/2009 | Chin et al. |
| 7,947,062 B2 | 5/2011 | Chin et al. |
| 2001/0016754 A1 | 8/2001 | Adams et al. |
| 2004/0019360 A1* | 1/2004 | Farnsworth et al. ........... 606/151 |
| 2004/0087980 A1* | 5/2004 | Ford et al. ..................... 606/151 |
| 2005/0043716 A1 | 2/2005 | Frimer |
| 2007/0299538 A1* | 12/2007 | Roeber ...................... 623/23.72 |
| 2008/0147200 A1 | 6/2008 | Rousseau et al. |
| 2008/0237287 A1* | 10/2008 | Mitchinson .................... 224/645 |
| 2009/0082792 A1* | 3/2009 | Koyfman et al. .............. 606/151 |
| 2009/0270999 A1 | 10/2009 | Brown |
| 2009/0326676 A1 | 12/2009 | Dupic et al. |
| 2011/0040311 A1 | 2/2011 | Levin et al. |
| 2011/0082479 A1 | 4/2011 | Friedlander et al. |
| 2011/0144667 A1* | 6/2011 | Horton et al. ................. 606/151 |
| 2011/0224704 A1* | 9/2011 | Bailly et al. .................. 606/151 |
| 2011/0295283 A1 | 12/2011 | Darois et al. |

OTHER PUBLICATIONS

International Search Report for International Application PCT/US2013/034107, dated Aug. 6, 2013.

* cited by examiner

REMOVABLE DEPLOYMENT DEVICE, SYSTEM, AND METHOD FOR IMPLANTABLE PROSTHESES

RELATED APPLICATION

This application claims priority to, and the benefit of, U.S. Provisional Application No. 61/616,150, filed Mar. 27, 2012, for all subject matter common to both applications. The disclosure of said provisional application is hereby incorporated by reference in its entirety.

FIELD OF THE INVENTION

The present invention relates to deployment devices, systems, and methods suitable for medical applications, such as open and laparoscopic ventral hernia repairs and small hernia repair (e.g., repair of umbilical or epigastric defects). More particularly, the present invention relates to a removable deployment device configured to fit within an enclosure of a prosthesis and serve as a surgical aid in the deployment, positioning, and fixation of the prosthesis.

BACKGROUND OF THE INVENTION

Prostheses often are implanted during surgical or other medical procedures to aid in repair of defects, reinforcement of a target site, delivery of therapeutic, or to serve other medical purposes. For example, hernia patches or other similar prostheses are commonly implanted using open or laparoscopic techniques. Such techniques can be useful in treating central hernias as well as small hernias, e.g., umbilical or epigastral defects.

For instance, open procedures are performed by making a single incision through which a hernia patch is inserted for implantation to the target site. Typically, the hernia patch is rolled up or otherwise compacted prior to insertion so as to enable greater ease of passage through the single incision and to the site of the defect. Once the hernia patch is appropriately positioned within the body (e.g., in the abdominal cavity, in the pre-peritoneal space, etc.), it can be unfolded, unrolled, un-collapsed, or otherwise caused to assume a deployed, generally planar configuration.

However, deploying the hernia patch in this manner is a cumbersome task that requires skillful manual manipulation. Even then, it is often difficult for an adept surgeon given that such a task is performed under several layers of tissue. Furthermore, manipulation of the hernia patch can prove to be an even greater challenge in the case of laparoscopic procedures, since trocars used to implant the hernia patch provide limited range of motion, thereby requiring the surgeon to utilize small instruments and graspers.

Several existing mesh patches provide a base layer of mesh with second or third layers that form pockets, aprons, or other enclosures intended to aid in the manipulation and fixation of the mesh. Furthermore, among these, some mesh patches include a rigidified perimeter and/or a rigid ring or frame attached near a perimeter of the patch to cause the patch to assume a deployed, generally planar configuration once inserted into a patient. In some instances, the ring or frame is constructed from biodegradable material that can be absorbed over time. These absorbable rings or frames tend to lack sufficient strength or can potentially interfere with the intended functionality of the patch, e.g., tissue in-growth or reinforcement. In other instances, the ring or frame is formed of non-absorbable material (e.g., polypropylene, PTFE, etc.) and thus remains a permanent structure within the body. These patches tend to exhibit greater strength, but consequently may interfere with the functionality of the patch. For example, permanent rings can form additional contours that can create points of tension at particularly undesirable positions on the surface of the patch. Still other attempts to facilitate deployment provide a monofilament or wire ring that is crimped or sintered in order to adjoin the ends, which create yet additional weak points that historically have been associated with higher risk of failure, health complications, and even death after implantation.

SUMMARY

There is a need for a deployment device capable of providing suitable structural reinforcement to deploy a patch or other prosthesis, without sacrificing performance of the patch or prosthesis due to prolonged or permanent occupancy in a body. There is also a need for a deployment device that results in less foreign material being permanently implanted in the patient. The present invention is directed toward further solutions to address this and other needs, in addition to having other desirable characteristics that will be appreciated by one of skill in the art upon reading the present specification.

In accordance with an example embodiment of the present invention, a deployment device includes a flexible support structure configured in generally planar form having a total circumferential area in a deployed configuration, and configured to independently apply a radial deployment force to achieve the deployed configuration. A separation line in the flexible support structure extends in a generally serpentine shape from a central portion of the flexible support structure to a perimeter of the flexible support structure. A through-cut is disposed at and an innermost end of the separation line at the central portion of the flexible support structure. A first strap is coupled with the flexible support structure in the central portion and proximal the through-cut. A second strap is coupled with the flexible support structure in the central portion and more distal from the through-cut than the first strap. A pulling force applied to the first strap can initiate separation along the separation line beginning at the through-cut. The second strap is configured and positioned in such a way that a pulling force applied to the second strap does not initiate separation along the separation line beginning at the through-cut, thereby making the second strap a useful positioning tool for positioning the flexible support structure.

In accordance with aspects of the present invention, the flexible support structure can be configured to be removed through an opening in a prosthesis having a total circumferential area that is less than the total circumferential area occupied by the flexible support structure when in the deployed configuration. The deployment device can include the separation line, and the deployment device further can further include a removable connector piece coupling the portions of the flexible support structure across the separation line. An additional strap can be coupled to the removable connector piece for removing the removable connector piece.

In accordance with aspects of the present invention, the deployment device can include the separation line, wherein the separation line includes a plurality of through-holes or a continuous strip of material. The deployment device can include the separation line in the flexible support structure. The separation line can include an inner portion having a first thickness and an outer portion having a second thickness, the first thickness being greater than the second thickness.

In accordance with aspects of the present invention, the first strap and the second strap can be coupled together at ends proximal the flexible support structure. The first strap and the second strap can be a continuous elongate strap. The first strap and the second strap can be adapted to lock together at ends distal from the flexible support structure forming a positioning tool suitable for positioning the device. The first strap and the second strap can be adapted to lock together at locations distal from the flexible support structure, and when in a locked configuration form a positioning tool for positioning the device, and when in an unlocked configuration form a removal tool enable the pulling force applied to the first strap to initiate the separation along the separation line beginning at the through-cut.

In accordance with aspects of the present invention, the total circumferential area of the flexible support structure configured in generally planar form in the deployed configuration can be sized and dimensioned to fit within and completely expand and deploy a prosthesis into which the device is positioned, the prosthesis comprising a top layer and a bottom layer coupled together and forming an enclosure therebetween into which the device is configured for placement. Separation along the separation line can terminate at a ring configuration formed by the outer perimeter of the flexible support structure. A reinforcing lip can be disposed along the separation line.

In accordance with an embodiment of the present invention, a system includes a prosthesis comprising a top layer and a bottom layer coupled together and forming an enclosure therebetween, the top layer having an aperture opening to the enclosure, wherein a circumferential area of the aperture is less than a circumferential area of the top layer in which the aperture is disposed. A deployment device is removably disposed within the enclosure. The deployment device includes a flexible support structure configured in generally planar form having a total circumferential area in a deployed configuration, and configured to independently apply a radial deployment force to achieve the deployed configuration when positioned within the enclosure of the prosthesis. A separation line in the flexible support structure extends in a generally serpentine shape from a central portion of the flexible support structure to a perimeter of the flexible support structure. A first strap coupled with the flexible support structure in the central portion extends through the aperture and external to the prosthesis. A second strap coupled with the flexible support structure in the central portion extends through the aperture and external to the prosthesis. A pulling force applied to the first strap can initiate separation along the separation line. The second strap can be positioned in such a way that a pulling force applied to the second strap does not initiate separation along the separation line. Wherein if a pulling force is applied to the first strap, separation occurs along the separation line the flexible support structure reconfigures from the generally planar form to an elongate continuous strip and continued pulling force causes the elongate continuous strip to pass through the aperture in such a way that the flexible support structure is ultimately removed from the prosthesis.

In accordance with aspects of the present invention, a through-cut can be disposed at and an innermost end of the separation line at the central portion of the flexible support structure. The first strap can be disposed proximal the through-cut. The second strap can be disposed more distal from the through-cut than the first strap.

In accordance with aspects of the present invention, portions of the flexible support structure along the separation line can be coupled together prior to removal and are configured to separate for removal of the deployment device from the prosthesis. The deployment device can include the separation line, and the separation line can include a plurality of through-holes or a continuous strip of material. The deployment device further can include a stress relief hole or opening situated in and through the flexible support structure proximate to an inner end of the separation line.

In accordance with aspects of the present invention, the separation line can include an inner portion having a first thickness and an outer portion having a second thickness, the first thickness being greater than the second thickness. The first strap and the second strap can be adapted to assume a locked configuration forming a positioning tool and an unlocked configuration forming a deployment device removal tool. The first strap and the second strap can be coupled together at ends proximal the flexible support structure. The first strap and the second strap can be a continuous elongate strap.

In accordance with aspects of the present invention, the flexible support structure can have an elasticity that generates a force sufficient to cause the prosthesis to assume a deployed configuration from a non-deployed configuration. The total circumferential area of the flexible support structure configured in generally planar form in the deployed configuration can be sized and dimensioned in such a way that the structure fits within and completely expands and deploys the prosthesis. Separation along the separation line can terminate at a ring configuration formed by the outer perimeter of the flexible support structure. A reinforcing lip can be disposed along the separation line.

In accordance with an embodiment of the present invention, a kit includes a prosthesis comprising a top layer and a bottom layer coupled together and forming an enclosure therebetween, the top layer having an aperture opening to the enclosure, wherein a circumferential area of the aperture is less than a circumferential area of the top layer in which the aperture is disposed. A deployment device provided in the kit can include a flexible support structure configured in generally planar form having a total circumferential area in a deployed configuration, and configured to independently apply a radial deployment force to achieve the deployed configuration when positioned within the enclosure of the prosthesis. A separation line in the flexible support structure extends in a generally serpentine shape from a central portion of the flexible support structure to a perimeter of the flexible support structure. A first strap couples with the flexible support structure in the central portion. A second strap couples with the flexible support structure in the central portion. A pulling force applied to the first strap initiates separation along the separation line. The second strap can be positioned in such a way that a pulling force applied to the second strap does not initiate separation along the separation line. If a pulling force is applied to the first strap, separation can occur along the separation line the flexible support structure reconfigures from the generally planar form to an elongate continuous strip capable of passing through the aperture of the prosthesis.

In accordance with an example embodiment of the present invention, a prosthesis can be diagrammatically parsable into first, second, third, and fourth quadrants having substantially equal areas. The prosthesis can include an enclosure extending substantially to a perimeter of the prosthesis at least once in at least two of the first, second, third, and fourth quadrants. A flexible support structure can be removably disposed at least partially within the enclosure and can occupy a total circumferential area. The flexible support structure can have an elasticity that generates a force sufficient to cause the prosthesis to assume a deployed configuration from a non-deployed configuration. A tab can be adjoined with the flexible support structure and extending external to the enclosure.

The flexible support structure can be configured in such a way that pulling the tab directionally away from the prosthesis causes a reconfiguration of the flexible support structure sufficient to enable the flexible support structure to pass through an opening in the prosthesis having a total circumferential area that is less than the total circumferential area occupied by the flexible support structure when the prosthesis is in the deployed configuration, thereby enabling removal of the flexible support structure from the enclosure.

In accordance with aspects of the present invention, the flexible support structure can include at least one flexible sheet member. The flexible sheet member can include two or more portions that do or do not overlap in a deployed state, depending on the embodiment. The flexible support structure can include a flexible sheet member having one or more slits or openings disposed therethrough. The one or more slits or openings can enable the flexible support structure to reconfigure during removal of the flexible support structure into a different shape having a peripheral edge that delineates a reduced effective diameter. The reconfiguration of the flexible support structure during removal of the flexible support structure can result in at least one of a reduced length of the flexible support structure, a reduced width of the flexible support structure, or a reduced effective diameter of the flexible support structure. The flexible support structure can be a flexible framework. The flexible support structure can be configured to apply a generally radially outward force on a radially outermost surface of the enclosure.

In accordance with aspects of the present invention, the tab can extend through the opening in the prosthesis. The opening in the prosthesis further can be disposed in and through a layer or surface of the prosthesis, in such a way that the central opening provides access to the enclosure. The opening in the prosthesis can be an outer opening disposed in and completely through the outer surface of the enclosure. The tab can extend through the outer opening in the outer surface of the enclosure. The tab can include one or more elongate straps.

In accordance with aspects of the present invention, the flexible support structure further can include a separation line extending in a generally serpentine shape from a central portion of the flexible support structure to a perimeter of the flexible support structure. The serpentine separation line can follow along a continuous strip of material. The serpentine separation line can include a plurality of through-holes. The flexible support structure further can include a stress relief hole situated at an inner end of the separation line. The tab can include one or more straps, and the flexible support structure further can include two or more slots for receiving the one or more straps.

An edge can extend in a generally serpentine shape from a central portion of the flexible support structure to a perimeter of the flexible support structure. A removable connector piece can be coupled to the flexible support structure, and the removable connector piece can securely connect portions of the flexible support structure abutting along the edge to each other. The removable connector piece can include a central portion and one or more elongate portions coupled to the central portion, and the flexible support structure further can include a plurality of slits for receiving the one or more elongate portions. The tab can include one or more straps, and the flexible support structure further can include two or more slots for receiving the one or more straps. A stress relief hole can be situated at an inner end of the edge.

In accordance with an example embodiment of the present invention, an implantable prosthesis deployment device can include a flexible support structure for removable insertion at least partially within an enclosure of an implantable prosthesis. The flexible support structure can occupy a total circumferential area and can have an elasticity sufficient to generate a force sufficient to cause the prosthesis to assume a deployed configuration when placed in the prosthesis and after being flexed to a non-deployed configuration. A tab can be adjoined with the flexible support structure and can have a length sufficient to extend external to the enclosure when the flexible support structure is in a deployed configuration in the prosthesis. The flexible support structure can be configured in such a way that pulling the tab directionally away from the prosthesis when the flexible support structure is inserted in the prosthesis causes a reconfiguration of the flexible support structure sufficient to enable the flexible support structure to pass through an opening in the prosthesis having a total circumferential area that is less than the total circumferential area occupied by the flexible support structure when the prosthesis is in the deployed configuration, thereby enabling removal of the flexible support structure from the enclosure.

In accordance with aspects of the present invention, the flexible support structure can include at least one flexible sheet member. The flexible sheet member can include two or more portions that do or do not overlap in a deployed state, depending on the embodiment. The flexible support structure can include a flexible sheet member having one or more slits or openings disposed therethrough. The one or more slits or openings can enable the flexible support structure to reconfigure during removal of the flexible support structure into a different shape having a peripheral edge that delineates a reduced effective diameter. The reconfiguration of the flexible support structure during removal of the flexible support structure can result in a reduced cross-sectional length of the flexible support structure, a reduced cross-sectional width of the flexible support structure, or both. The flexible support structure comprises a flexible framework. The flexible support structure can be configured to apply a generally radially outward force on a radially outermost surface of the enclosure.

In accordance with aspects of the present invention, the tab can extend through the opening in the prosthesis, and the opening can be disposed in and through a layer or surface of the prosthesis, in such a way that the central opening provides access to the enclosure. The opening can include an outer opening disposed in and completely through the outer surface of the enclosure. The tab can extend through the outer opening in the outer surface of the enclosure. The tab can include one or more elongate straps.

In accordance with aspects of the present invention, the flexible support structure further can include a separation line extending in a generally serpentine shape from a central portion of the flexible support structure to a perimeter of the flexible support structure. The serpentine separation line can follow along a continuous strip of material. The serpentine separation line can include a plurality of through-holes. The flexible support structure further comprises a stress relief hole situated at an inner end of the separation line. The tab can include one or more straps, and the flexible support structure further can include two or more slots for receiving the one or more straps.

In accordance with aspects of the present invention, an edge can extend in a generally serpentine shape from a central portion of the flexible support structure to a perimeter of the flexible support structure. A removable connector piece can couple portions of the flexible support structure along the edge to each other. The removable connector piece comprises a central portion and one or more elongate portions coupled to the central portion, and wherein the flexible support structure further comprises a plurality of slits for receiving the one or more elongate portions. The tab can include one or more straps, and the flexible support structure further can include two or more slots for receiving the one or more straps. A stress relief hole can be situated at an inner end of the edge.

In accordance with an example embodiment of the present invention, a kit can include a prosthesis that is diagrammatically parsable into first, second, third, and fourth quadrants having substantially equal areas. The prosthesis can include an enclosure extending substantially to a perimeter of the prosthesis at least once in at least two of the first, second, third, and fourth quadrants. The kit can include a flexible support structure for removable insertion at least partially within the enclosure. The flexibly support structure can occupy a total circumferential area when in a deployed configuration, and the flexibility support structure can have a stiffness sufficient to cause the prosthesis to assume a deployed configuration when placed in the prosthesis. A tab can be adjoined with the flexible support structure and can have a length sufficient to extend external to the enclosure when the flexible support structure is in a deployed configuration in the prosthesis. The flexible support structure can be configured in such a way that pulling the tab directionally away from the prosthesis when the flexible support structure is inserted in the prosthesis causes a reconfiguration of the flexible support structure sufficient to enable the flexible support structure to pass through an opening in the prosthesis having a total circumferential area that is less than the total circumferential area occupied by the flexible support structure when the prosthesis is in the deployed configuration, thereby enabling removal of the flexible support structure from the enclosure.

In accordance with an example embodiment of the present invention, a system can include a deployment device and a prosthesis. The prosthesis can include a first layer and a second layer forming an enclosure. The deployment device can include a flexible support structure configured as a sheet and removably situated at least partially within the enclosure. The flexible support structure can occupy a total circumferential area and can have an elasticity sufficient to cause the prosthesis to independently assume a deployed configuration. An edge or a tear line can extend in a generally serpentine shape from a central portion of the flexible support structure to a perimeter of the flexible support structure. A strap can extend from the flexible support structure and external to the enclosure. Portions of the flexible support structure along the edge or tear line can be coupled together prior to removal and can be configured to separate for removal of the deployment device from the prosthesis.

In accordance with aspects of the present invention, the flexible support structure can be configured to be removed through an opening in the prosthesis having a total circumferential area that is less than the total circumferential area occupied by the flexible support structure when the prosthesis is in the deployed configuration. The deployment device can include the edge, and the deployment device further can include a removable connector piece coupling the portions of the flexible support structure along the edge. An additional strap can be coupled to the removable connector piece for removing the removable connector piece. The deployment device can include the tear line, and the tear line can include a plurality of through-holes or a continuous strip of material. A stress relief hole or opening can be situated in and through the flexible support structure proximate to an inner end of the edge or tear line. The edge or a tear line can include one or more branches connected to one another and each terminating at least one position on the flexible support structure.

In accordance with aspects of the present invention, the deployment device can include the separation line in the flexible support structure. The separation line can include an inner portion having a first thickness and an outer portion having a second thickness, and the first thickness can be greater than the second thickness. A serpentine through-cut can be situated in the flexible support structure and can extend from an inner portion of the flexible support structure to an inner edge of the separation line. The strap can include two strap appendages adapted to assume a locked configuration forming a positioning tool and an unlocked configuration forming a deployment device removal tool.

In accordance an embodiment of the present invention, a method of removing a deployment device from a prosthesis includes grasping a flexible support structure forming the deployment device that is removably disposed at least partially within an enclosure of a prosthesis and occupying a total circumferential area, the flexible support structure having an elasticity that generates a force sufficient to cause the prosthesis to assume a deployed configuration from a non-deployed configuration. The user then pulls the tab of the flexible support structure directionally away from the prosthesis, thereby reconfiguring the flexible support structure to enable the flexible support structure to pass through an opening in the prosthesis having a total circumferential area that is less than the total circumferential area occupied by the flexible support structure when the prosthesis is in the deployed configuration. With continued pulling, the tab of the flexible support structure is removed from the enclosure through the opening.

BRIEF DESCRIPTION OF THE FIGURES

These and other characteristics of the present invention will be more fully understood by reference to the following detailed description in conjunction with the attached drawings, in which.

DETAILED DESCRIPTION

Figure 1A:
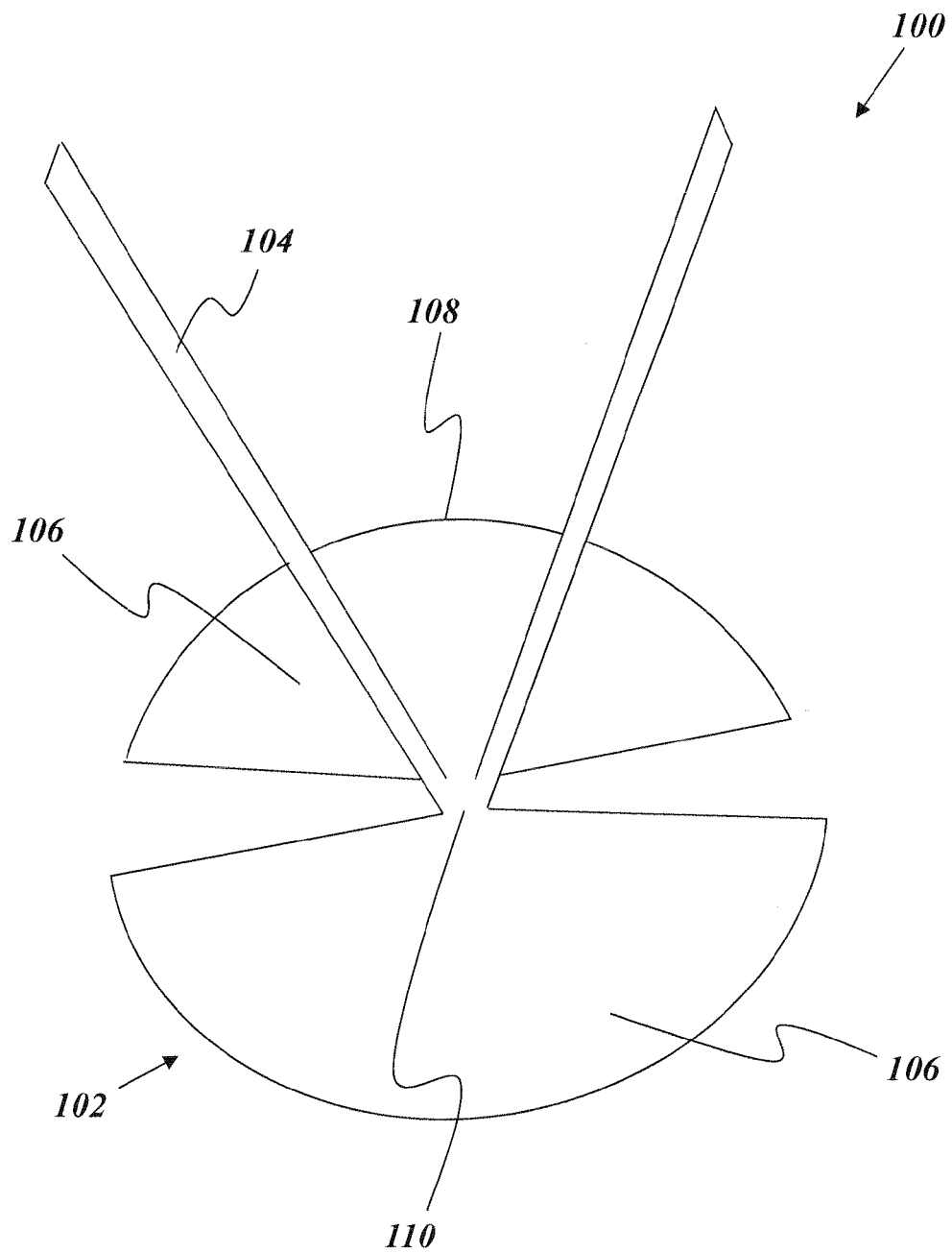
FIG. 1A depicts a perspective view of an example deployment device, according to aspects of the present invention.

An illustrative embodiment of the present invention relates to a deployment device capable of deploying a prosthesis, such as a hernia patch, with a more elegant and efficient design than other conventional deployment devices. The deployment device includes a flexible support structure that fits at least partially within an enclosure of the prosthesis, such as one or more pockets in the prosthesis formed by two stacked layers adjoined at a peripheral edge thereof. The flexible support structure has an elasticity that is sufficient to cause the prosthesis to deploy after implantation (e.g., by causing the prosthesis to independently assume a deployed, e.g., generally planar, shape after being implanted in a rolled or otherwise deformed configuration) and a flexibility sufficient to enable bending, folding, or otherwise assuming a collapsed or distorted configuration for removal from the prosthesis. In particular, the flexible support structure can have a flexibility sufficient to enable the flexible support structure to pass through an opening in the prosthesis that has a total circumferential area that is smaller than a total circumferential area of the deployment device. The deployment device additionally can include a tab that extends external to the enclosure and that, when pulled in a direction away from the prosthesis, causes the flexible support structure to reconfigure in a manner sufficient for removal of the flexible support structure.

Accordingly, the deployment device according to the illustrative embodiment of the present invention can have an elasticity that is sufficient for causing the prosthesis to assume a deployed (e.g., generally planar and non-collapsed) configuration at a target site even after being collapsed, compressed, or distorted in some manner (e.g., for implantation), and a flexibility sufficient for being removed from the prosthesis.

As utilized herein, the term "flexibility" adopts its conventional meaning in the art of the pliability of an object or extent to which an object permits bending. Flexibility thus includes bending due to different types of deformation, e.g., elastic deformation, plastic deformation, etc.

The term "elasticity" generally refers to the ability of an object to reversibly deform under stress, as is well known in the art. Elasticity thus endows an object with the ability to return to its original shape after the removal of stress (e.g., one or more external forces) that produced deformation of the object. Elasticity encompasses the ability of an object to return to a shape subsequent to deformation produced by expansion (e.g., elongation) and deformation produced by compression (e.g., as caused by folds, bends, etc. in an object).

FIGS. 1 through 31B, wherein like parts are designated by like reference numerals throughout, illustrate example embodiments of a deployment device according to the present invention. Although the present invention will be described with reference to the example embodiments illustrated in the figures, it should be understood that many alternative forms can embody the present invention. One of skill in the art will appreciate many different ways to alter the parameters of the embodiments disclosed, such as the size, shape, or type of elements or materials, in a manner still in keeping with the spirit and scope of the present invention.

Figure 1B:
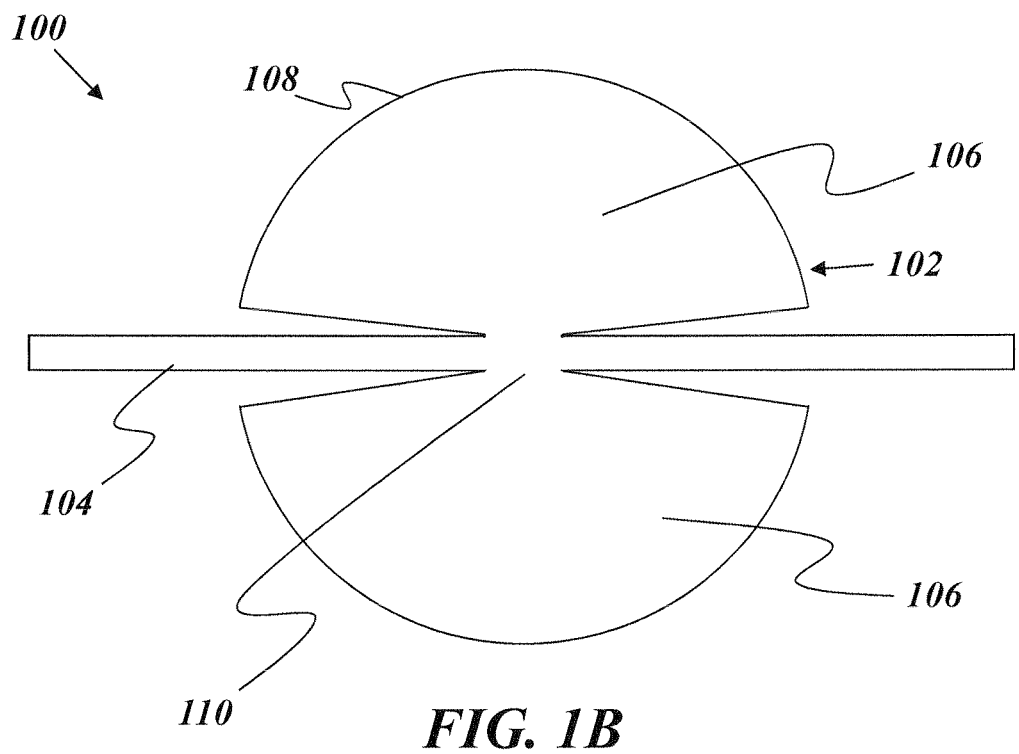
FIG. 1B depicts a top view of the example deployment device of FIG. 1A, according to aspects of the present invention.

FIG. 1A depicts a perspective view of an example embodiment of a deployment device 100 according to the present invention. FIG. 1B further depicts the example deployment device 100 from a top view, and FIG. 1C further depicts a side view thereof. The deployment device 100 includes a flexible support structure 102 and one or more tabs 104. The flexible support structure 102 can include any of a wide variety of different shapes, forms, portions, and members. In the example embodiment of FIG. 1A, the flexible support structure 102 is generally circular in shape and forms a substantially flat sheet member having two portions 106. The two portions 106 each include a radially distal end 108 and a radially proximal end 110. The two portions 106 are adjoined at the radially proximal end 110. Alternatively, the two (or more) portions 106 can be adjoined at other positions or ends thereof. Both the flexible support structure 102 and the one or more tabs 104 can possess a substantially uniform thickness, or can have a thickness that varies across different positions thereon.

The one or more tabs 104 can be any protruding portion or member. As illustrative, non-limiting examples, the one or more tabs 104 can include elongate straps, flaps, strips of material, appendages, protuberances, any other protruding portion or member, portions thereof, or combinations thereof. As depicted in FIG. 1A, the tabs 104 of the first example embodiment include two elongate straps adjoined with the flexible support structure 102 at or near the proximal end 110. The flexible support structure 102 and the tabs 104 can be constructed of extruded polypropylene, low density polyethylene (LDPE), other plastic material, monofilament material, sheet material, or any other suitable biodegradable or non-biodegradable material, as would be appreciated by one of skill in the art upon reading the present specification.

Figure 2A:
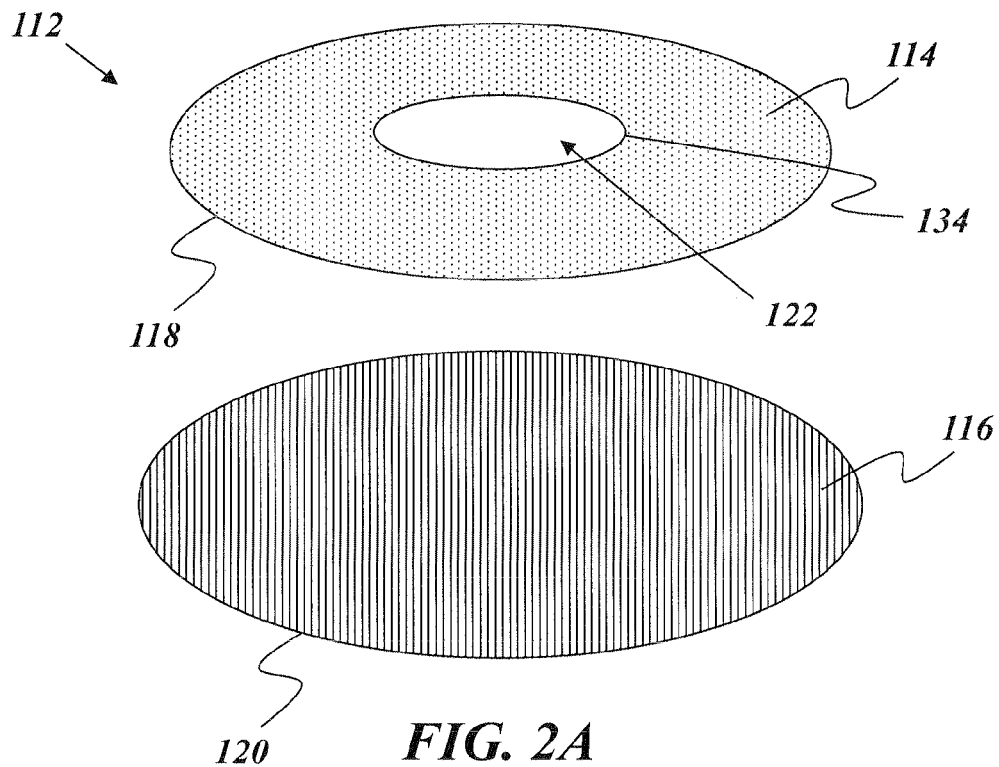
FIG. 2A depicts an exploded perspective view of an example prosthesis, according to aspects of the present invention.

FIG. 2A depicts an exploded view of an example prosthesis 112. The example prosthesis 112 is further illustrated in FIG. 2B from a perspective view and in FIG. 2C from a cross-sectional side view. The example prosthesis 112 can be formed of two or more stacked layers. The two or more stacked layers can include a first (e.g., top) layer 114 and a second (e.g., bottom) layer 116. The first layer 114 and the second layer 116 each can be a flexible sheet mesh. As non-limiting examples, the mesh can be constructed from polytetrafluoroethylene (PTFE), other suitable fluoropolymer materials, or any other suitable material. The first layer 114 and the second layer 116 can be adjoined (e.g., affixed, coupled, adhered, fastened, sewn, stitched, or otherwise joined together) at a seam (e.g., the outer perimeter 118 of the first layer 114). In illustrative embodiments depicted herein, the first layer 114 and the second layer 116 can be adjoined at or near the outer perimeter 118 of the first layer 114, so as allow for the formation of an enclosure 124 that extends substantially to the outer perimeter 118 of the first layer 114, substantially to the outer perimeter 120 of the second layer 116, or both (as depicted in the example embodiment of FIG. 2A through 2C).

The prosthesis 112 can include a portion 126 between the outer perimeter of the first layer 114 and the outer perimeter of the second layer 116 for serving as a flap for suturing the prosthesis 112 during fixation, e.g., in laparoscopic repairs. Alternatively, fixation can be performed by affixing (tacking, suturing, etc.) the first layer 114, e.g., during open hernia repairs. In general, the present invention is not limited to any particular fixation procedure. Rather, one of skill in the art will appreciate a wide variety of ways to affix the prosthesis 112, depending on the particular type of surgical procedure.

Figure 2B:
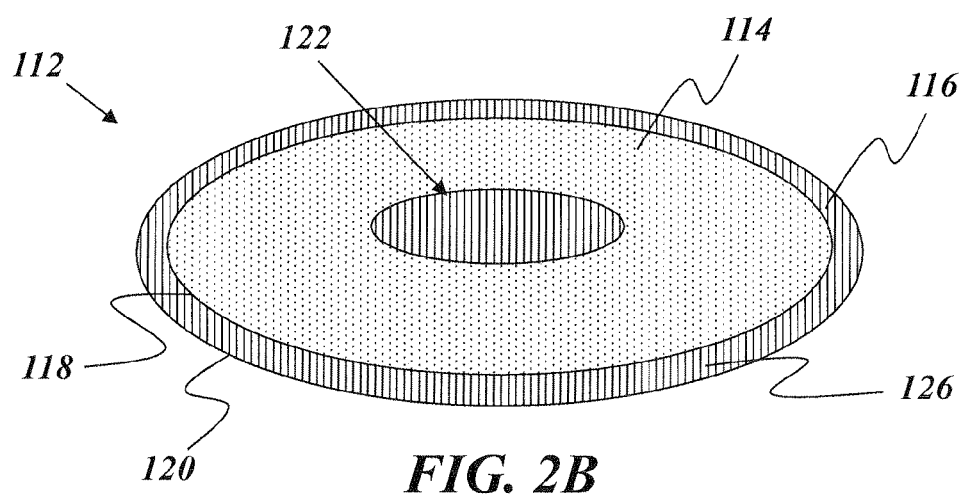
FIG. 2B depicts a perspective view of the example prosthesis of FIG. 2A, according to aspects of the present invention.
Figure 2C:
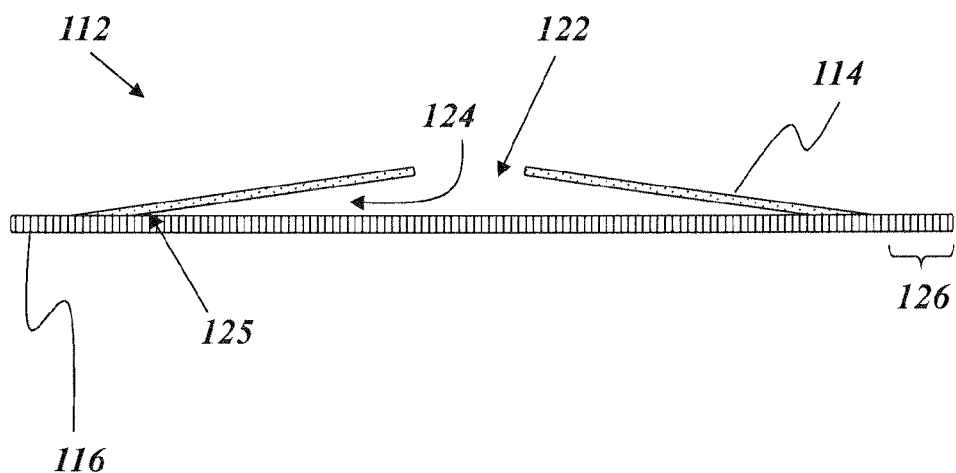
FIG. 2C depicts a side view of the example prosthesis of FIG. 2A, according to aspects of the present invention.

Furthermore, it should be appreciated that the example prosthesis 112 of FIGS. 2A through 2C is not intended to limit embodiments of the present invention. Thus, although the example embodiments described herein make repeated reference to the exemplary prostheses of the figures (e.g., hernia patches), embodiments of the present invention can be adapted for and utilized in any conventional, known, or otherwise suitable prosthesis, as would be appreciated by one of skill in the art upon reading the present specification.

The first layer 114 can include an aperture or opening 122 disposed therein and therethrough, e.g., for enabling access to the enclosure 124. The opening 122 can form an inner perimeter 134 on the prosthesis 112. As illustrated in FIGS. 2A through 2C, the opening 122 can consist of an inner opening in the first layer 114, i.e., contained entirely within the outer perimeter 118 of the first layer 114. Furthermore, the opening 122 can be a central opening, i.e., substantially centered in the first layer 114. Alternatively, the opening 122 can be situated elsewhere on the first layer 114 or on the second layer 116, and/or can extend to an edge thereof. While the opening 122 is depicted as generally circular in shape, the opening 122 can have any desired shape, including (as non-limiting examples) a general shape of an oblong, a polygon, an oval, a star, a triangle, a rectangle, a pentagon, a hexagon, etc. Furthermore, the opening 122 can be shaped to mimic the shape of the flexible support structure 102, or to mimic one or more portions of the flexible support structure 102. Alternatively, the opening 122 may be tailored and/or trimmed (e.g., to mimic the shape of the flexible support structure 102) by a surgeon immediately prior to placement of the prosthesis 112, as would be appreciated by one of skill in the art upon reading the present specification.

Figure 1C:
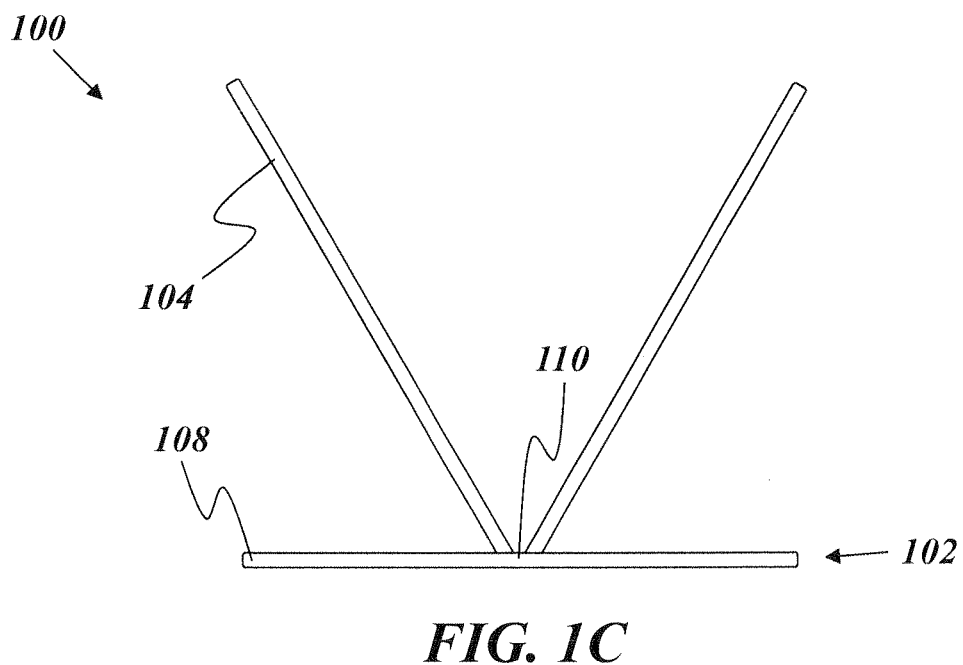
FIG. 1C depicts a side view of the example deployment device of FIG. 1A, according to aspects of the present invention.
Figure 3A:
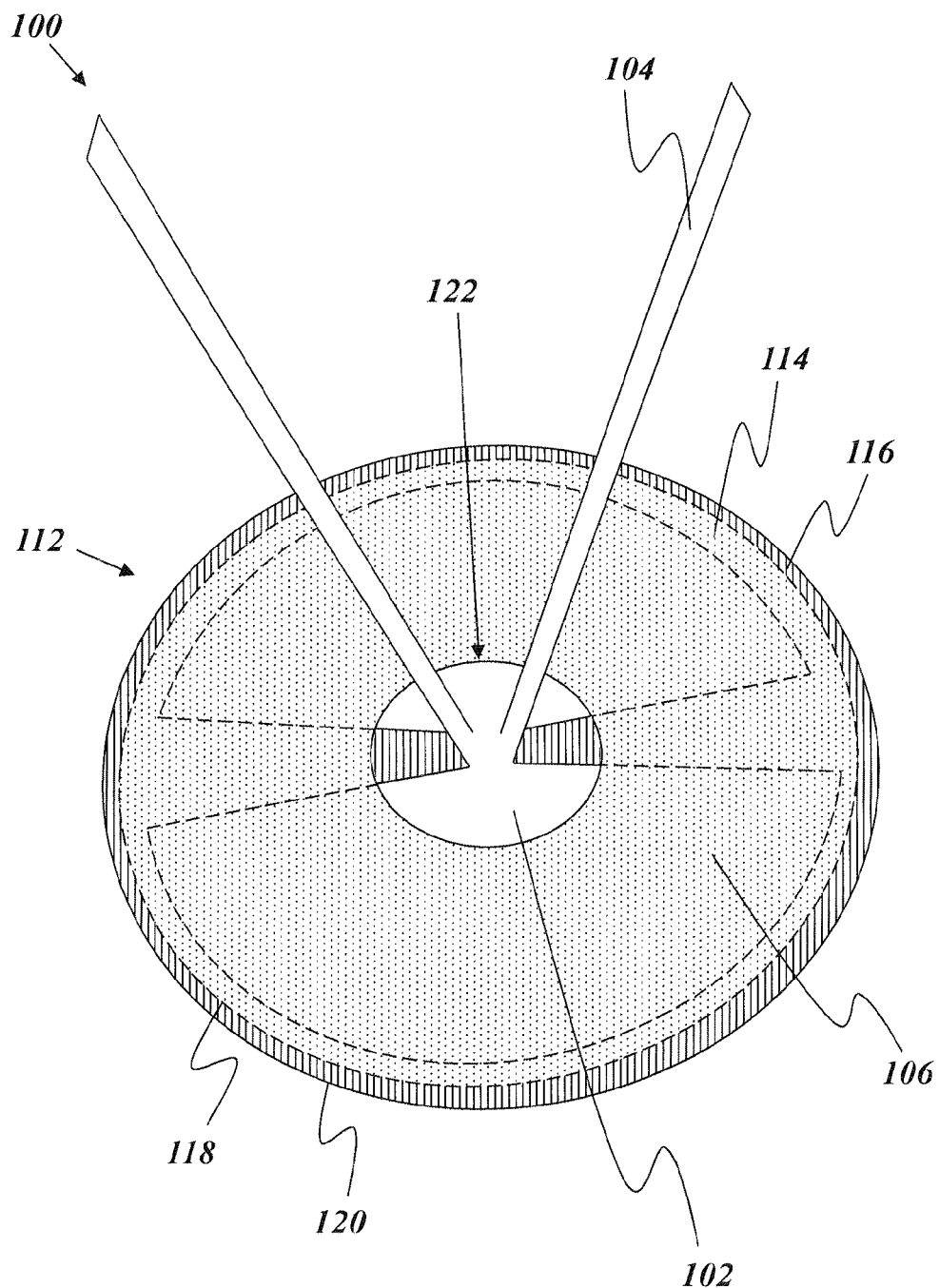
FIG. 3A depicts a perspective view of an example system including the example deployment device of FIG. 1A positioned in a deployed (e.g., generally planar) configuration within the example prosthesis of FIG. 2A, according to aspects of the present invention.

FIG. 3A depicts an example system that includes the prosthesis 112 of FIGS. 2A through 2C and the deployment device 100 of FIGS. 1A through 1C inserted into the prosthesis 112. The tabs 104 extend external to the enclosure 124, e.g., protrude beyond an outer edge of the enclosure 124. The flexible support structure 102 extends substantially to an outer perimeter of the prosthesis 112 (in this case, extends substantially to both the outer perimeter 118 of the first layer 114 and the outer perimeter 120 of the second layer 116). In some embodiments, the flexible support structure 102 extends to and is in contact with a radially outermost surface 125 of the enclosure 124 when the flexible support structure 102 is in a deployed (e.g., generally planar) configuration. Accordingly, the flexible support structure 102 can be configured to apply a generally radially outward force on the radially outermost surface 125 of the enclosure 124 when in the deployed (e.g., generally planar) configuration.

As depicted in FIG. 3A, the deployment device 100 can assume a deployed (e.g., generally planar) configuration within the prosthesis 112. More specifically, in the example embodiment of FIG. 3A, the deployed (e.g., generally planar) configuration of the deployment device 100 is characterized by an absence of folds, creases, bends, buckling, and the like in the flexible support structure 102. The deployed (e.g., generally planar) configuration can cause the prosthesis 112 to similarly assume a deployed (e.g., generally planar) configuration. For example, the size and/or shape of the flexible support structure 102 can be sufficient to cause the prosthesis 112 to deploy when the flexible support structure 102 is in a deployed (e.g., generally planar) configuration.

Figure 3B:
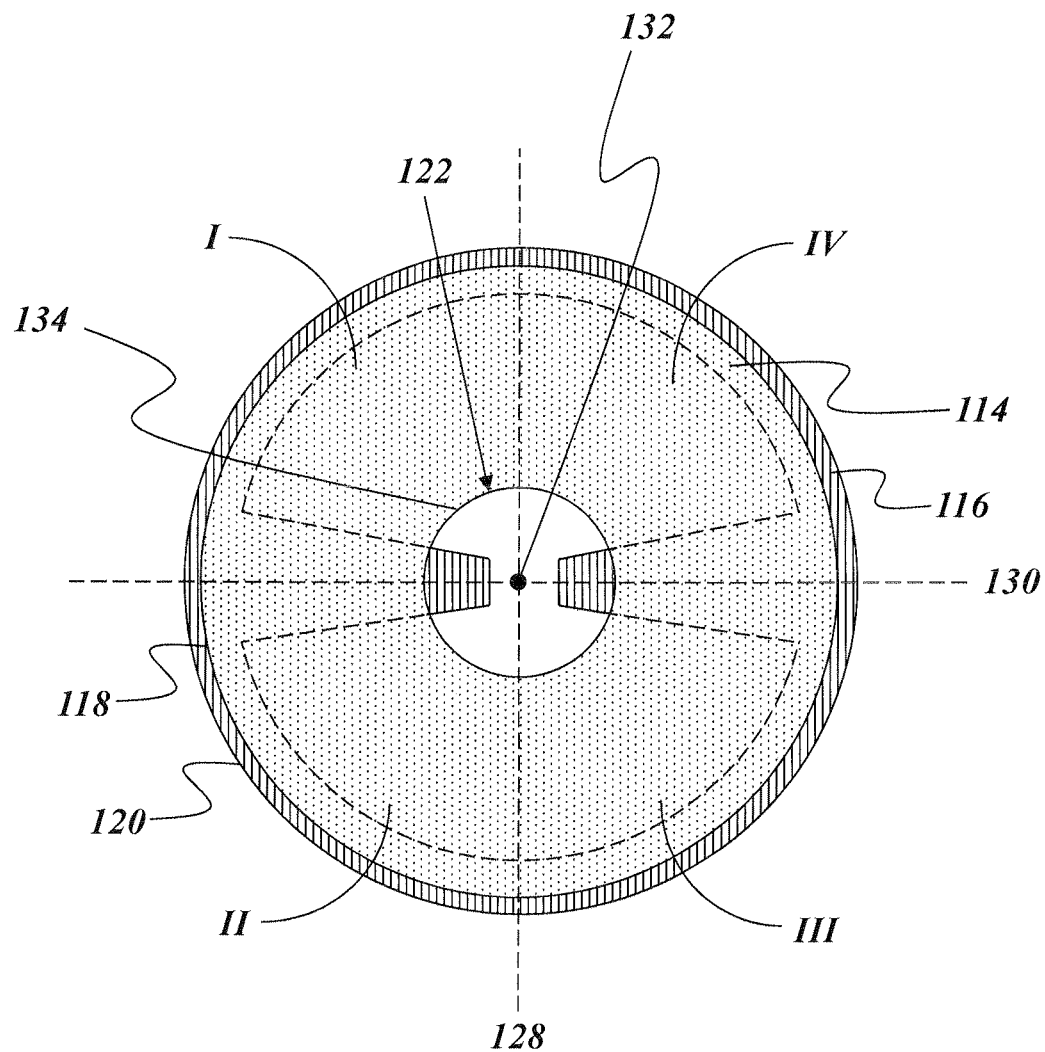
FIG. 3B depicts a top view of the example system of FIG. 3A when in the deployed (e.g., generally planar) configuration, according to aspects of the present invention.

FIG. 3B further depicts a top view of the system of FIG. 3A of the deployment device 100 and the prosthesis 112. For clarity, the tabs 104 are not shown. FIG. 3B illustrates that the prosthesis 112 can be diagrammatically parsed into four quadrants of substantially equal areas, quadrant I, quadrant II, quadrant III, and quadrant IV. The four quadrants I, II, III, and IV are divided by a horizontal axis 130 and a vertical axis 128 that pass through a center point 132 of the prosthesis 112. In illustrative embodiments, the enclosure 124 (not visible in the top view of FIG. 3B) can be formed in such a way as to extend substantially to a perimeter of the prosthesis 112 (e.g., outer perimeter 118 of the first layer 114 or outer perimeter 120 of the second layer 116) at least once in at least two of the four quadrants I, II, III, and IV. Furthermore, the enclosure 124 can extend to a perimeter of the prosthesis 112 at least once in at least one, in at least three, or in all four of the quadrants I, II, III, and IV. The enclosure 124 can form a closed loop around the center point 132, e.g., can extend around the inner perimeter 134 formed by the opening 122, as depicted in the example embodiment of FIGS. 3A through 3C.

Additionally, the flexible support structure 102 can extend into the enclosure 124 in at least one, in at least two, in at least three, or in all four of the quadrants I, II, III, and IV. In illustrative embodiments, and as depicted in FIG. 3B, the flexible support structure 102 extends substantially to an outer perimeter of the prosthesis 112 (e.g., the outer perimeter 118 and/or the outer perimeter 120) at least once in at least two of the four quadrants I, II, III, and IV. In further illustrative embodiments, the flexible support structure 102 extends substantially to an outer perimeter of the prosthesis 112 (e.g., the outer perimeter 118 and/or the outer perimeter 120) at least once in at least three of the four quadrants I, II, III, and IV. In yet further illustrative embodiments, the flexible support structure 102 extends substantially to an outer perimeter of the prosthesis 112 (e.g., the outer perimeter 118 and/or the outer perimeter 120) at least once in all four of the four quadrants I, II, III, and IV.

Continuing with FIG. 3A, the tabs 104 can extend external to the enclosure 124. For example, as illustrated, both of the tabs 104 extend out of the opening 122 when the deployment device 100 is situated in the prosthesis 112. (Alternatively, the tabs 104 can be configured to extend below the opening, as described in a later embodiment depicted with reference to FIG. 10B.) In such embodiments where the tabs 104 extend out of the opening 122, the tabs 104 can assume a non-flat configuration, e.g., as depicted in FIG. 3A. However, the tabs 104 further can be configured to assume a flat configuration, as depicted in the example embodiment of FIG. 3D. For instance, the tabs 104 can be coupled to the flexible support structure 102 by a hinge or can otherwise be enabled to hinge or pivot relative to the flexible support structure 102. This can enable the deployment device 100 to assume a substantially flat configuration that may be useful in reducing the size of packaging required to sell the deployment device 100. Accordingly, in such embodiments where the tabs 104 are packaged in a flat configuration, the tabs 104 subsequently can be moved into a more usable non-flat configuration (e.g., as depicted in FIG. 3A) after removal from the packaging.

The tabs 104 can be constructed of a material that is rigid (e.g., that is stiffer than the flexible support structure 102), to facilitate intraoperative maneuvering by a surgeon of the prosthesis 112 when the deployment device 100 is positioned in the prosthesis 112. Alternatively, the tabs 104 can be constructed of material that is more flexible than the flexible support structure 102. In general, one of skill in the art will appreciate a wide variety of suitable materials that can be utilized in making the tabs 104.

The flexible support structure 102 can be formed of a material having an elasticity that is sufficient to cause the flexible support structure 102 to independently assume a deployed (e.g., generally planar) configuration, e.g., in the absence of an external collapsing force applied by a surgeon or other operator handling the deployment device 100. For example, the elasticity of the material of the flexible support structure 102 can be sufficient to cause the flexible support structure 102 to independently return to a deployed (e.g., generally planar) configuration after being rolled, etc. for insertion into a patient. Accordingly, after inserting the flexible support structure 102 into the prosthesis 112 and implanting the prosthesis 112 (e.g., in a rolled or folded configuration), the elasticity of the flexible support structure 102 causes the flexible support structure 102 and the prosthesis 112 to "spring" back into (or otherwise assume) the deployed (e.g., generally planar) configuration.

The flexible support structure 102 can be provided with a particular thickness and material type that results in the desired values of flexibility and elasticity. For example, in some embodiments of the present invention implemented for open hernia repairs, the flexible support structure 102 is constructed of extruded polyester or polypropylene having a substantially uniform thickness of about 0.0075 inches to about 0.010 inches. One of skill in the art will appreciate that this thickness value represents a device that is substantially thinner than existing prior art deployment devices utilizing permanent rings or frame members.

Furthermore, the flexibility of the flexible support structure 102 can be sufficiently high to enable the flexible support structure 102 to assume a collapsed configuration (e.g., folded, bent, etc.) during removal of the deployment device 100 from the prosthesis 112, e.g., while the prosthesis 112 is being held in place. For example, an upward tensile force exerted by a surgeon on the flexible support structure 102 by pulling the tabs 104 in a direction away from the affixed prosthesis 112 can initiate the bending, folding, collapsing, or other reconfiguration in shape of the flexible support structure 102 necessary to liberate the flexible support structure 102 from the enclosure 124 of the prosthesis 112. This is depicted in FIG. 3C, which illustrates the deployment device 100 of FIG. 3A during removal from the prosthesis 112.

Figure 3C:
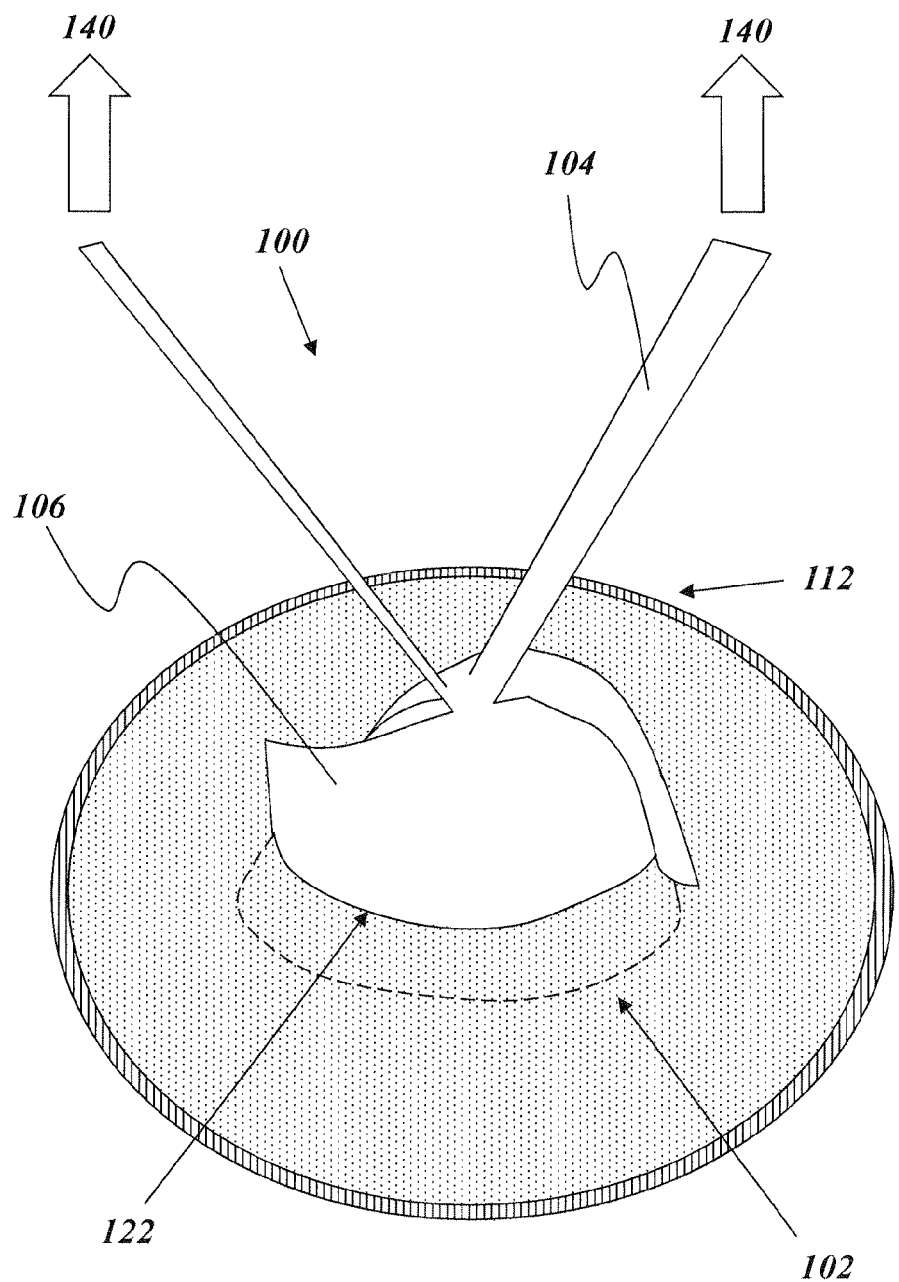
FIG. 3C depicts a perspective view of the system of FIG. 3A during removal of the example deployment device from the example prosthesis, according to aspects of the present invention.
Figure 3D:
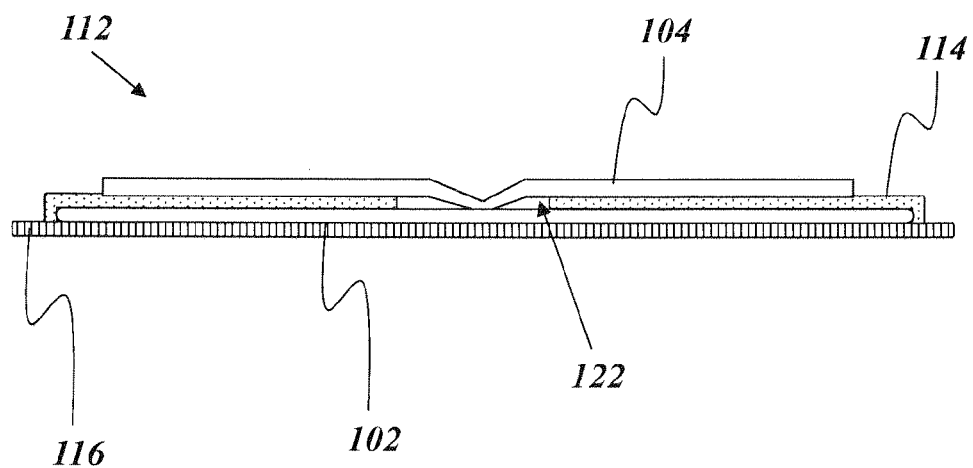
FIG. 3D depicts a side view of the system of FIG. 3A when in the deployed (e.g., generally planar) configuration, according to aspects of the present invention.

As one example, the deployment device 100 can be removed by holding the prosthesis 112 in a fixed position (e.g., using sutures or tacks to secure the prosthesis in place against tissue, muscle wall, etc.) and simultaneously pulling the tabs 104 in a direction away from the prosthesis 112, such as an upward direction 140 (see FIG. 3C). During such a process, the flexible support structure 102 experiences an upward force at the position where the tabs 104 are joined with the flexible support structure 102. The upward force causes the flexible support structure 102 to lift up off the second layer 116 and encounter the first layer 114. The lifting motion can cause the enclosure 124 to expand in height, as the first layer 114 similarly lifts in response to contact with the flexible support structure 102. As the upward pull continues, portions of the flexible support structure 102 contacting the first layer 114 experience a downward force resisting the upward motion, while other portions not covered by the first layer 114 (e.g., positioned directly beneath the opening 122) do not experience such resistance. The difference in applied forces causes the flexible support structure 102 to undergo a reconfiguration (e.g., a deformation in shape, orientation, or both) sufficient to enable the flexible support structure 102 to reduce its effective cross-sectional area and pass through the opening 122 in the prosthesis 112. For example, the reconfiguration of the flexible support structure 102 can include at least one bend, fold, crease, buckle, or other collapsing action or state.

The size and/or orientation of the flexible support structure 102 can be different from the shape and/or size of the opening 122. In illustrative embodiments, the flexible support structure 102 is larger in size (e.g., in one or more dimensions, in area, in volume occupied, effective cross-sectional area, or the like) than the opening 112. For instance, in embodiments where the flexible support structure 102 has a generally circular top profile shape, the flexible support structure 102 can have an effective diameter that is greater than a diameter of the opening 122. In embodiments where the flexible support structure 102 has a generally non-circular top profile shape, the flexible support structure 102 can have a length or a width that is greater than a length or width of the opening 122. Stated differently, the flexible support structure 102, when positioned in the prosthesis 112 in a deployed (e.g., generally planar) configuration, generally can have a top profile shape that extends beyond a top profile shape of the opening 112.

Additionally, the opening 122 can have a total circumferential area that is less than a total circumferential area occupied by the flexible support structure 102 when the prosthesis 112 and the flexible support structure 102 are in the deployed (e.g., generally planar) configuration (as depicted in FIG. 3A). In further embodiments, the opening 122 can have a total circumferential area that is substantially less than the total circumferential area occupied by the flexible support structure 102 when the prosthesis 112 and the flexible support structure 102 are in the deployed (e.g., generally planar) configuration. In yet further embodiments, the opening 122 can have a total circumferential area that is significantly less than the total circumferential area occupied by the flexible support structure 102 when the prosthesis 112 and the flexible support structure 102 are in the deployed (e.g., generally planar) configuration. As some examples, and depending on the particular shape of the prosthesis 112, the flexible support structure 102 (when in a deployed (e.g., generally planar) configuration in the prosthesis 112) can have a total circumferential area that is about 5% more, about 10% more, about 15% more, about 20% more, about 25% more, about 30% more, about 35% more, about 40% more, about 45% more, about 50% more, about 55% more, about 60% more, about 65% more, about 70% more, about 75% more, about 80% more, about 85% more, about 90% more, about 95% more, about 100% more, about 105% more, about 110% more, about 115% more, about 120% more, about 125% more, about 130% more, about 135% more, about 140% more, about 145% more, about 150% more, about 155% more, about 160% more, about 165% more, about 170% more, about 175% more, about 180% more, about 185% more, about 190% more, or about 195% more, about 200% more, or greater than about 200% more (or some intermediate value lying therebetween) than a total circumferential area occupied by the opening 122.

Figure 4A:
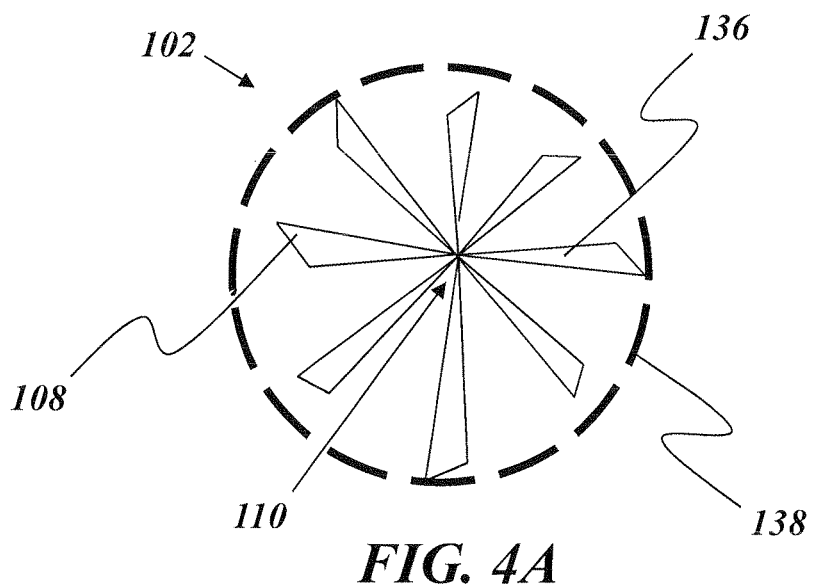
FIG. 4A depicts a top view of an example prosthesis and a circle delineating a total circumferential area of the example prosthesis, according to aspects of the present invention.
Figure 4B:
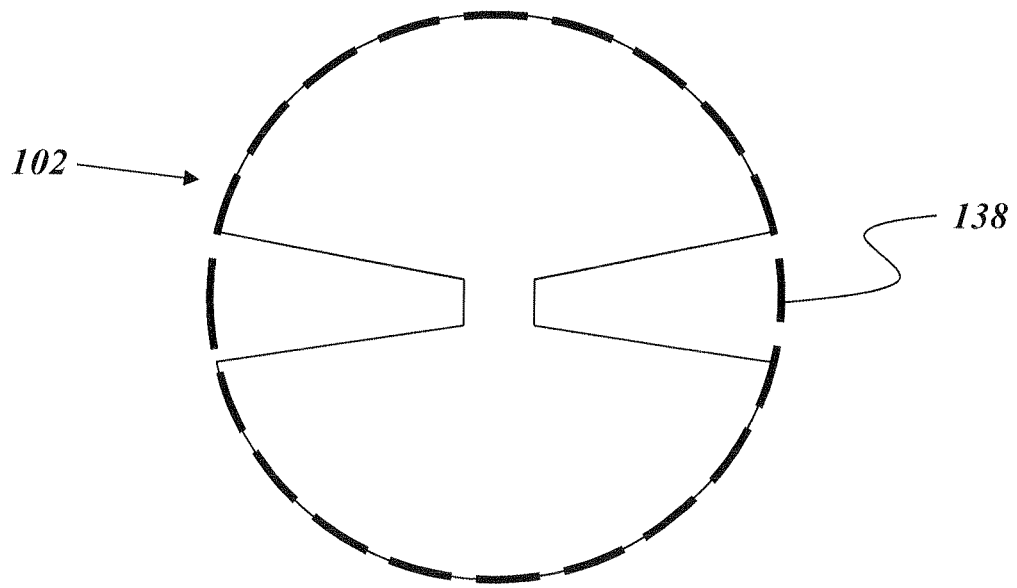
FIG. 4B depicts a top view of the example prosthesis of FIG. 1A and a circle delineating a total circumferential area of the example prosthesis, according to aspects of the present invention.

The total circumferential area of the flexible support structure 102 generally can be defined as the area of the smallest theoretical circle that can be constructed to fully contain, on or inside its perimeter, the entire profile of the flexible support structure 102 when viewed from the directly above (e.g., from the top view of FIG. 3B). For example, FIG. 4A depicts another example of a flexible support structure 102 having a plurality of adjoined appendages 136, which can have different lengths. Each appendage 136 includes a distal end 108 and a proximal end 110. A theoretical circle 138 is illustrated in bold, dashed lines, which encloses the entire profile of the flexible support structure 102 when viewed from above. The theoretical circle 138 is the smallest possible theoretical circle that can be constructed around the prosthesis 102, since the theoretical circle 138 contains (in or on its perimeter) the entire profile of the flexible support structure 102 and since the perimeter of the flexible support structure 102 intersects with at least three points on theoretical circle 138. Accordingly, FIG. 4B depicts the smallest theoretical circle 138 containing (in or on its perimeter) the entire top view profile of the flexible support structure 102 of FIGS. 1A through 1C. Similarly, the total circumferential area of the opening 122 also can be determined in this way.

Accordingly, during removal, the flexible support structure 102 can assume a reconfiguration wherein the flexible support structure 102 possesses an increased height, e.g., as compared to a height of the flexible support structure 102 in a deployed (e.g., generally planar) configuration. Additionally, during removal, the flexible support structure 102 can assume a reconfiguration characterized by a reduced total circumferential area. For example, this is illustrated in FIG. 3C, which to shows the flexible support structure 102 during removal having a three-dimensional shape generally resembling that of a cone possessing a height that is greater than the height of the sheet members forming the portions 106 of the deployed (e.g., generally planar) flexible support structure 102 depicted in FIG. 3A. For example, in illustrative embodiments adapted for open hernia repair, the flexible support structure 102 can be transformed from a nearly contiguous flat circle having a diameter of about 2.6 inches to a configuration suitable for fitting through a circular orifice area having a diameter of about 0.5 inches. One of skill in the art will appreciate that these values are illustrative and do not limit the present invention.

In illustrative embodiments, the flexible support structure 102 can be disposed within the enclosure 124 of the prosthesis 112 and can occupy a total circumferential area therein in such a way that causes the prosthesis 112 to be in a deployed (e.g., generally planar) configuration, e.g., as depicted in FIG. 3A.

Figure 5A:
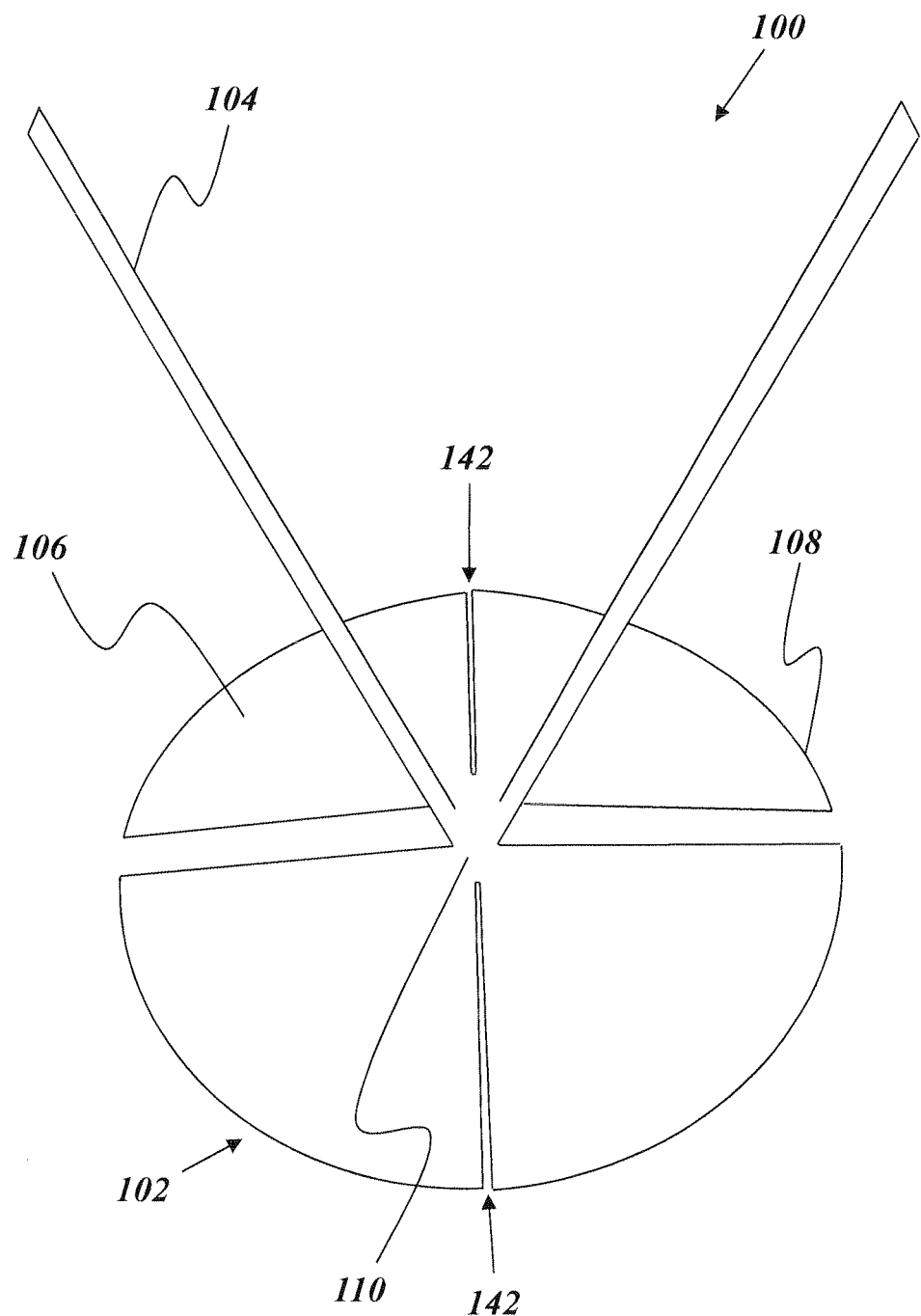
FIG. 5A depicts a perspective view of another example deployment device having slits or openings, according to aspects of the present invention.
Figure 5B:
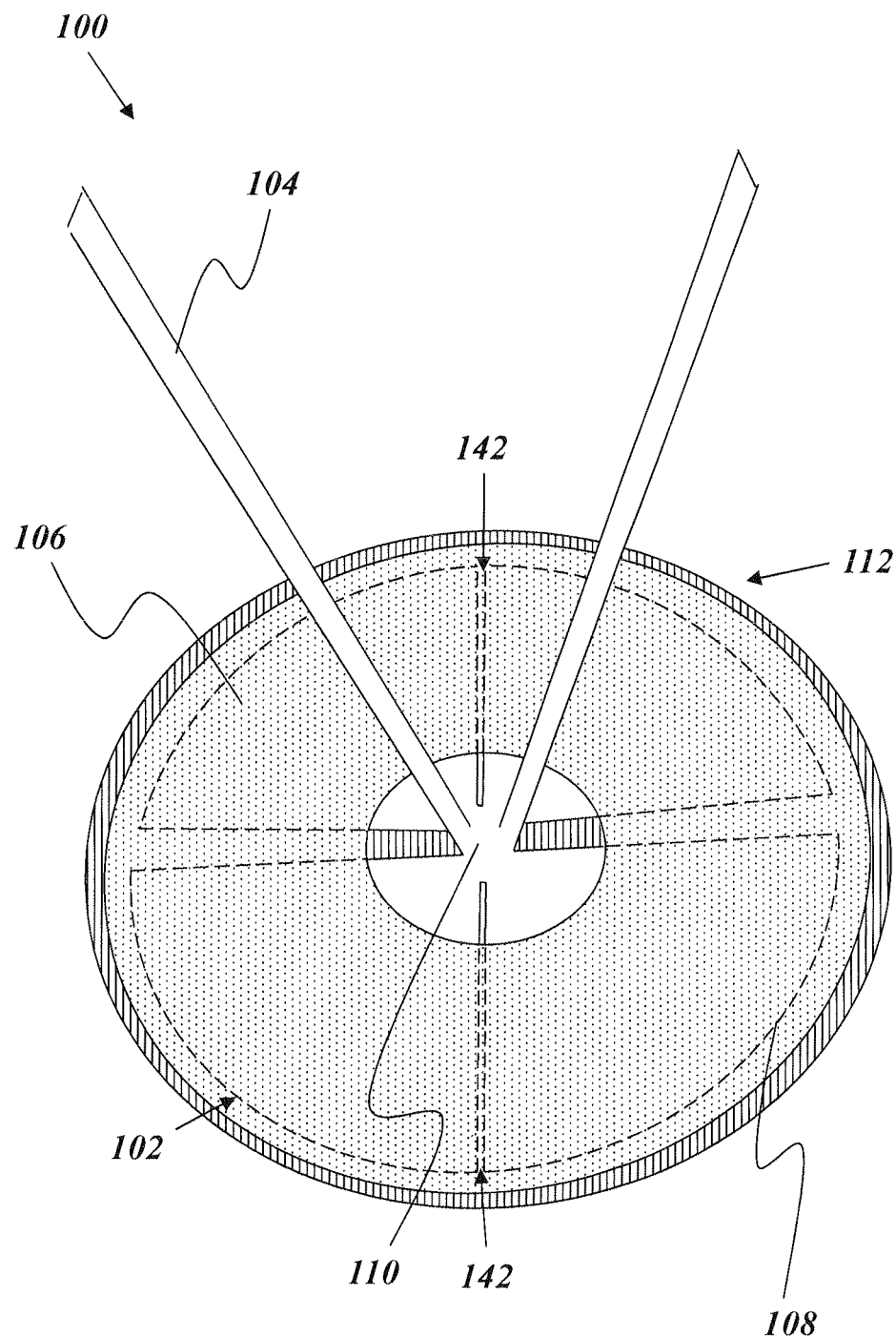
FIG. 5B depicts a perspective view of another example system including the example deployment device of FIG. 5A positioned in a deployed (e.g., generally planar) configuration in the example prosthesis of FIG. 2A, according to aspects of the present invention.
Figure 5C:
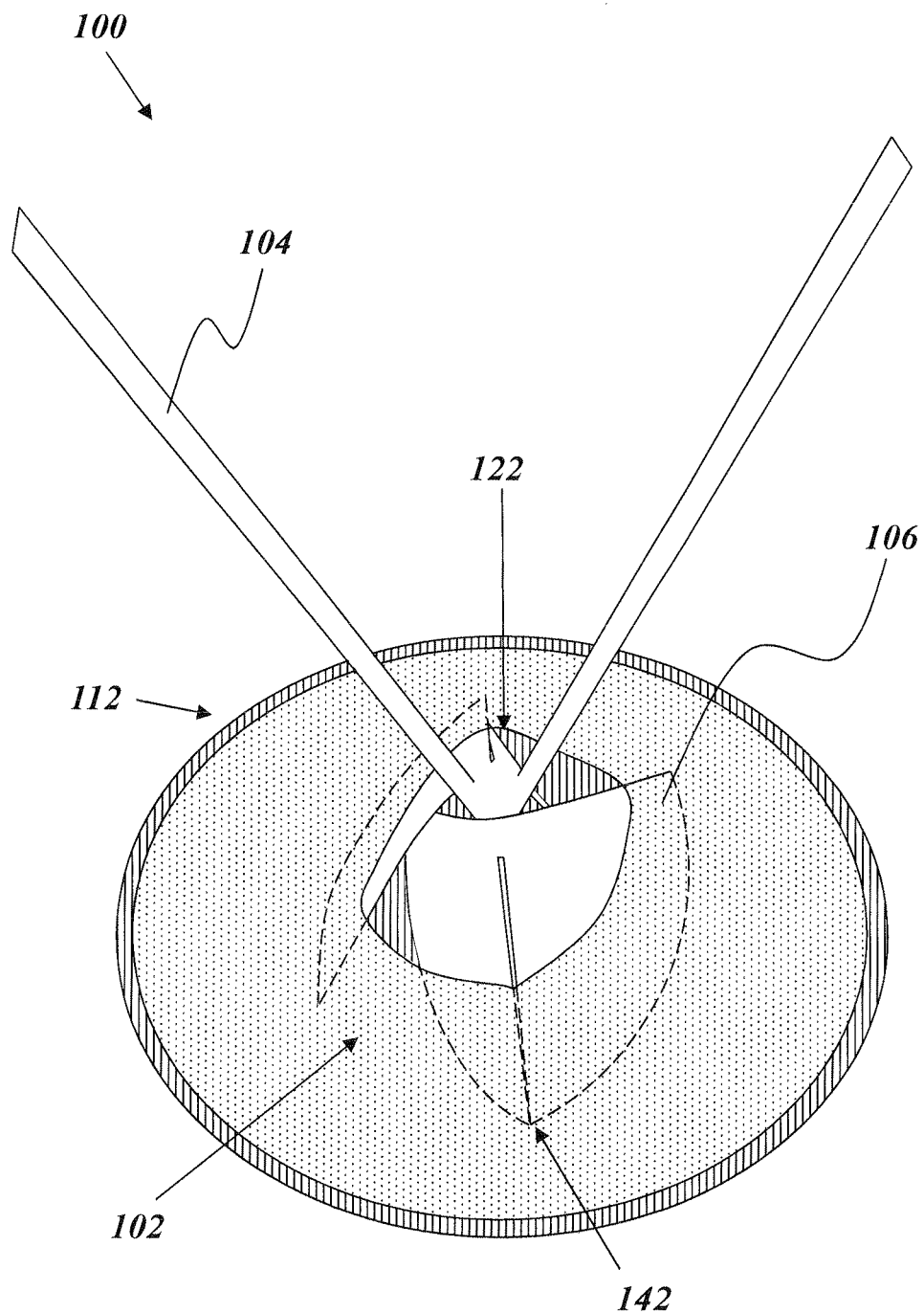
FIG. 5C depicts a perspective view of the example system of FIG. 5B during removal of the example deployment device from the example prosthesis, according to aspects of the present invention.

Although FIGS. 1A through 1C depict the example flexible support structure 102 as having only two portions 106, the flexible support structure 102 can have more or less such portions. For instance, FIG. 5A depicts another example embodiment of the deployment device 100 that consists of four such portions 106. The four portions 106 are divided into substantially equal areas and have substantially similar shapes and dimensions. In alternative embodiments, the shapes, areas, and dimensions of the various portions 106 can vary, e.g., based on the shape of the prosthesis 112 into which the flexible support structure 102 will fit. Some or all of the portions 106 can be separated from one another by thin elongate openings, such as the slits 142. The slits 142 can enable the flexible support structure 102 to reconfigure during removal from the prosthesis 112 into a different shape having a peripheral edge that delineates a reduced diameter or effective diameter, i.e., a diameter that is less than the diameter of the peripheral edge of the flexible support structure 102 when in a deployed (e.g., generally planar) configuration in the prosthesis 112. FIG. 5B depicts the deployment device 100 positioned in the prosthesis 112 in a deployed (e.g., generally planar) configuration, and FIG. 5C further depicts the deployment device 100 during removal from the prosthesis 112.

Figure 6A:
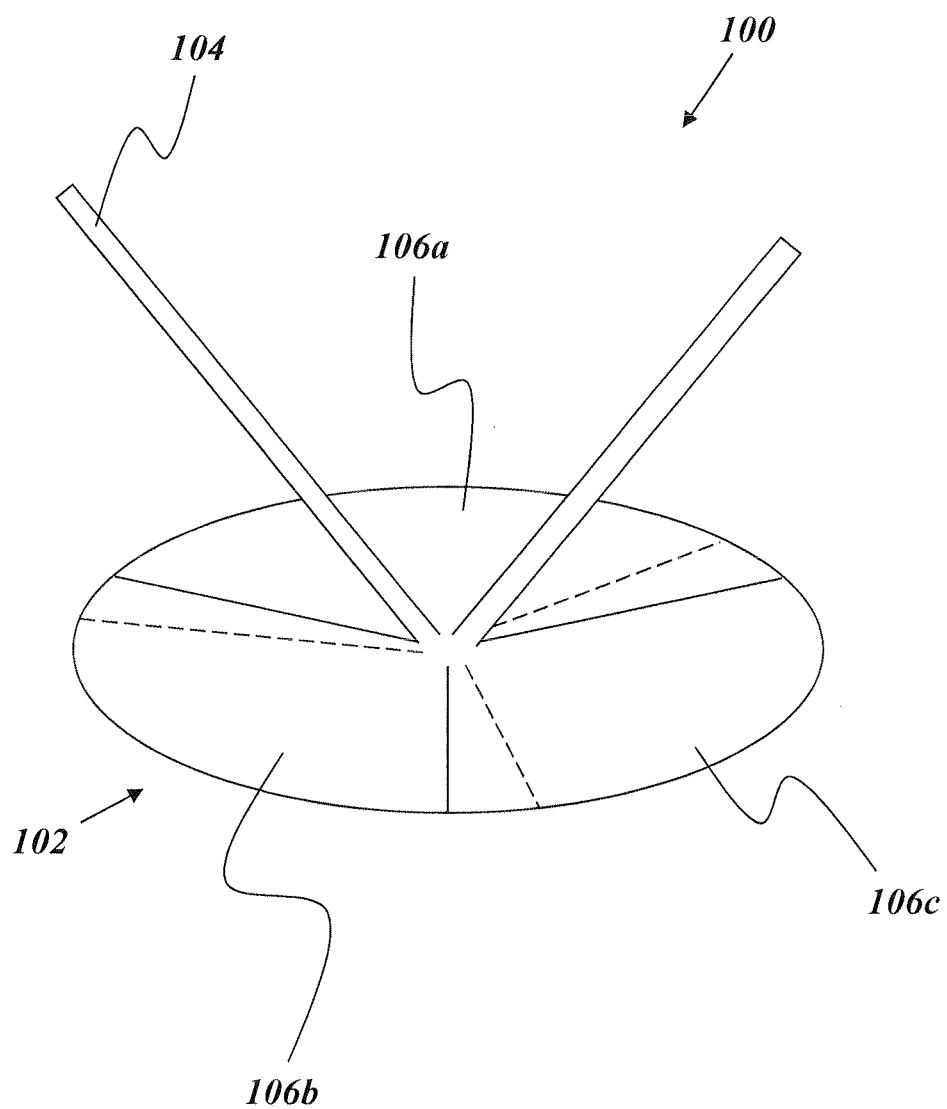
FIG. 6A depicts a perspective view of another example deployment device including one or more overlapping portions, according to aspects of the present invention.
Figure 6B:
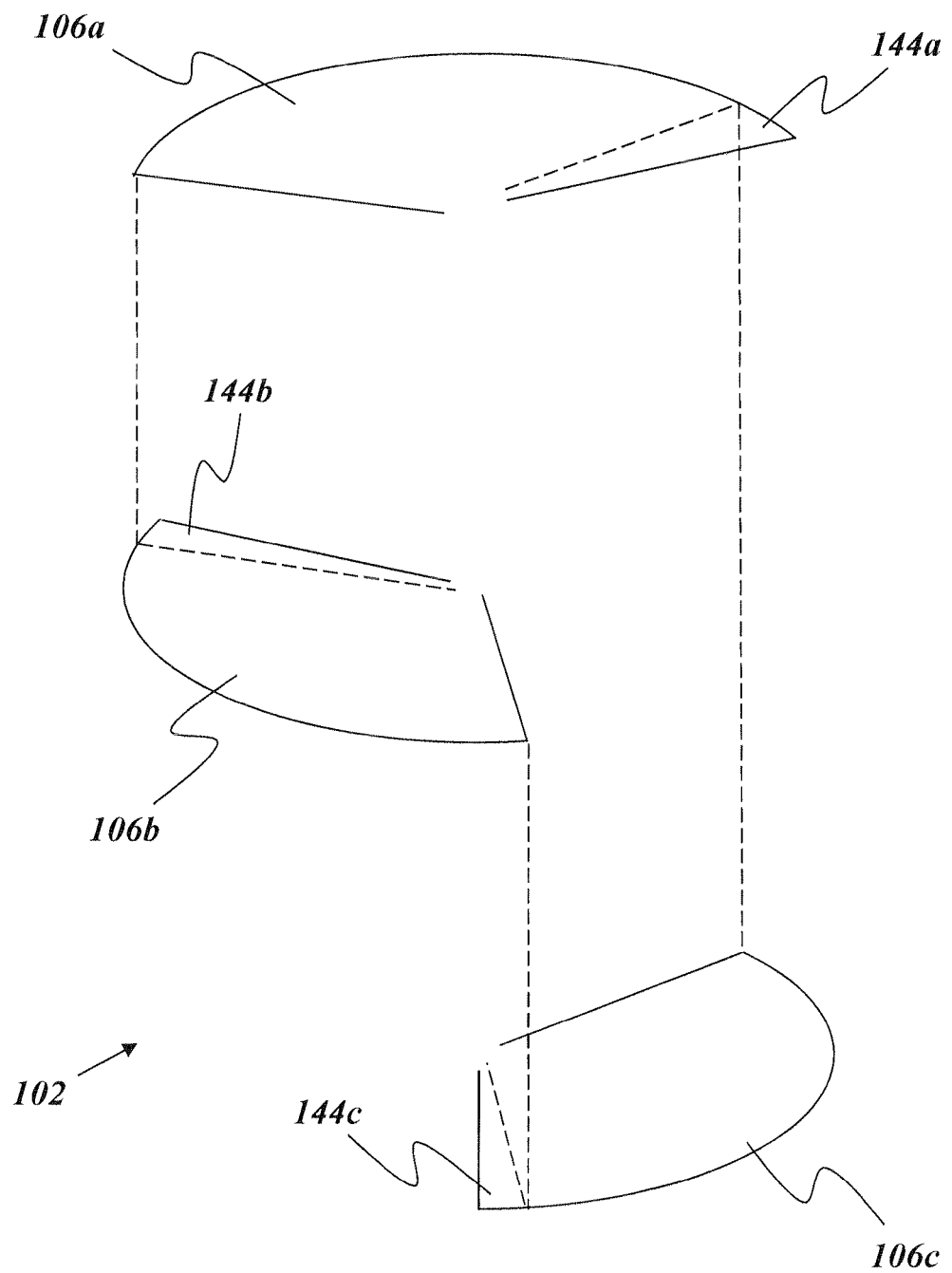
FIG. 6B depicts an exploded view of the example deployment device of FIG. 6A, illustrating the overlapping portions, according to aspects of the present invention.
Figure 6C:
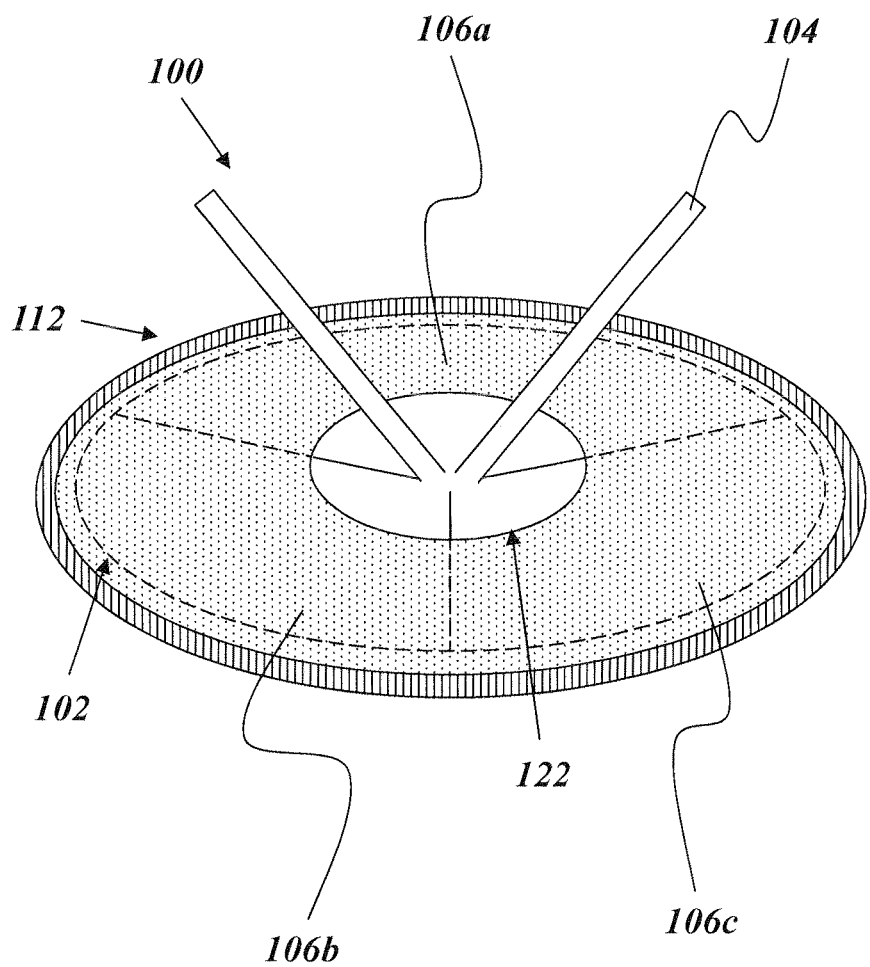
FIG. 6C depicts a perspective view of the example deployment device of FIG. 6A positioned in a deployed (e.g., generally planar) configuration in the example prosthesis of FIG. 2A, according to aspects of the present invention.

When in a deployed (e.g., generally planar) configuration, one or more of the portions 106 can be non-overlapping, e.g., as illustrated in FIGS. 3A and 5B. Alternatively, one or more of the portions 106 can be overlapping. For example, FIG. 6A illustrates another example embodiment that includes three portions 106$a$, 106$b$, and 106$c$, each of which overlaps with its two adjacent portions. This can be seen in FIG. 6B, which depicts the three portions 106$a$, 106$b$, and 106$e$ from an exploded view. The portion 106$b$ includes a flap 144$b$ that is covered by the portion 106$a$ when in the deployed (e.g., generally planar) configuration. Similarly, the portion 106$c$ includes a flap 144$c$ that is covered by the portion 106$b$ when in the deployed (e.g., generally planar) configuration. Furthermore, the portion 106$a$ includes a flap 144$a$ that is covered by the portion 106$c$ when in the deployed (e.g., generally planar) configuration. FIG. 6C further depicts the deployment device of FIG. 6A positioned within the prosthesis 112.

The portions 106 of the flexible support structure 102 generally can take on a wide range of other shapes, relative dimensions, and/or sizes. For example, FIGS. 7A through 7F depict additional embodiments of flexible support structure 102. One of skill in the art will appreciate that these examples are provided for purposes of further illustration and are not intended as limiting. Rather, a wide variety of different flexible support structures 102 and openings 122 having still other shapes, sizes, relative dimensions, and/or orientations, and combinations thereof, are possible and contemplated by the present invention.

Figure 7A:
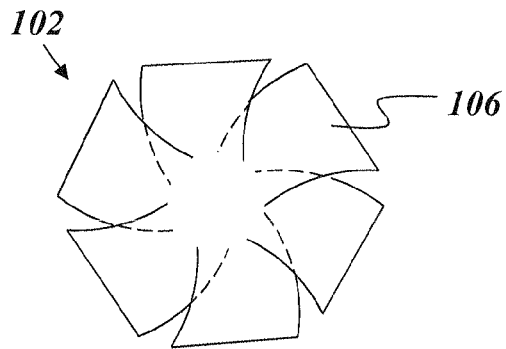
FIGS. 7A through 7C depict top views of example deployment devices having overlapping portions, according to aspects of the present invention.
Figure 7D:
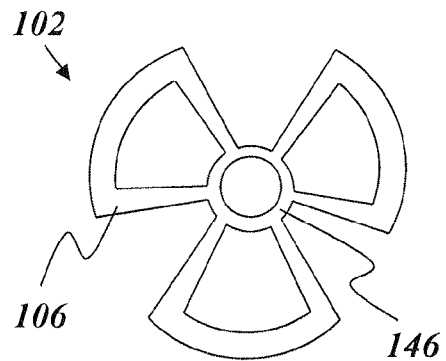
FIGS. 7D through 7F depicts top views of example deployment devices forming frameworks, according to aspects of the present invention.
Figure 7B:
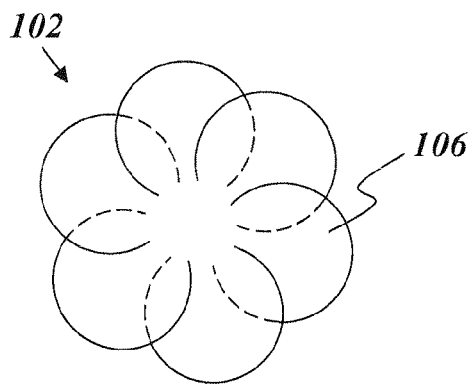
Figure 7E:
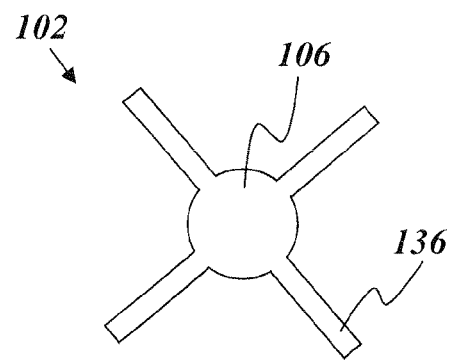
Figure 7C:
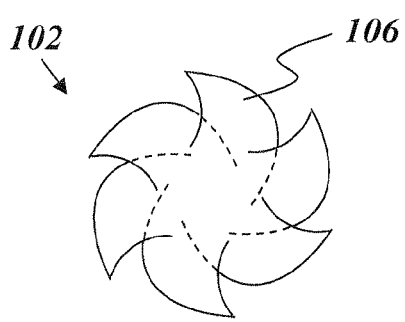

FIG. 7A depicts a flexible support structure 102 according to one example embodiment of the present invention, which includes six overlapping portions 106 each generally shaped to resemble a distorted rectangle. FIG. 7B depicts a flexible support structure 102 according to another example embodiment of the present invention, which includes six overlapping portions 106 each generally shaped to resemble a circle. FIG. 7C depicts a flexible support structure 102 according to yet another example embodiment of the present invention, which includes six overlapping portions 106 each generally shaped to resemble a distorted triangle.

Figure 7F:
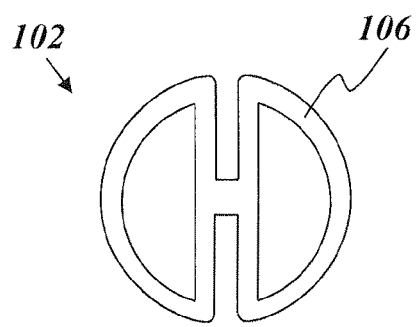

Furthermore, while embodiments provided herein include a flexible support structure 102 generally formed from sheet members, other embodiments are possible having different shapes and forms. For instance, the flexible support structure 102 can take the form of a framework, as depicted in the example embodiments of FIGS. 7D through 7F depict. More specifically, FIG. 7D depicts a flexible support structure 102 according to another example embodiment of the present invention, which forms a framework having three portions 106 adjoined by a proximal ring 146. FIG. 7E depicts a flexible support structure 102 according to another example embodiment of the present invention, which forms a framework having four appendages 136 adjoined by a central portion 106. FIG. 7F depicts a flexible support structure 102 according to another example embodiment of the present invention, which forms a framework having two portions 106 each generally shaped as a semicircle, e.g., which mimics in shape an edge of the enclosure 124 on the prosthesis 112. Yet other types and placements of portions connecting one or more of appendages 136 are possible.

Figure 8:
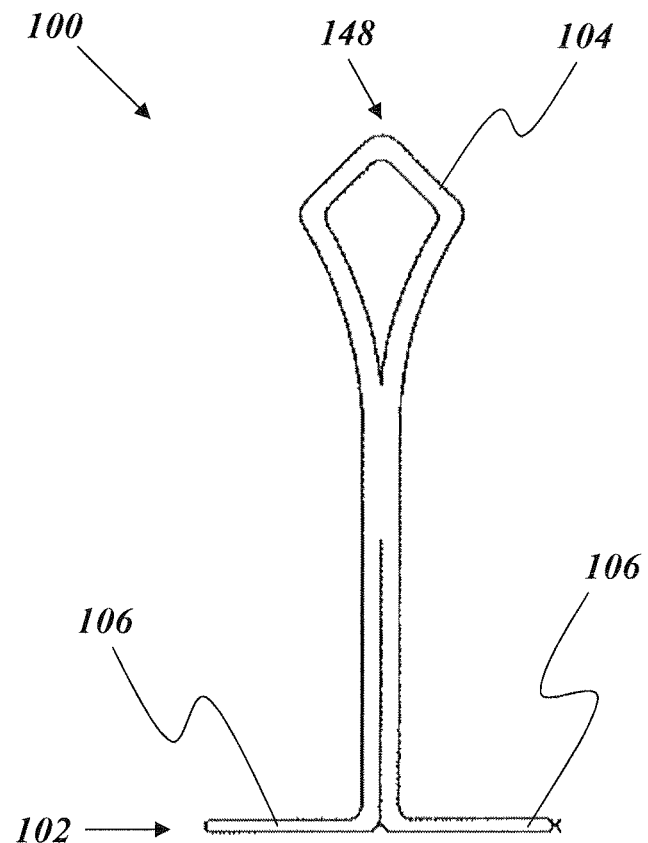
FIG. 8 depicts a side view of another example deployment device including two portions that are operationally connected by a tab including an elongate strap, according to aspects of the present invention.

Although the example embodiments of flexible support structures 102 depicted herein generally include various portions 106 that are connected to one another on the flexible support structure 102, other embodiments of flexible support structure 102 can include two or more portions 106 that are not connected on the flexible support structure. For instance, FIG. 8 depicts a side view of an alternative embodiment of a deployment device 100 that includes two portions 106 that are operationally connected to one another by the tab 104. In particular, the tab 104 forms a U-shaped elongate strap that extends away from the flexible support structure 102 and is folded at its distal end 148. The tab 104 joins with each of the portions 106, e.g., is formed integral therewith, is affixed thereto, is sewn thereto, is stitched thereto, is coupled thereto, is fastened thereto, is adhered thereto, or is otherwise joined therewith.

The example embodiments of FIGS. 1A through 8 are adapted for a generally circularly shaped prosthesis 112. However, embodiments of the present invention alternatively can be implemented for prostheses 112 having other (e.g., non-circular) shapes. In such alternative embodiments, the deployment device 100 can include the flexible support structure 102 of any of FIGS. 1A through 8, e.g., adjusted such that it has an outer perimeter that mimics the shape of the outer perimeter 118 of the first layer 114, the outer perimeter 120 of the second layer 116, or both.

Figure 9:
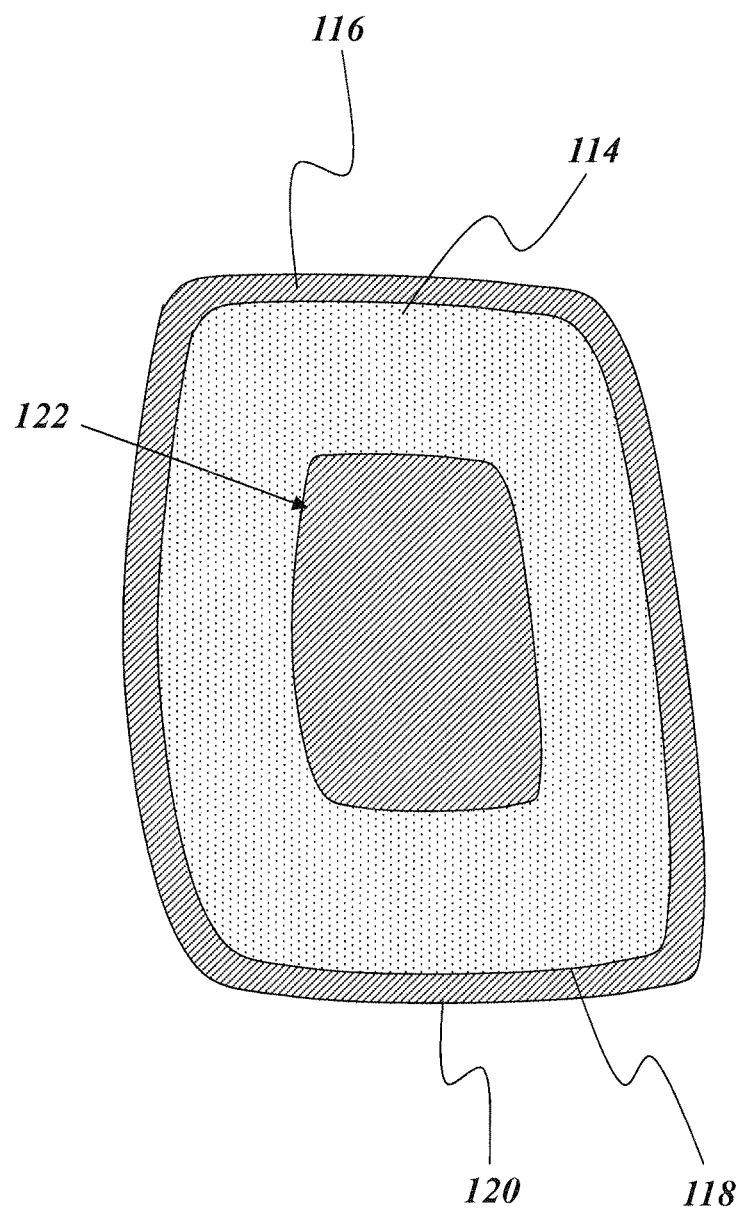
FIG. 9 depicts a perspective view of another example prosthesis, according to aspects of the present invention.
Figure 10A:
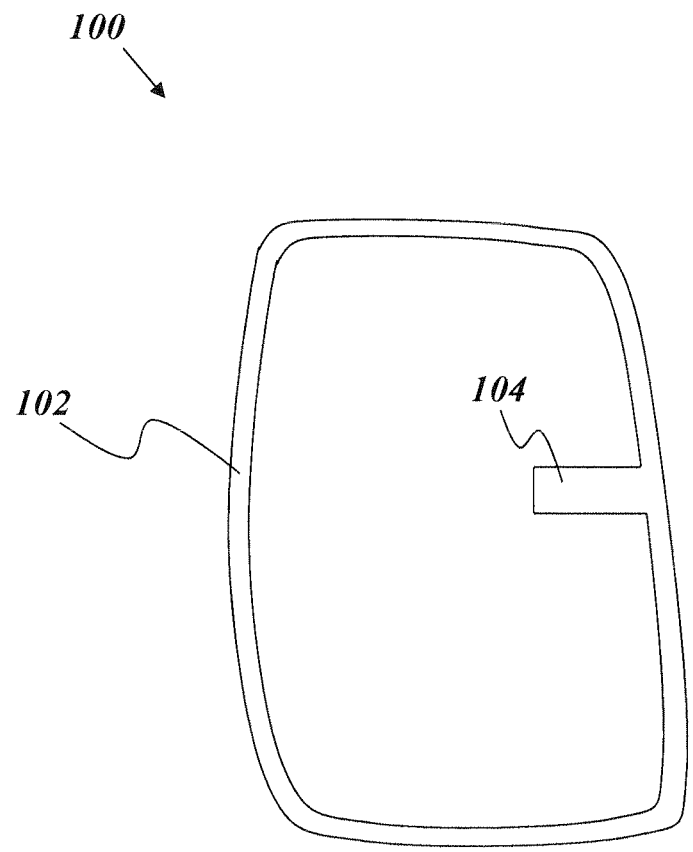
FIG. 10A depicts a perspective view of another example embodiment of a deployment device forming a framework and adapted for the example prosthesis of FIG. 9, according to aspects of the present invention.

For example, FIG. 9 depicts an additional example embodiment of the prosthesis 112, wherein the first layer 114 and the second layer 116 are both generally shaped as a rectangle (more specifically, a rectangle having rounded corners). The first layer 114 and the second layer 116 are adjoined and enable formation of an enclosure 124 therebetween, as with the example prosthesis 112 of FIGS. 2A through 2C. FIG. 10A depicts an illustrative embodiment of the deployment device 100 adapted for the prosthesis 112 of FIG. 10A. As illustrated, the deployment device 102 includes a framework having a generally rectangular shape (e.g., generally bulged rectangular shape or generally rectangular shape with rounded edges). The tab 104 is a protruding flap that extends from one side of the flexible support structure 102 toward another (e.g., opposite) side of the flexible support structure 102. The tab 102 can have a length sufficient to enable the tab 102 to be grasped and pulled for removal.

Figure 10B:
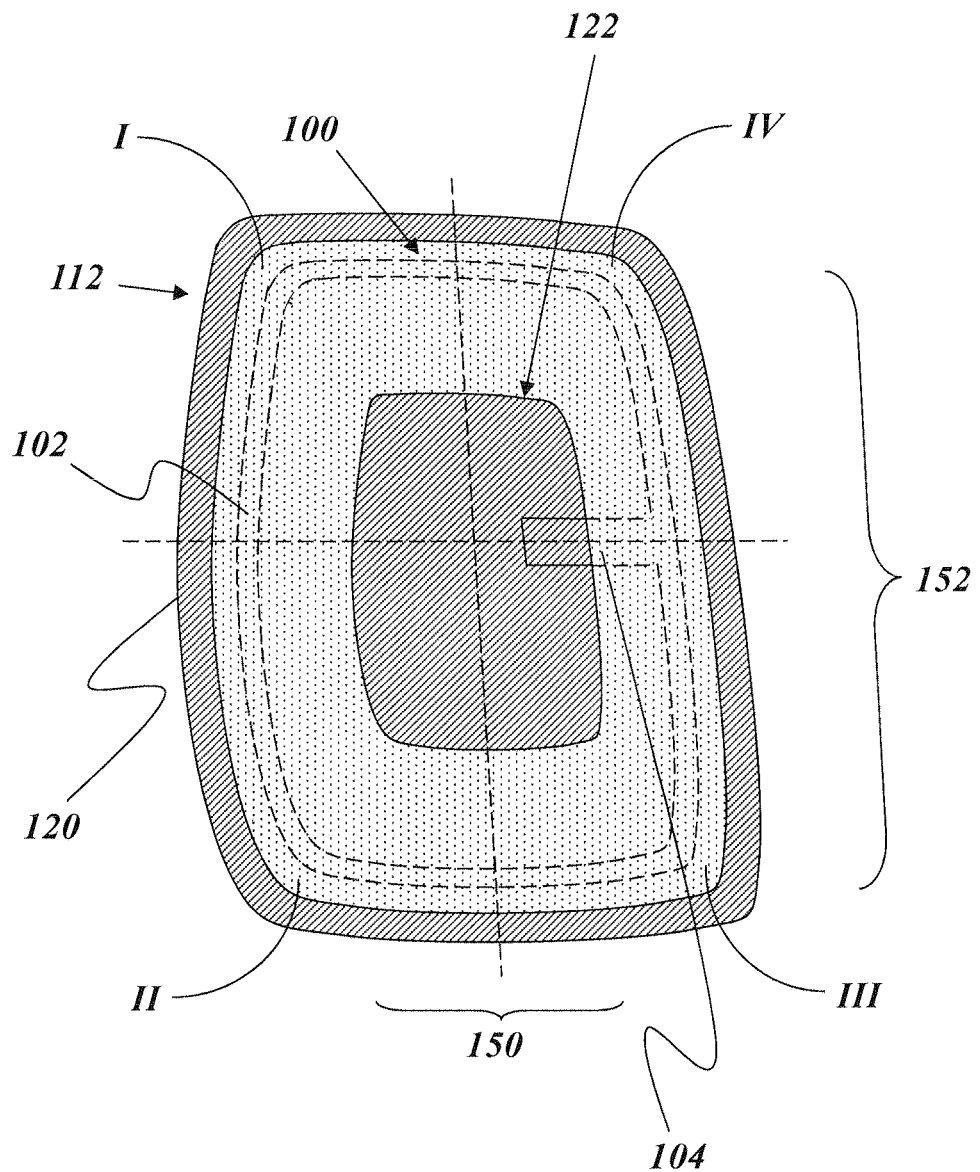
FIG. 10B depicts a perspective view of an example system including the example deployment device of FIG. 10A positioned in a deployed (e.g., generally planar) configuration in the example prosthesis of FIG. 9, according to aspects of the present invention.

FIG. 10B depicts the deployment device 100 of FIG. 10A placed in the prosthesis 112 of FIG. 9. As with the example embodiments of FIGS. 1A through 8, the one or more tabs 104 can extend external to the enclosure 124 (e.g., can protrude beyond an outer edge of the enclosure 124). Furthermore, the flexible support structure 102 extends into the enclosure 124 in at least one, in at least two, in at least three, or in all four of the substantially equal-area quadrants I, II, III, and IV into which the prosthesis 112 can be diagrammatically parsed. Furthermore, in illustrative embodiments, and as depicted in FIG. 10B, the flexible support structure 102 extends substantially to an outer perimeter of the prosthesis 112 (e.g., the outer perimeter 118 and/or the outer perimeter 120) at least once in at least two of the four quadrants I, II, III, and IV. In further illustrative embodiments, the flexible support structure 102 extends substantially to an outer perimeter of the prosthesis 112 (e.g., the outer perimeter 118 and/or the outer perimeter 120) at least once in at least three of the four quadrants I, II, III, and IV. In yet further illustrative embodiments, the flexible support structure 102 extends substantially to an outer perimeter of the prosthesis 112 (e.g., the outer perimeter 118 and/or the outer perimeter 120) at least once in all four of the four quadrants I, II, III, and IV.

The tab 104 can be located at a position on the flexible support structure 102 that divides a length 152 of the flexible support structure 102 in two equal halves, as depicted in FIG. 10B. Alternatively, the tab 104 can be located elsewhere on the flexible support structure 102. The tab 104 can extend across some percentage of a length 150 of the opening 122. As illustrative examples, the tab 104 can extend across about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% of the length 150 of the opening 122, or at another amount, e.g., which is sufficient to enable the tab 104 to be gripped for removal of the deployment device 100 from the prosthesis 112.

Figure 11A:
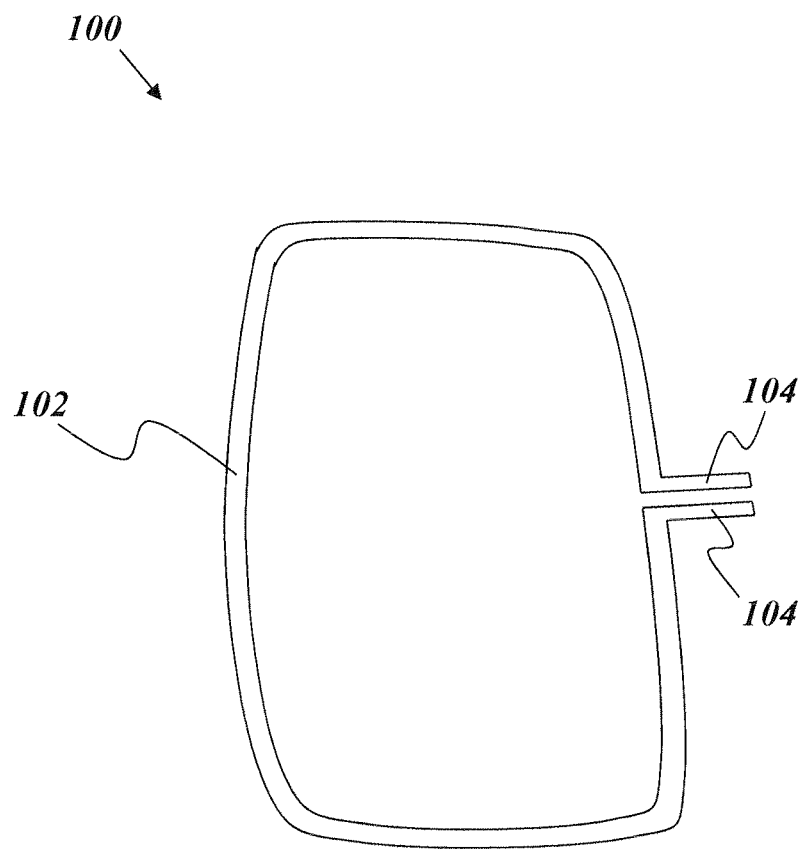
FIG. 11A depicts a perspective view of another example deployment device forming a framework and having two tabs each forming a protruding segment, according to aspects of the present invention.
Figure 11B:
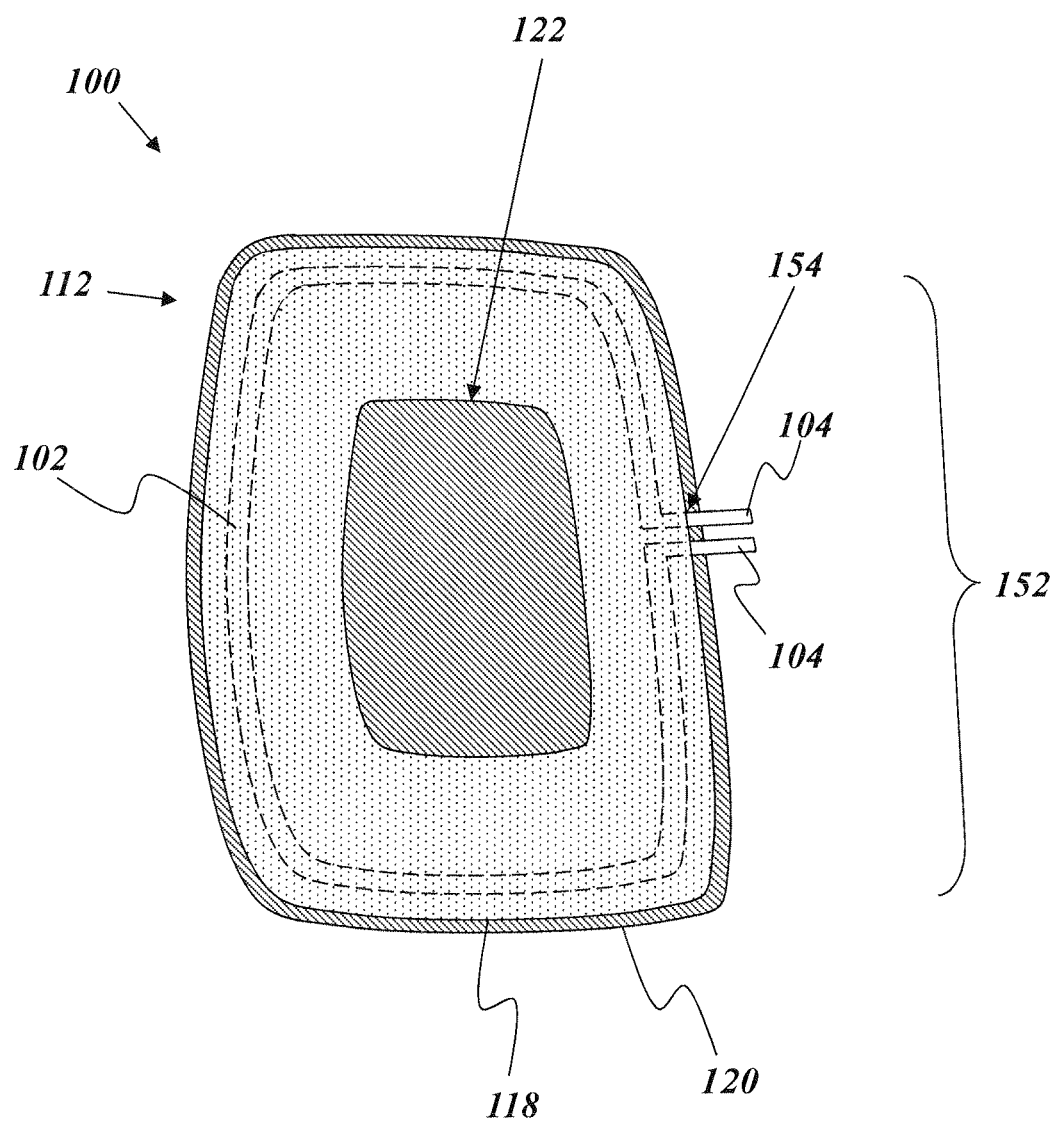
FIG. 11B depicts a perspective view of an example system including the example deployment device of FIG. 11A positioned in a deployed (e.g., generally planar) configuration in the example prosthesis of FIG. 9, according to aspects of the present invention.

Furthermore, although certain embodiments described and depicted herein provide that the one or more tabs 104 protrude through or beneath the opening 112, the tabs 104 alternatively or additionally can be configured to protrude through different openings disposed in and through other portions of the prosthesis 112. For example, FIG. 11A depicts an alternative embodiment of the deployment device 100, which includes two tabs 104 that are adjoined with the flexible support structure 102 and which extend from one or more connection points in an outward direction away from a center point of the flexible support structure 102, e.g., which extend beyond an outer edge of the flexible support structure 102. Each of the two tabs 104 in the example embodiment of FIG. 11A include a protruding segment that deviates from extends beyond the generally rectangular shape (as non-limiting examples, generally bulged rectangular shape, or generally rectangular shape with rounded edges) of the flexible support structure 102. FIG. 11B depicts the deployment device 100 disposed within the prosthesis 112. As can be seen from FIG. 11B, the tabs 104 extend transversally beyond an outer edge of the prosthesis 112.

Accordingly, the tabs 104 can extend through an opening 154 disposed in and through a side of the prosthesis 112. Although the opening 154 is not visible from the perspective view of FIG. 11B, the position of the opening 154 is referenced, for clarity. As just one non-limiting example, the opening 154 in the prosthesis 112 can be formed in stitching that connects the first layer 114 and the second layer 116. The tabs 104 can extend over the second layer 116, through the opening 154, and beyond the outer perimeter 120 of the second layer 116 (e.g., beyond the perimeter of the prosthesis 112), as illustrated in FIG. 11B. The opening 154 is further depicted from a side view in FIG. 11C.

As described previously with regard to the example embodiments of FIGS. 1A through 8, the size and/or orientation of the flexible support structure 102 can be different from the shape and/or size of the opening 154 through which the one or more tabs 104 extend. In illustrative embodiments, the flexible support structure 102 is larger in size (e.g., in one or more dimensions, in area, in volume occupied, or the like) than the opening 154. For instance, in some embodiments, the flexible support structure 102 has a length 152 that is greater than a length 158 of the opening 154. As another example, the flexible support structure 102, when positioned in the prosthesis 112 and when in a deployed (e.g., generally planar) configuration therein, can have a profile (as viewed from above, e.g., the top view of FIG. 3B) that includes at least one portion that is non-overlapping with a corresponding profile (as viewed from above) of the opening 112.

Furthermore, the opening 112 can have a total circumferential area that is less than a total circumferential area occupied by the flexible support structure 102 when the prosthesis 112 and the flexible support structure 102 are in the deployed (e.g., generally planar) configuration (as depicted in FIG. 3A). In further embodiments, the opening 154 can have a total circumferential area that is substantially less than the total circumferential area occupied by the flexible support structure 102 when the prosthesis 112 and the flexible support structure 102 are in the deployed (e.g., generally planar) configuration. In yet further embodiments, the opening 154 can have a total circumferential area that is significantly less than the total circumferential area occupied by the flexible support structure 102 when the prosthesis 112 and the flexible support structure 102 are in the deployed (e.g., generally planar) configuration. As some examples, and depending on the particular shape of the prosthesis 112, the flexible support structure 102 (when in a deployed, e.g., generally planar, configuration in the prosthesis 112) can have a total circumferential area that is about 5% more, about 10% more, about 15% more, about 20% more, about 25% more, about 30% more, about 35% more, about 40% more, about 45% more, about 50% more, about 55% more, about 60% more, about 65% more, about 70% more, about 75% more, about 80% more, about 85% more, about 90% more, about 95% more, about 100% more, about 105% more, about 110% more, about 115% more, about 120% more, about 125% more, about 130% more, about 135% more, about 140% more, about 145% more, about 150% more, about 155% more, about 160% more, about 165% more, about 170% more, about 175% more, about 180% more, about 185% more, about 190% more, or about 195% more, about 200% more, or greater than about 200% more (or some intermediate value lying therebetween) than a total circumferential area occupied by the opening 122.

Figure 11C:
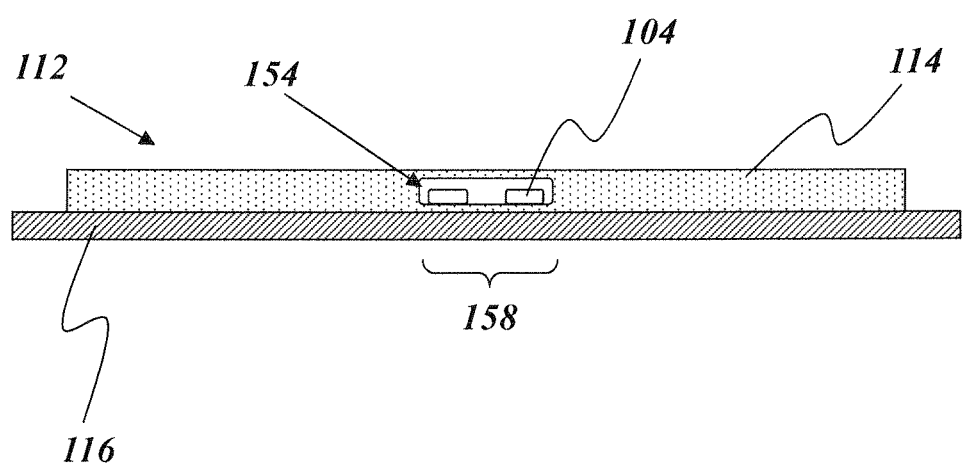
FIG. 11C depicts a side view of the example system of FIG. 11B when in the deployed (e.g., generally planar) configuration, according to aspects of the present invention.
Figure 11D:
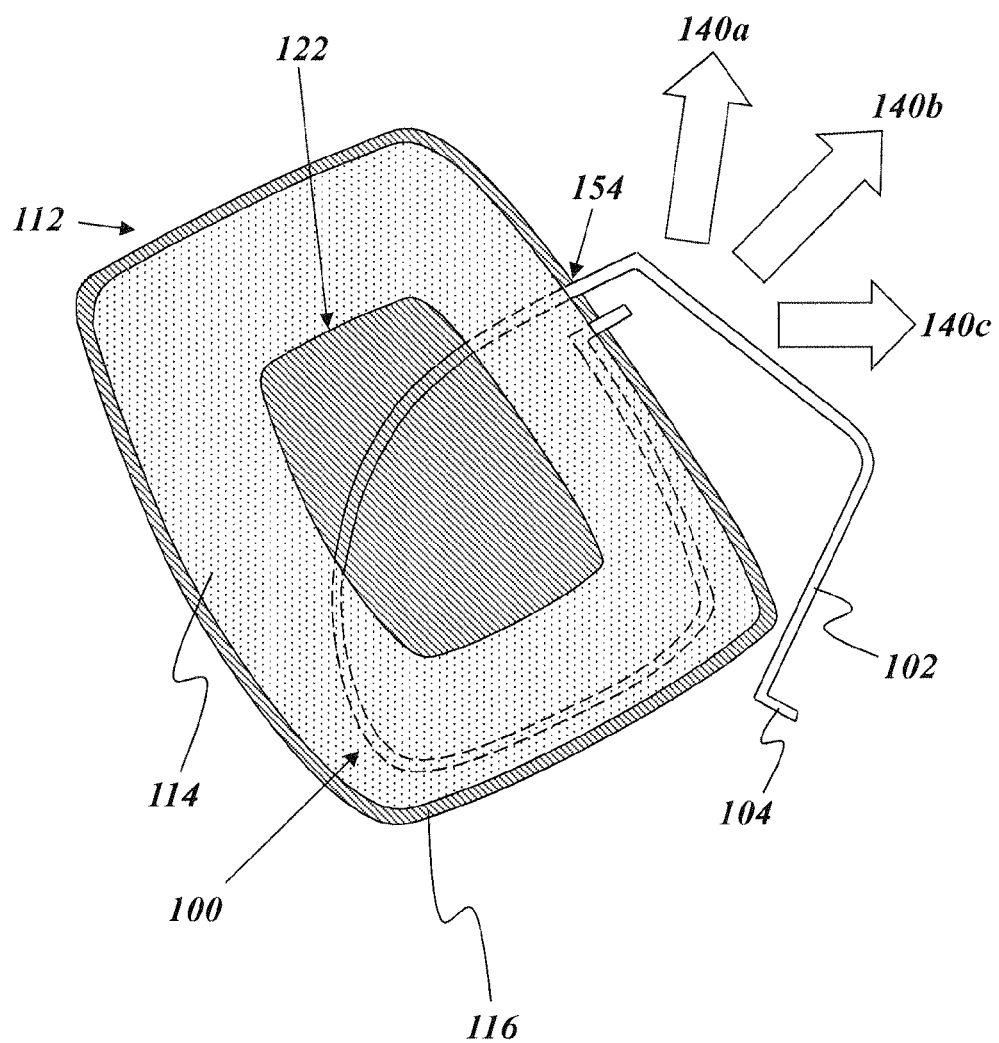
FIG. 11D depicts a perspective view of the example system of FIG. 11B during removal of the example deployment device from the example prosthesis, according to aspects of the present invention.

FIG. 11D depicts the deployment device 100 of FIGS. 11A through 11C during removal from the prosthesis 112 through the opening 154. As illustrated, the flexible support structure 102 can assume a collapsed configuration, e.g., which includes at least one bend, fold, or other collapsed state. The collapsed configuration can allow the flexible support structure 102 to pass through the opening 154 and thereby retreat from the enclosure 124. As with the embodiments of FIGS. 1A through 8, removal of the deployment device 100 can result in an enlargement of the enclosure 124, which can be caused by pulling one or both of the tabs 104 in a direction away from the prosthesis 112. As non-limiting examples, the reconfiguration (e.g., in shape, orientation, or both) of the flexible support structure 102 can be caused by pulling one of the tabs 104 in any one of example directions 140*a*, 140*b*, 140*c*, or in another direction away from the prosthesis 112.

Figure 12A:
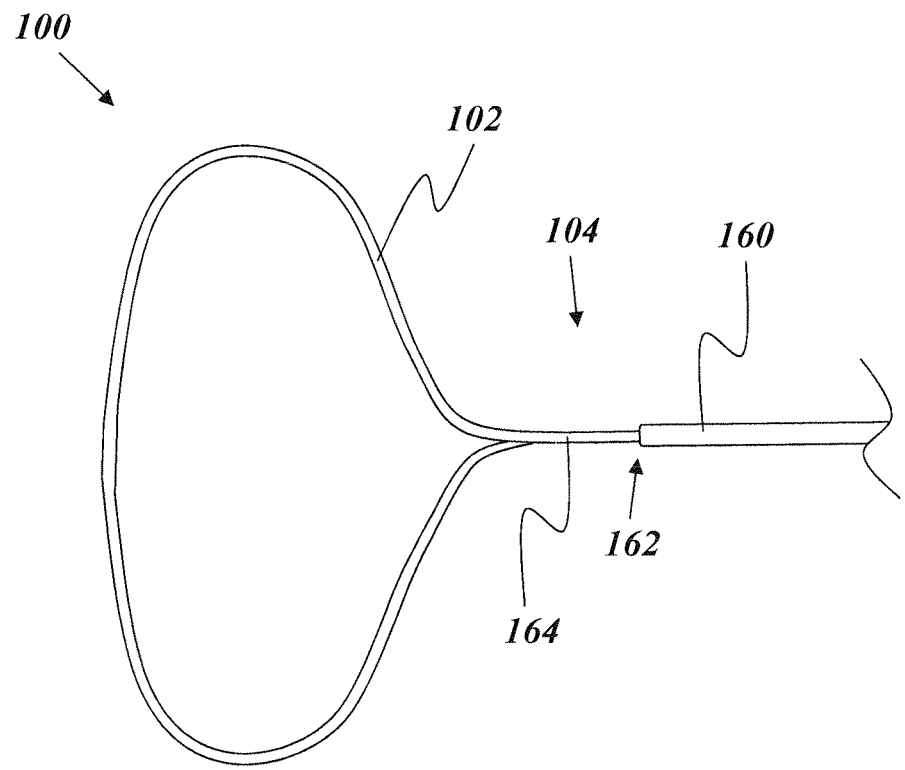
FIG. 12A depicts a top view of another example deployment device forming a framework and including an insertion device, according to aspects of the present invention.

Still other embodiments are possible. For example, the tab 104 can include one or more additional components, such as an insertion device, a positioning device, or another device or component. FIG. 12A depicts the deployment device 100 according to an additional embodiment of the present invention, wherein the tab 104 includes a protruding portion 164 and an insertion device 160. For instance, the insertion device 160 can be an elongate, generally tubular, hollow rod inside which the flexible support structure 102 (and the protruding portion 164) can be movably positioned. The insertion device 160 can be coupled to or otherwise joined with the deployment device 100 (e.g., at the tabs 104, on some portion of the flexible support structure, on additional slack that remains within the insertion device 160, etc.). The insertion device 160 can be constructed from metal, plastic, or any other suitable material.

Figure 12B:
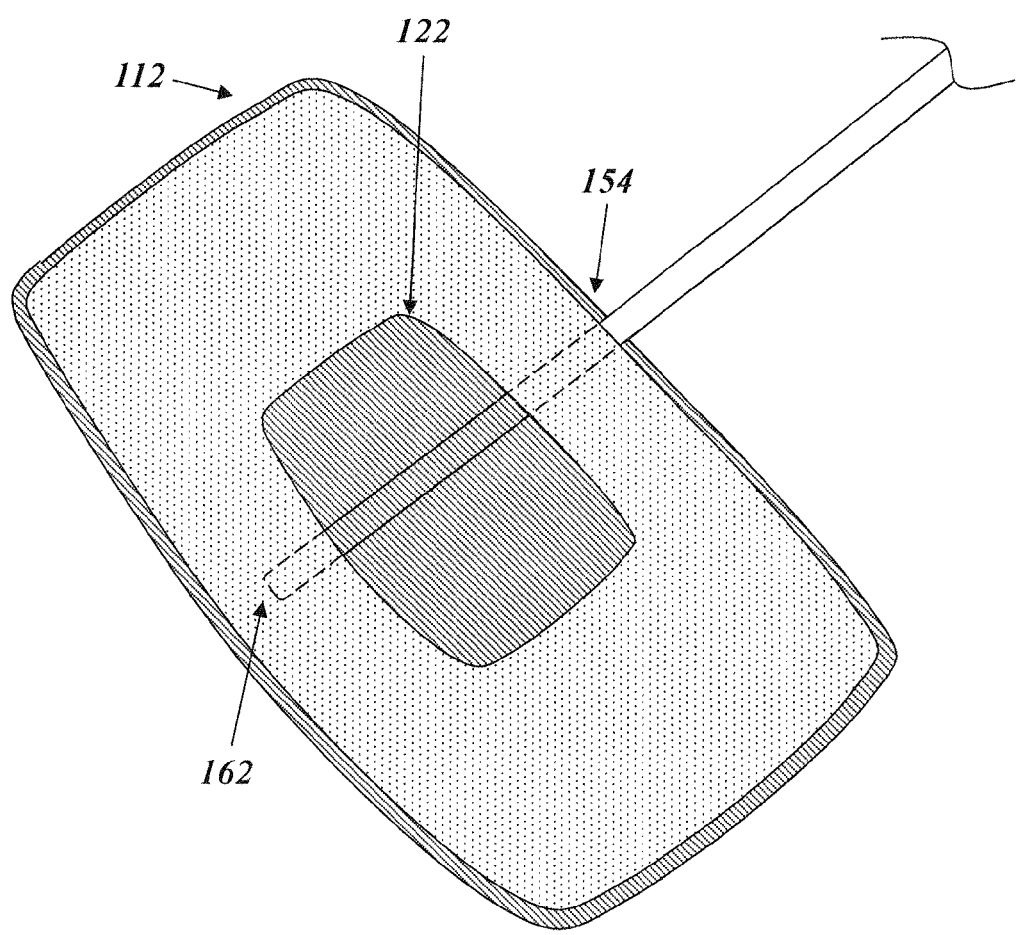
FIG. 12B depicts a perspective view of an example system including the example deployment device of FIG. 12A inserted in a non-deployed (e.g., rolled up or non-planar) configuration in the example prosthesis of FIG. 9, according to aspects of the present invention.

As illustrated in FIG. 12B, the insertion device 160 can be inserted into the prosthesis 112 through the opening 154, e.g., along with the flexible support structure 102 contained therein but unexposed at an open distal end 162. Once positioned appropriately (for instance, across at least the entire width of the opening 122), the insertion device 160 can be removed through the opening 154 so that it is no longer positioned in the prosthesis 112, thereby enabling the flexible support structure 102 to assume a deployed (e.g., generally planar) configuration, as depicted in the example deployed (e.g., generally planar) configuration of FIG. 12C. Once the prosthesis 112 is suitably affixed or implanted at a target site of an anatomical defect, the tab 104 (e.g., the insertion device 160 and/or the protruding portion 164) can be pulled in a direction away from the prosthesis 112, thereby enabling reconfiguration of the flexible prosthesis 102 and removal of the deployment device 100.

Alternatively, the insertion device 160 can be unconnected to and initially separate from the deployment device 100. For example, the insertion device 160 can be inserted into the prosthesis 112 prior to placing the deployment device 100 therein. Once the insertion device 160 is inserted and properly positioned in the prosthesis 112, a surgeon or other operator handling the deployment device 100 can "feed" the deployment device 100 through the insertion device 160 such that it moves through the tubular length of the insertion device 160 and out the open distal end 162. Simultaneously or subsequently, the insertion device 160 can be pulled away and removed from the prosthesis 112, thereby exposing the flexible support structure 102 and enabling it to assume a deployed (e.g., generally planar) configuration. Once prepared for removal, the protruding portion 164 of the tab 104 can be used to cause the deployment device 100 to reconfigure in order to retreat from the enclosure 124 of the implanted prosthesis 112.

Figure 12C:
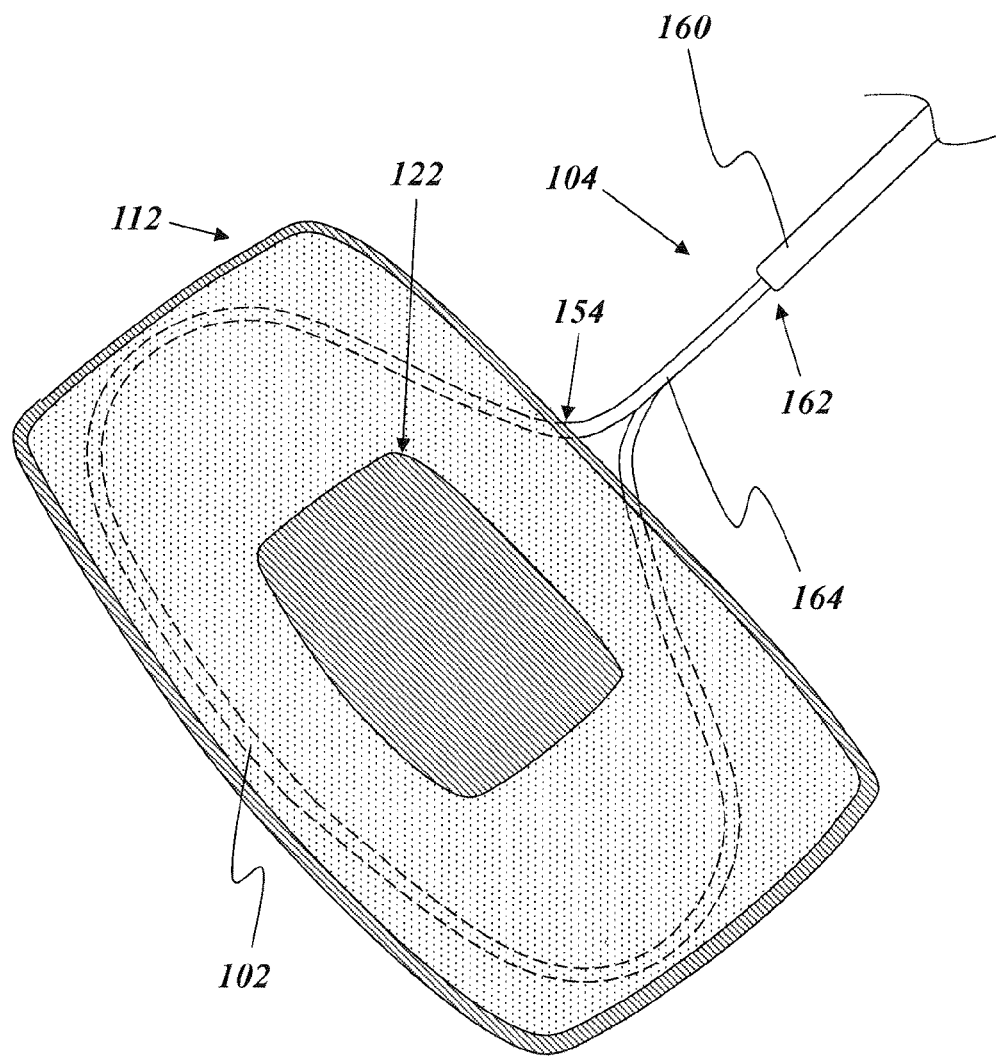
FIG. 12C depicts a perspective view of the example system of FIG. 12B in a deployed (e.g., generally planar) configuration, according to aspects of the present invention.

Furthermore, the insertion device 160 additionally can serve as a tool for inserting the prosthesis 112. For example, once the insertion device 160 is positioned as depicted in FIG. 12B (e.g., with the flexible support structure 102 contained within the insertion device 160), the prosthesis 112 can be wrapped around the insertion device 160. Next, the insertion device 160, along with the prosthesis 112 wrapped therearound, can be inserted into a body at the target site of the anatomical defect. The prosthesis 112 can be allowed to unroll at the target site, and the insertion device 160 can be pulled away and removed from the prosthesis 112, as depicted in FIG. 12C. In some instances, the insertion device 160 can remain in the prosthesis 112 at a perimeter of the enclosure 124 while the flexible support structure 102 is deployed. This can be beneficial in ensuring that the flexible support structure 102 fully deploys in the prosthesis 112.

Accordingly, for these and other embodiments, the flexible support structure 102 further can be sufficiently flexible to assume a collapsed configuration sufficient for insertion into the body, e.g., with an insertion, positioning, or other device.

Figure 13:
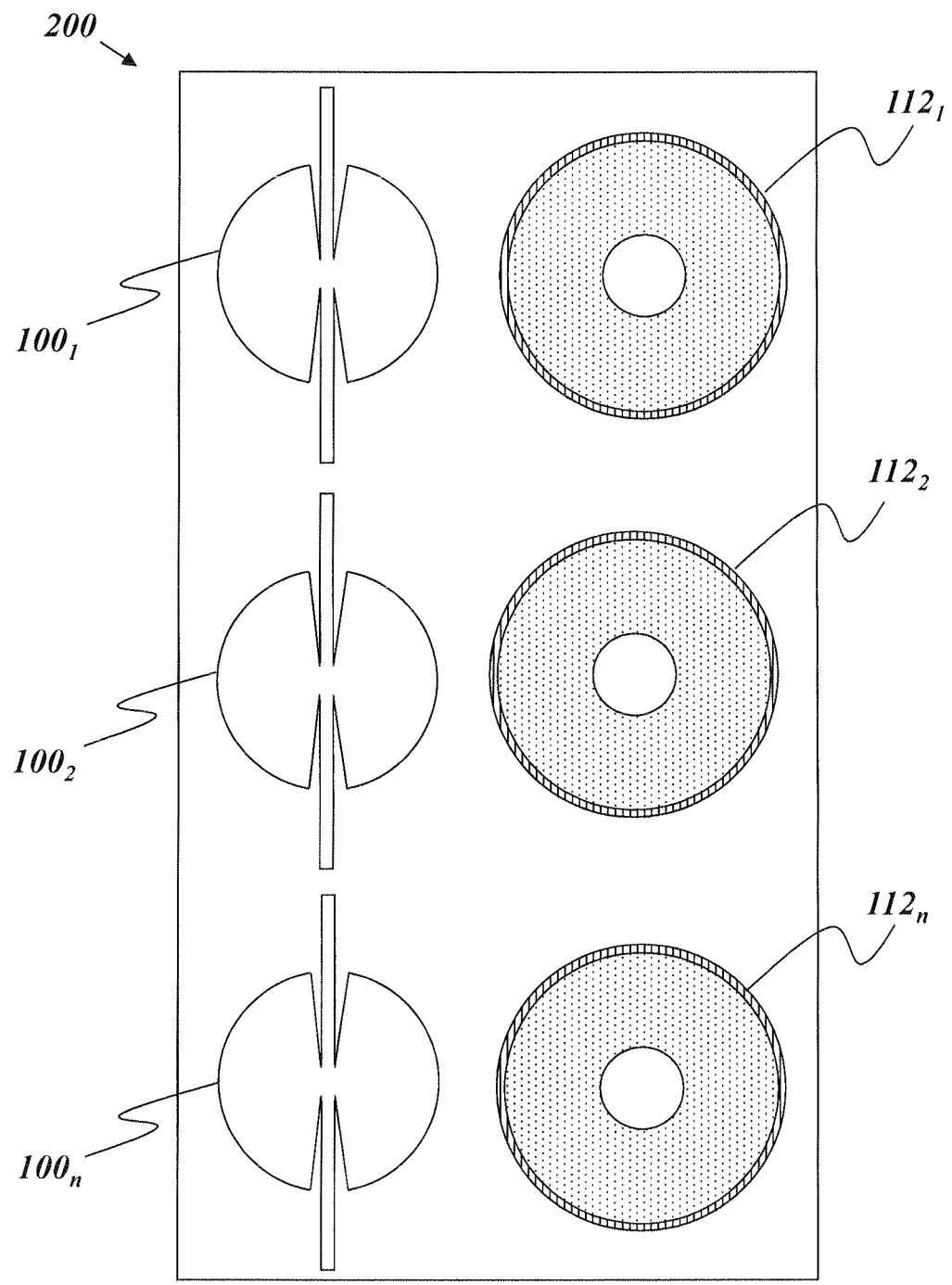
FIG. 13 depicts a kit according to embodiments of the present invention.

Furthermore, prostheses and deployment devices, according to embodiments described and depicted herein, can be packaged and sold in kits. For example, kits according to some embodiments of the present invention each include one or more deployment devices each being inserted into a prosthesis, e.g., in a rolled or other collapsed configuration, or alternatively in a non-collapsed configuration. In other embodiments of the present invention, the kits each can include one or more prostheses and one or more deployment devices that are not inserted into the one or more prostheses. For example, such a kit 200 is depicted in FIG. 13. One of skill in the art will appreciate that there is no limit on the number of deployment devices 100 and prostheses 112 that are included in the kit 200. For example, the kit 200 can include a first prosthesis $112_1$, a second prosthesis $112_2$, up through an nth prosthesis $112_n$. Similarly, the kit 200 can include a first deployment device $100_1$, a second deployment device 1002, up through an nth deployment device $100_n$. The number of prostheses 112 and deployment devices 100 in the kit 200 need not be the same. Furthermore, as alternatives, one or both of the prosthesis 112 and the deployment device 102 can be packaged and/or sold separately.

Figure 14:
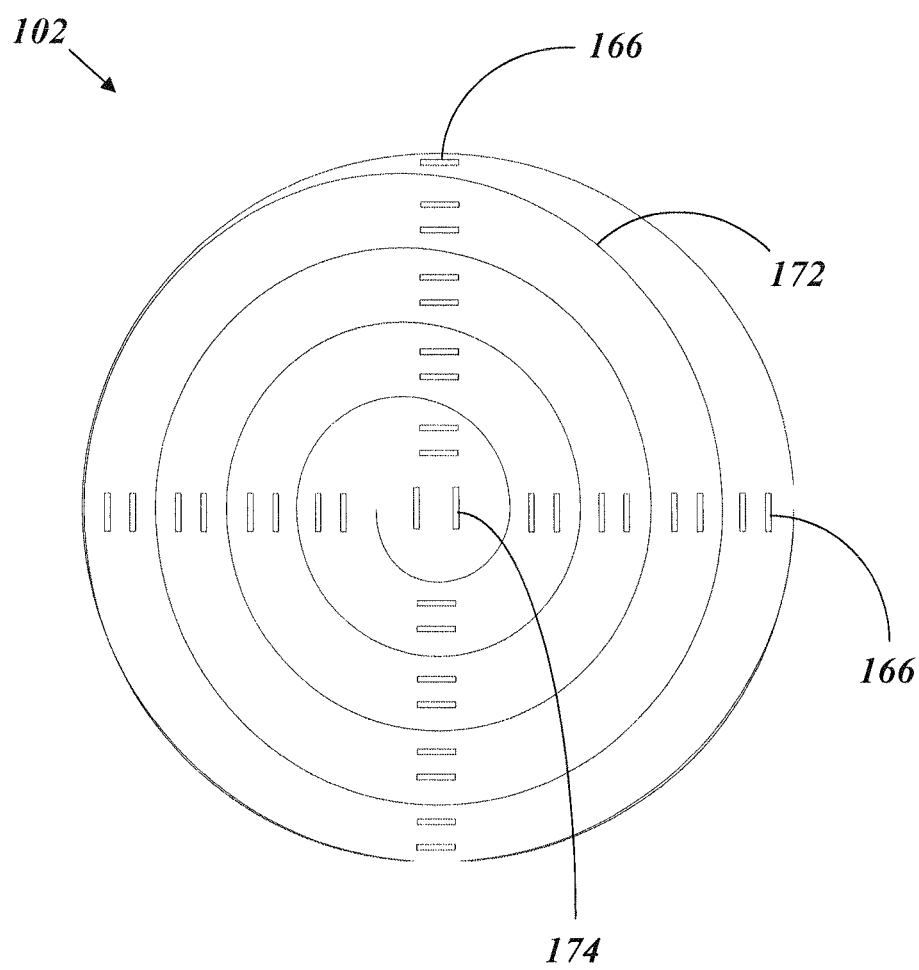
FIG. 14 depicts a top view of a flexible support structure having a serpentine separation line extending from an inner portion thereof to a perimeter thereof, according to embodiments of the present invention.

Still other embodiments are possible. FIG. 14 depicts an example embodiment of a flexible support structure 102 having a serpentine configuration. In particular, the flexible support structure 102 includes a serpentine edge 172. A "serpentine edge" herein refers to an arrangement of one or more connected edges that extend from an inner (e.g., central) portion of the flexible support structure 102 to one or more points on the perimeter of the flexible support structure 102. In illustrative embodiments, the serpentine edge 172 sweeps out a full 360 degrees (e.g., by making at least one complete revolution). Furthermore, in illustrative embodiments, the serpentine edge 172 is a spiral edge. As depicted in FIG. 14, the serpentine edge 172 includes an inner end proximate to the center of the flexible support structure 102 and an outer end at a point on the perimeter of the flexible support structure 102. Abutting portions of the flexible support structure 102 along the serpentine edge 172 are discontinuous and physically unconnected along the serpentine edge 172. The discontinuous and physically unconnected portions formed by the serpentine edge 172 are held in place by a removable connector piece.

Figure 15:
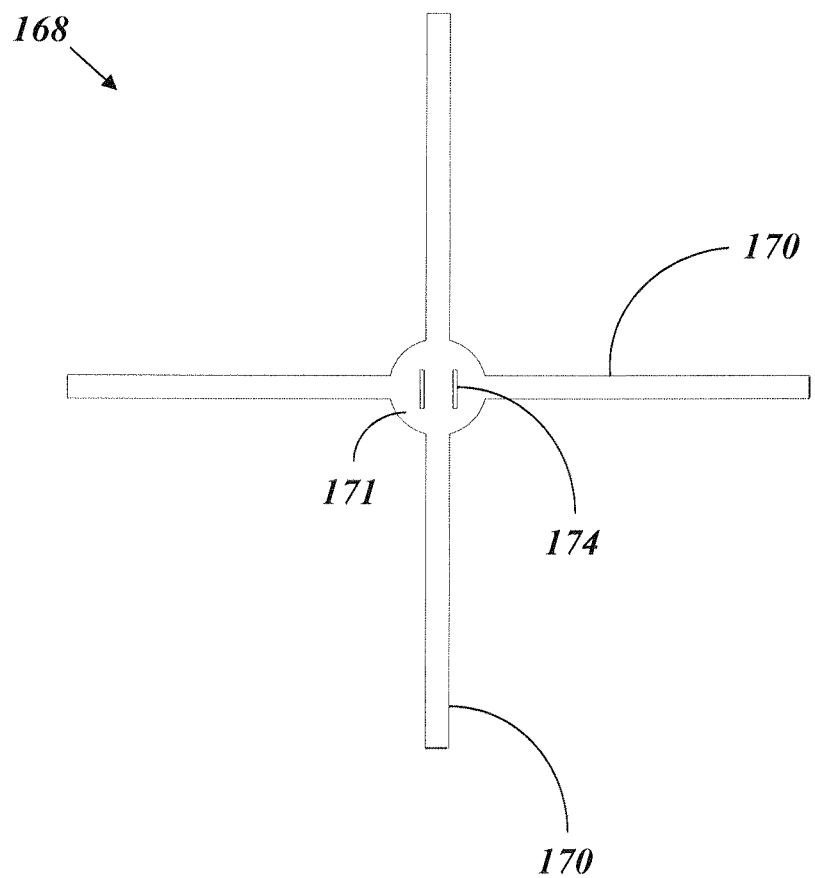
FIG. 15 depicts a removable connector piece for operationally adjoining portions of the flexible support structure of FIG. 14 along the serpentine separation line, according to aspects of the present invention.

For example, FIG. 15 depicts an illustrative embodiment of such a removable connector piece 168, which includes four rectangular elongate portions 170 adjoined at a central portion 171 and forming a cross-like shape. In some embodiments, the removable connector piece 168 includes a protective film that is not easily penetrated by tacks or sutures. For example, the protective film can be a component that is independent from the removable connector piece 168 and that slips over the removable connector piece 168 prior to insertion into the flexible support structure 102. This can be useful in providing protective measures that aid in preventing unintentional fixation by a surgeon at undesirable positions (e.g., on the deployment device 100 and/or a patient's viscera). The protective film can include two slits that are aligned (positioned in-line) with the strap slots 174. Accordingly, the protective film can be positioned over (e.g., slid over) the strap 176 and the additional strap 182 such that both the strap 176 and the additional strap 182 pass through the protective film.

Continuing with the example embodiment of FIG. 14, the flexible support structure 102 can include a plurality of slits 166 (e.g., relatively thin openings) in its surface for receiving the removable connector piece 168, e.g., in a threaded (repeating over-and-under) fashion. Accordingly, the slits 166 can be arranged in a straight line as depicted in FIG. 14, so as to ease in the removal of the removable connector piece 168 therefrom.

One of skill in the art will appreciate that other receiving mechanisms besides the slits 166 can be included for receiving (e.g., releasably) the removable connector piece 168. For example, as additions or alternatives to the slits 166, the flexible support structure 102 can include loops, straps, large openings, and any other suitable receiving mechanism. Furthermore, the slits 166 or alternative receiving mechanisms can be arranged in other shapes and configurations besides the straight lines depicted in FIG. 14. In some embodiments, only one such slit 166 or receiving mechanism is included, rather than the plurality depicted in FIG. 14. Furthermore, one of skill in the art will readily appreciate that other mechanisms having different shapes can be included as alternatives or additions to the elongate portions 170. Additionally, the number of elongate portions 170 or equivalent mechanisms included in the removable connector piece 168 can be different from the embodiment depicted in FIG. 15. For example, the removable connector piece 168 can include one, two, three, four, five, six, etc. appendages or distinctly shaped portions. One of skill in the art will appreciate yet other alternatives upon reading the present specification. The present invention is not limited to the illustrative examples provided herein. All alternatives and modifications are contemplated within the scope of the present invention.

The flexible support structure 102 and the removable connector piece 168 each can include one or more strap slots 174 for enabling one or more strap components to fit therethrough. In the illustrative embodiment of FIG. 14, each of the flexible support structure 102 and the removable connector piece 168 includes two such strap slots 174. However, more or less strap slots 174 can be included therein. The strap slots 174 can be any suitable openings sized to receive one or more straps. The strap slots 174 can be positioned on both the flexible support structure 102 and the removable connector piece 168 such that placing the removable connector piece 168 atop the flexible support structure 102 and aligning the center points of the removable connector piece 168 and the flexible support structure 102 also results in the strap slots 174 being aligned, e.g., to form a through-opening. Accordingly, in this manner, the strap slots 174 on the flexible support structure 102 can have the same positions on the flexible support structure 102 as on the strap slots 174 on the removable connector piece 168.

Figure 16A:
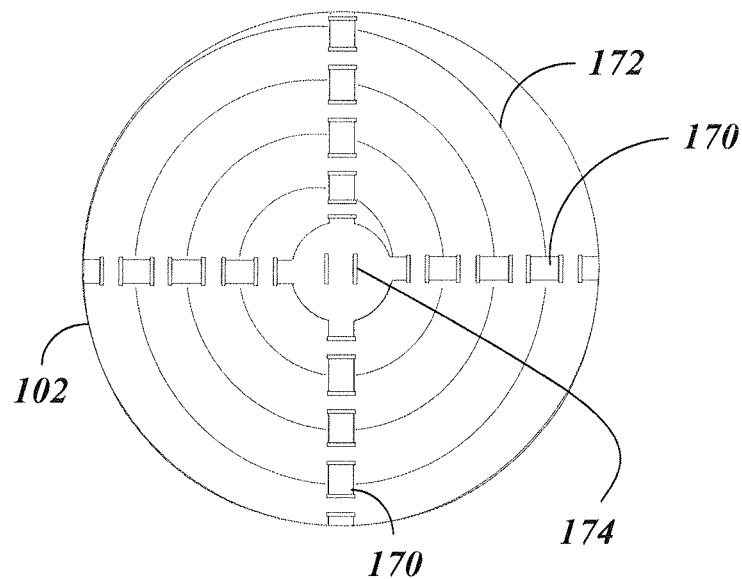
FIG. 16A depicts a top view of the flexible support structure of FIG. 14 with the removable connector piece of FIG. 15 situated therein, according to embodiments of the present invention.
Figure 16B:
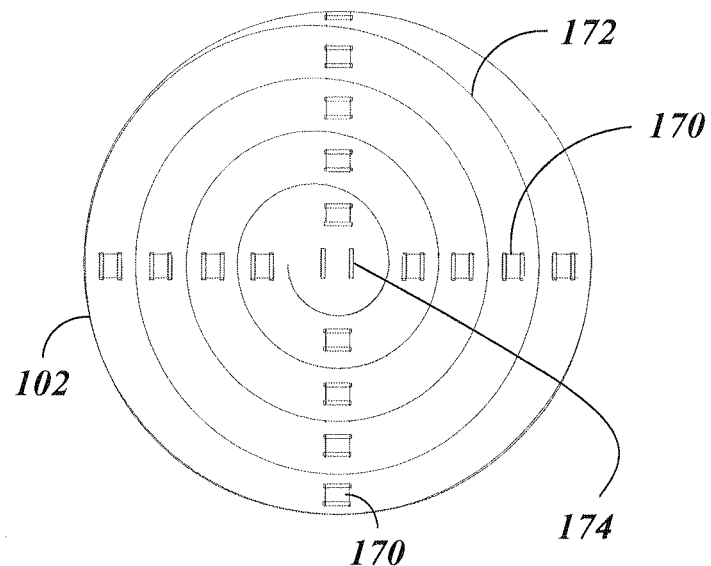
FIG. 16B depicts a bottom view of the flexible support structure of FIG. 14 with the removable connector piece of FIG. 15 situated therein, according to embodiments of the present invention.

FIGS. 16A and 16B depict a top view and a bottom view, respectively, of the removable connector piece 168 of FIG. 15 threaded in the slits 166 of the flexible support structure 102 of FIG. 14. As depicted, the elongate portions 170 pass successively through the slits 166, thereby forming in an alternating pattern of visibility on each side of the flexible support structure 102. The removable connector piece 168 has a stiffness that is sufficient to maintain the positions of abutting portions of the flexible support structure 102 along the serpentine edge 172 (e.g., prevent folding and overlap of the abutting portions), thereby structurally reinforcing the flexible support structure 102 and providing it with suitable deployment characteristics. In the illustrative embodiment of FIG. 15, the removable connector piece 168 further is sufficiently flexible to allow the removable connector piece 168 to bend so that it may be received by the flexible support structure 102 and removed therefrom.

In addition, FIGS. 16A and 16B illustrative that the strap slots 174 of the flexible support structure 102 and of the removable connector piece 168 align when the removable connector piece 168 is received by the flexible support structure 102. Said differently, the strap slots 174 of the flexible support structure 102 overlap with the strap slots 174 of the removable connector piece 168. Thus, one or more straps are enabled to easily pass through the overlapping strap slots 174 of FIGS. 16A and 16B, thereby passing through both the flexible support structure 102 and the removable connector piece 168.

Figure 17:
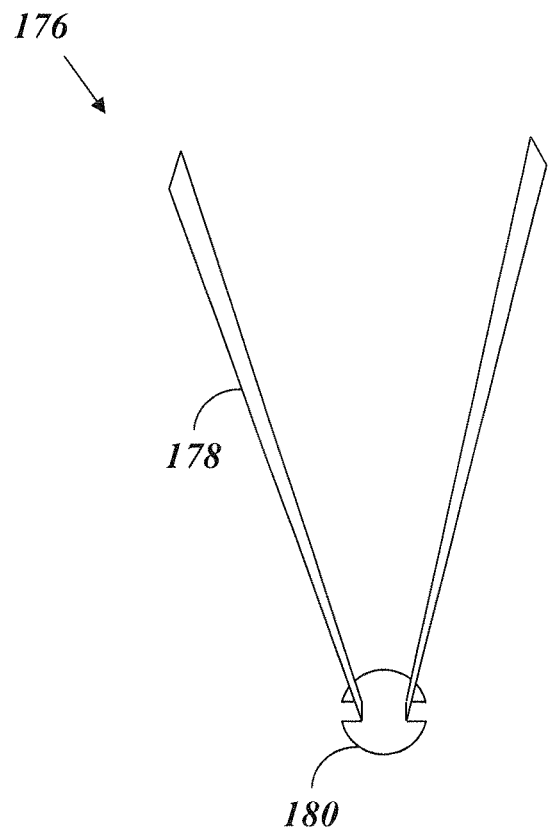
FIG. 17 depicts a perspective view of a strap for use in removing the flexible support structure FIGS. 16A and 16B, according to aspects of the present invention.

For example, FIG. 17 depicts a strap 176 that includes two strap appendages 178 and a strap base 180. The strap appendages 178 are sized to fit through the strap slots 174 of both the flexible support structure 102 and the removable connector piece 168. When received by the strap slots 174 of the flexible support structure 102 and the removable connector piece 168, the strap base 180 sits below a central portion of the flexible support structure 102. Accordingly, the strap appendages 178 are included to facilitate removal of the flexible support structure 102 from a prosthesis, such as the prosthesis 112 of FIG. 2A through 2C. Similar to the methods described previously herein, pulling the strap 176 (e.g., pulling the strap appendages 178) in a direction away from the prosthesis 112 causes the strap base 180 to produce an upward force against the center of the flexible support structure 102, which causes the flexible support structure 102 to be removed by contacting the mouth of the opening 122 and reconfiguring into a shape enabling its passage through the opening 122.

Figure 18:
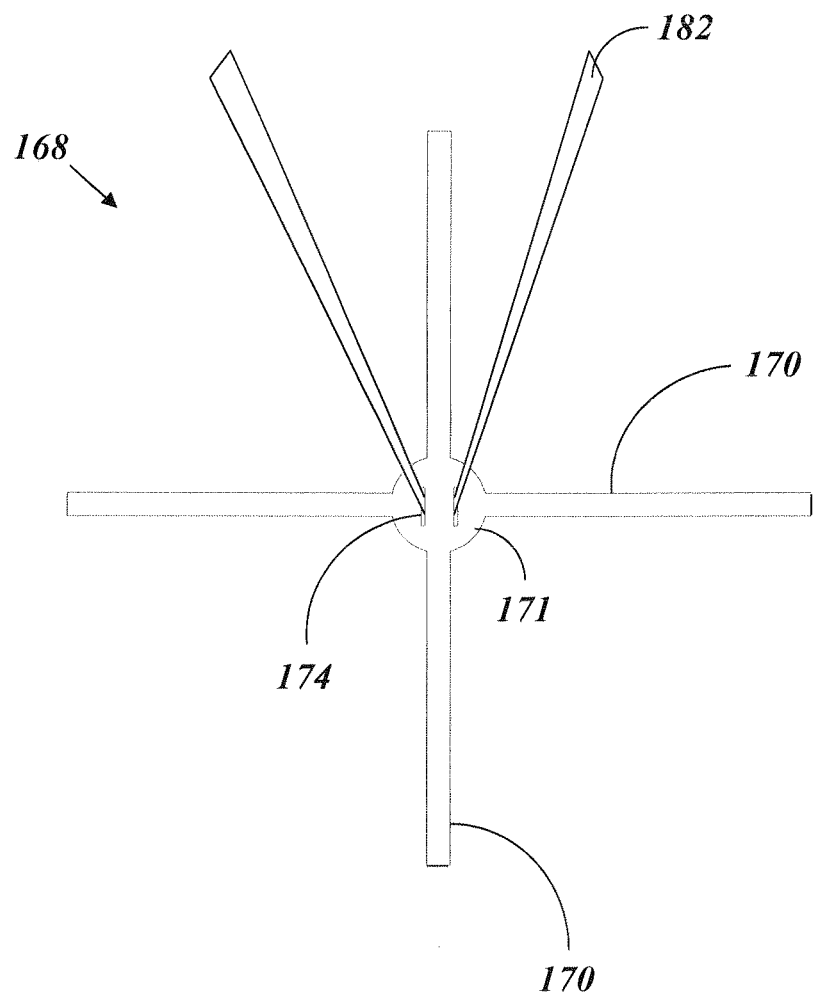
FIG. 18 depicts the removable connector piece of FIG. 15 with an additional strap for use in removal of the removable connector piece from the flexible support structure of FIG. 15, according to aspects of the present invention.

For the flexible support structure 102 to reconfigure into a shape suitable for passage through the opening 122 of the prosthesis 112, the removable connector piece 168 first must be removed. Accordingly, in addition to the strap 176, one or more additional straps can be coupled to or received by the removable connector piece 168 to facilitate removal of the removable connector piece 168. For example, FIG. 18 depicts an additional strap 182 that includes a continuous elongate member (e.g., formed of a single piece of material) passing through a first strap slot 174, passing below the central portion 171 of the removable connector piece 168, and passing through a second strap slot 174. For embodiments such as that depicted in FIG. 18 where the additional strap 182 passes through the strap slots 174 of the removable connector piece 168, the additional strap 182 does not pass through the strap slots 174 of the flexible support structure 102. Said differently, the additional strap 182 for enabling the removable connector piece 168 to be removed from the flexible support structure 102 is not received by the flexible support structure 102. Accordingly, gripping the additional strap 182 on each end and pulling upward causes the removable connector piece 168 to retreat from the slits 166 and bend in manner enabling its removal from the flexible support structure 102.

The task of removing the removable connector piece 168 is performed without causing the flexible support structure 102 to be removed from the prosthesis 112. This is due to the removable connector piece 168 being provided with a suitable elasticity and flexibility and the fact that the additional strap 182 is not received by the flexible support structure 102. In addition, the removable connector piece 168 and the flexible support structure 102 each can be constructed from a material having a low coefficient of friction. For example, in some embodiments, the removable connector piece 168 and the flexible support structure 102 both are constructed from extruded polyester, polyethylene, or polypropylene, e.g., with smooth surface finishes.

The portion of the additional strap 182 of FIG. 18 passing beneath the central portion 171 of the removable connector piece 168 can be affixed (e.g., with adhesive, stitching, etc.) to the underside of the removable connector piece 168. Alternatively, the additional strap 182 can be slidable through the strap slots 174 of the removable connector piece 168. In alternative embodiments, the additional strap 182 is not adjoined to the removable connector piece 168 via the strap slots 174 and does not pass through the strap slot 174. Instead, in such alternative embodiments, the removable connector piece 168 can be affixed (e.g., as two separate strap appendages) to the upward-facing surface of the removable connector piece 168. In yet another embodiment, the additional strap 182 includes a single strap appendage adjoined with the removable connector piece at its center. One of skill in the art will appreciate a wide variety of other suitable ways and positions at which to adjoin the additional strap 182 with the removable connector piece 168. The present invention is not limited to the illustrative examples described herein. Rather, all such alternatives and modifications are contemplated as within the scope of the present invention.

Figure 19A:
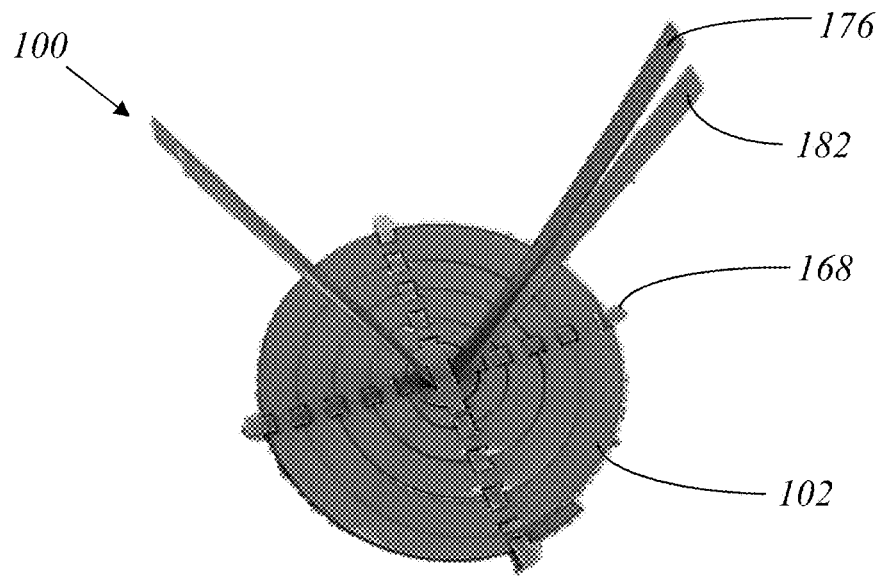
FIG. 19A depicts a top perspective view of a deployment device incorporating the components of FIGS. 14 through 18, according to aspects of the present invention.
Figure 19B:
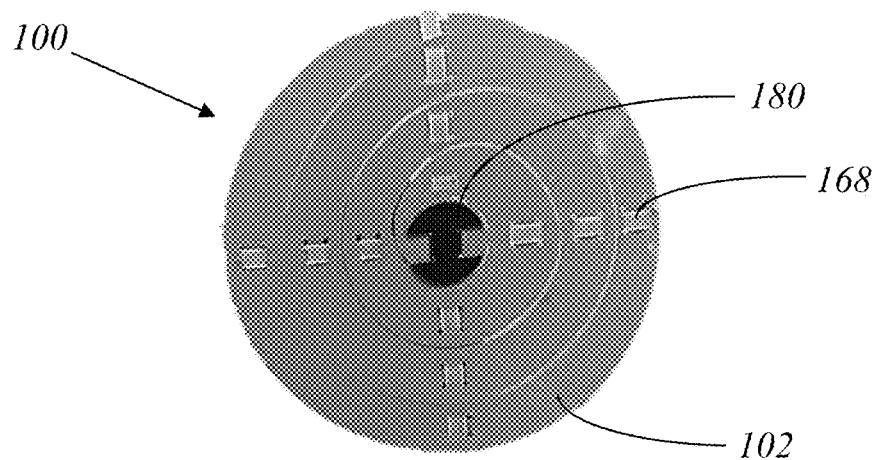
FIG. 19B depicts a bottom perspective view of the deployment device of FIG. 19A, according to embodiments of the present invention.

FIGS. 19A and 19B depict a perspective view and a bottom view, respectively, of the deployment device 100 including the components depicted in FIGS. 14 through 18. Specifically, the deployment device 100 of FIGS. 19A and 19B includes: (a) the flexible support structure 102 of FIG. 14, (b) the removable connector piece 168 of FIG. 15 threaded through the slits (as depicted in FIGS. 16A and 16B), (c) the strap 176 of FIG. 17 received through the strap slots 174 of both the flexible support structure 102 and the removable connector piece 168, and (d) the additional strap 182 of FIG. 18 received by the strap slots 174 of the removable connector piece 168 (and not received by the strap slots 174 of the flexible support structure 102). In such embodiments, the strap 176 forms the tab 104. Accordingly, the tab 104 is received by the flexible support structure 102 rather than affixed to the flexible support structure 102. However, it should be appreciated that the strap 176 alternative can be affixed to the flexible support structure 102 in the example embodiment of FIGS. 19A and 19B.

Figure 20:
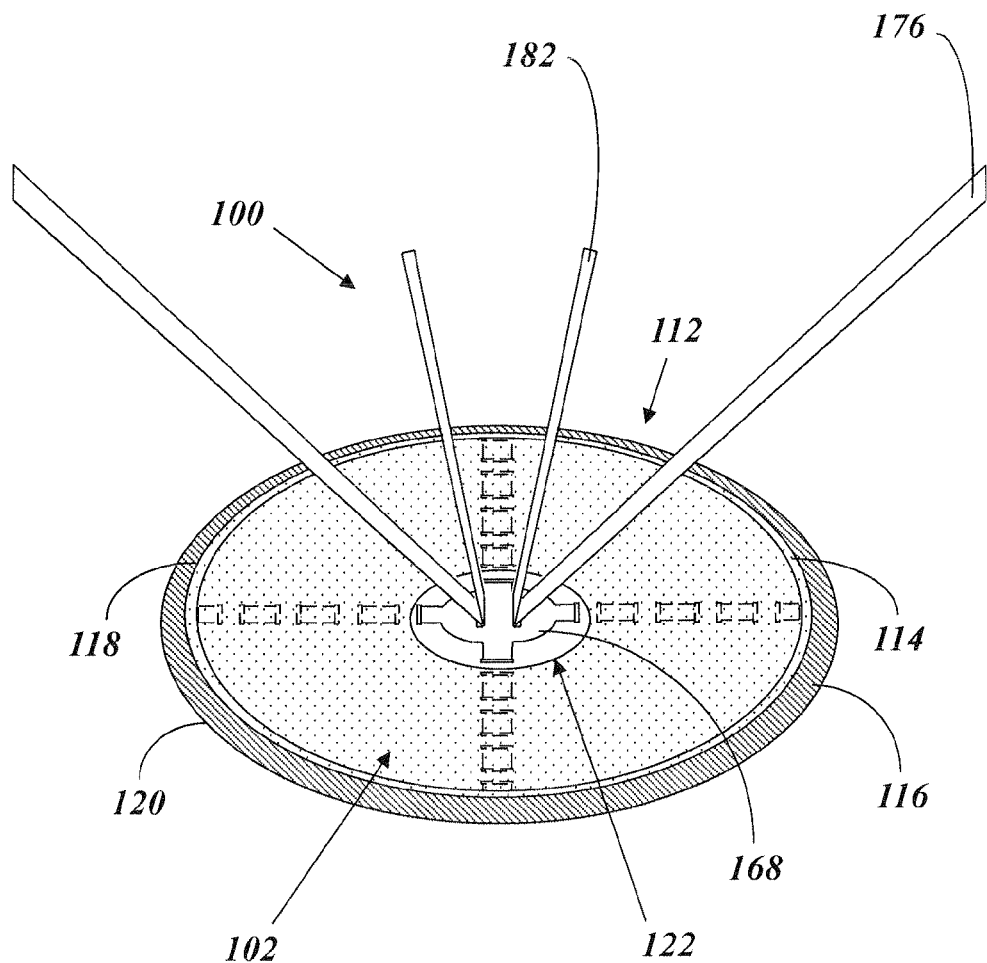
FIG. 20 depicts a perspective view of the deployment device of FIGS. 19A and 19B positioned within the prosthesis of FIGS. 2A through 2C.

FIG. 20 depicts a perspective view of the deployment device 100 of FIGS. 19A and 19B situated in the prosthesis 112 of FIGS. 2A through 2C. For purposes of clarity, the serpentine separation line 173 is not illustrated. In the embodiment of FIG. 20, as with previous illustrative embodiments of the present invention, the flexible support structure 102 of the deployment device 100 extends to a perimeter of the prosthesis 112, allowing the flexible support structure 102 to sit securely within the prosthesis 112 without any need for an attachment mechanism, such as adhesive or stitching. For example, as depicted in FIG. 20, the flexible support structure 102 can extend substantially to the outer perimeter 118 of the first layer 114 and/or the outer perimeter 120 of the second layer 116. In some embodiments, the flexible support structure 102 extends to and is in contact with a radially outermost surface 125 of the enclosure 124 when the flexible support structure 102 is in a deployed (e.g., generally planar) configuration, as depicted and described previously herein with reference to FIG. 2C. The deployment device 100 of FIG. 20 is removed from the prosthesis 112 in a stepwise fashion, first by pulling on the additional strap 182 to remove the removable connector piece 168, and then by pulling on the strap 176 (forming the tab 104) to remove the flexible support structure 102.

As can be seen from FIG. 20, the additional strap 182 is positioned within the strap 176. Thus, a surgeon is enabled to remove the removable connector piece 168 by pulling upward on the additional strap 182. The surgeon further is enabled to remove the flexible support structure 102 by pulling upward on the strap 176. In addition to allowing the surgeon to remove the flexible support structure 102, the strap 176 also can be used to assist the surgeon in positioning the prosthesis 112. For example, in the system depicted in FIG. 20, manipulating the strap 176 prior to release of the removable connector piece 168 from the flexible support structure 102 causes the flexible support structure 102 and the prosthesis 112 to move together. Thus, the strap 176 can provide additional handling assistance to the surgeon during use of the deployment device 100.

In some embodiments, the removable connector piece 168 is not included. For example, FIG. 21 depicts an additional embodiment of the deployment device 100 in which the flexible support structure 102 include a serpentine separation line 173. A "serpentine separation line" herein refers to an arrangement of one or more connected separation lines that extend from an inner (e.g., central) portion of the flexible support structure 102 to one or more points on the perimeter of the flexible support structure 102. The term "serpentine" can include straight lines, jagged lines, curved lines, and the like. As utilized herein, a "separation line" generally refers to any straight, curved, jagged, etc. pathway situated in one or more materials that is adapted to be torn (e.g., without separating abutting portions in the one or more materials that are away from the separation line). A separation line can extend across one material or multiple different materials and can extend across one or multiple types of objects. In illustrative embodiments, the serpentine separation line 173 travels some angular distance relative to its inner endpoint (e.g., does not follow a straight line). In further illustrative embodiments, the serpentine separation line 173 travels an angular distance of at least 360 degrees (e.g., by making at least one complete revolution). Furthermore, in illustrative embodiments, the serpentine separation line 173 is a spiral separation line. The serpentine separation line 173 can include and be implemented by a series of through-holes, a thin or weaker material, or any other type of separation line. One of skill in the art will appreciate yet other materials, implementations, shapes, and the like for the serpentine separation line 173. All such alternatives are contemplated within the scope of the present invention.

Figure 21A:
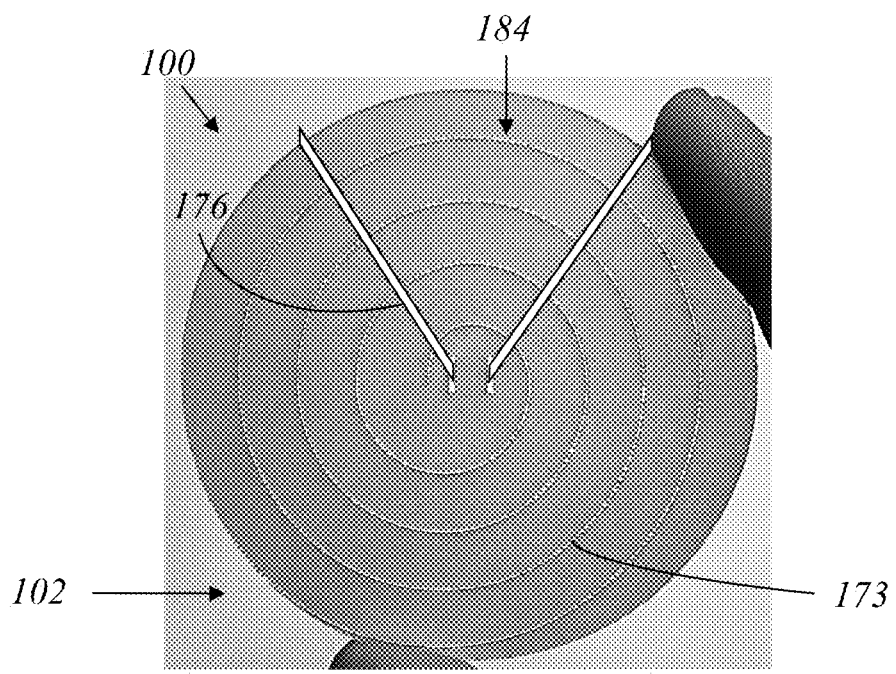
FIG. 21A depicts a perspective view of a deployment device having a serpentine separation line that includes a plurality of perforations, according to embodiments of the present invention.
Figure 21B:
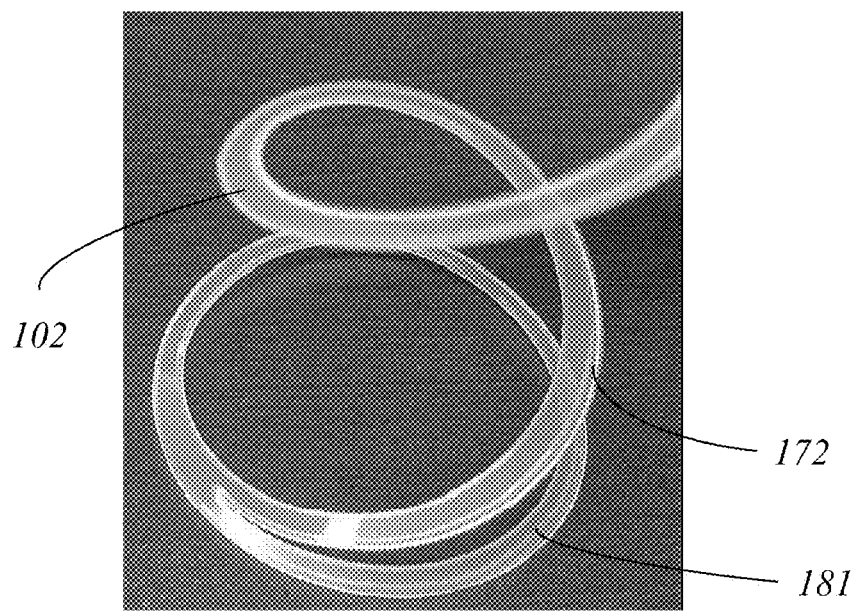
FIG. 21B depicts a perspective view of a deployment device having a serpentine separation line that has been separated to form a serpentine edge.
Figure 22:
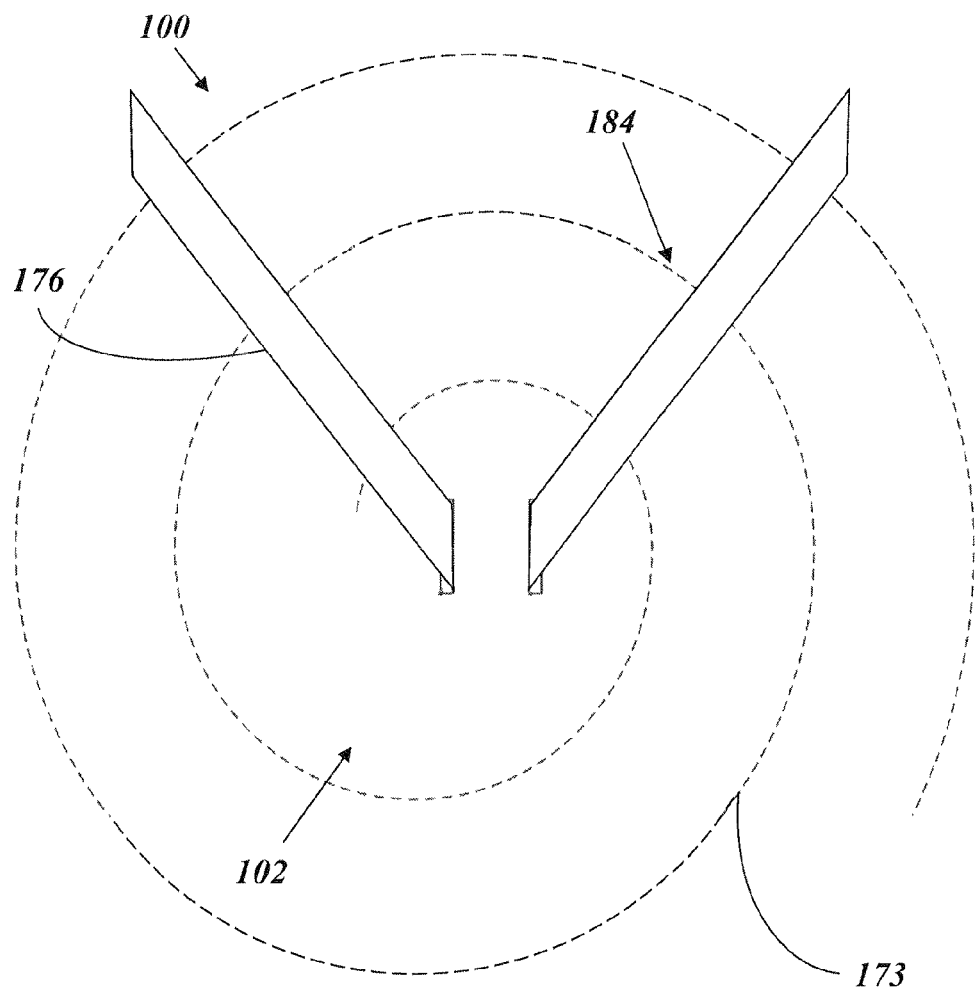
FIG. 22 depicts a close-up view of a central portion of the deployment device of FIG. 21, according to aspects of the present invention.

In the example embodiment of FIG. 21A, the serpentine separation line 173 is formed of a series of through-holes 184 extending through an entirety of the flexible support structure. Accordingly, upon separating the series of through-holes 184 along the serpentine separation line 173, portions of the flexible support structure 102 abutting along the serpentine separation line 173 are released and a serpentine edge 172 is formed (see FIG. 21B, see also FIG. 25B). FIG. 22 depicts a close-up view of the deployment device 100 at a central portion thereof. The series of through-holes 184 (represented by a dashed line) are sized and spaced to maintain some limited structural reinforcement between abutting portions along the serpentine separation line 173 and create a nearly-contiguous surface with minimal void space, but are also designed to create a separation path, e.g., in response to a user tugging or pulling up on the strap 176. For example, the serpentine separation line 173 can be constructed by forming a series of perforations in the flexible support structure 102 in a serpentine pattern. Accordingly, the series of through-holes 184 and the serpentine separation line 173 extend from a central portion of the flexible support structure 102 to a point on a perimeter of the flexible support structure 102. As with the serpentine edge 172 (which is formed by separating the serpentine separation line 173), the serpentine separation line 173 includes an inner end proximate to the center of the flexible support structure 102 and an outer end at a position on the perimeter of the flexible support structure 102.

Furthermore, the deployment device 100 can include a stress relief hole 186. The stress relief hole 186 is a through-hole disposed at the innermost end of the serpentine separation line 173 (e.g., the start point for forming a separation in the serpentine separation line 173), as depicted in the example embodiment of FIG. 23. In the example embodiment of FIG. 23, the stress relief hole 186 is generally circular and is situated near a center of the flexible support structure 102. Functionally, the stress relief hole 186 is a hole situated at the beginning of the serpentine separation line 173 to effectively distribute the stress in this region and thereby reduce the likelihood of propagation of unintended separations in the flexible support structure 102 at non-perforated positions away from the serpentine separation line 173 (e.g., as might be caused by a sharp pull on the strap 176). In this manner, the stress relief hole 186 can aid in initiating a separation in the serpentine separation line 173 based on a pulling force on the strap 176 serpentine. As a result, a sharp pull and subsequent steady pull force on the strap 176 causes the series of through-holes 184 to separation along the serpentine separation line 173. In this manner, the serpentine edge 172 is formed and abutting portions along the serpentine separation line 173 become unconnected to one another, enabling them to collapse (i.e., fold and deform) during removal of the deployment device 100 from the prosthesis 112 (e.g., the prosthesis of FIGS. 2A through 2C).

Figure 23:
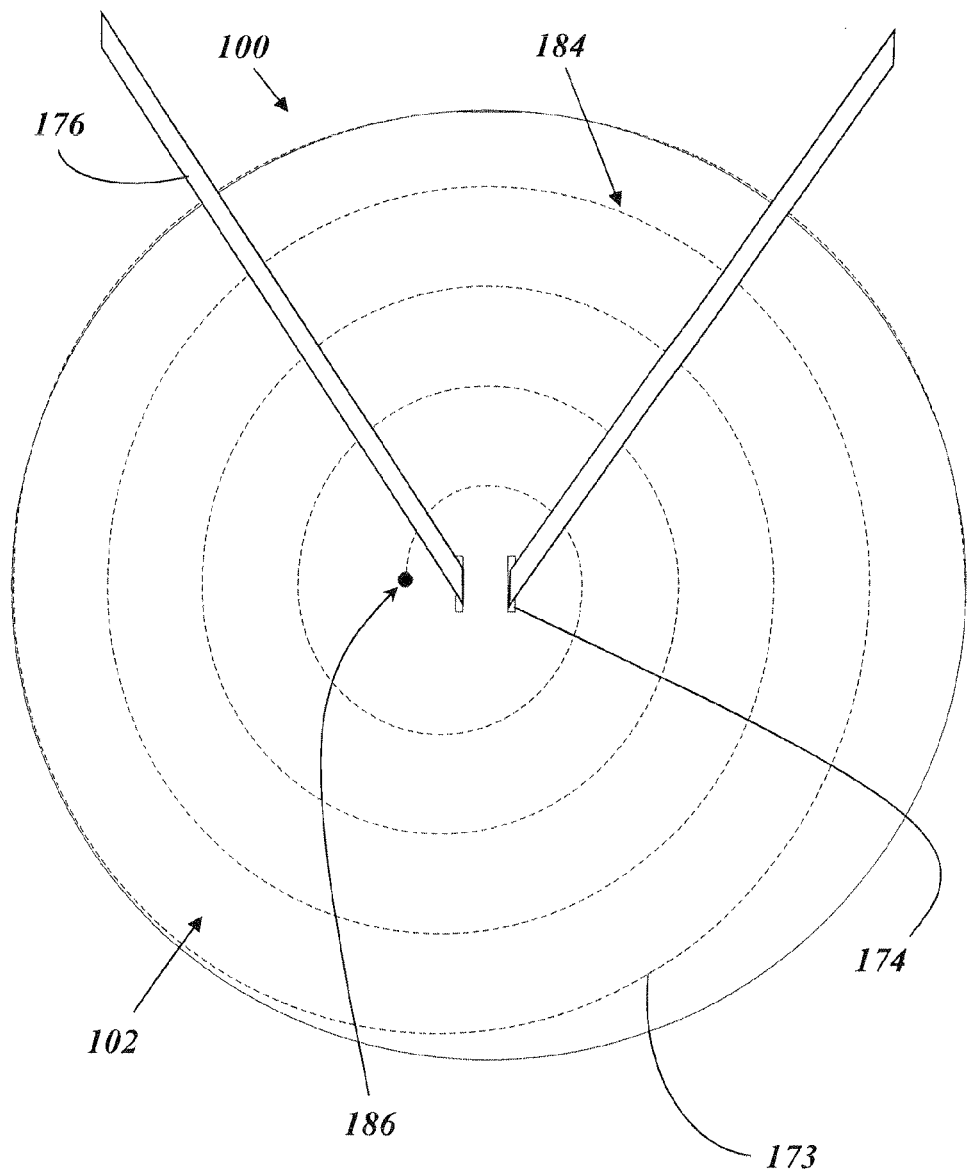
FIG. 23 depicts the deployment device of FIG. 21, further including a stress relief hole at an inner end of the serpentine separation line, according to embodiments of the present invention.

In the example embodiment of FIG. 23, the strap 176 used for separating along the series of through-holes 184 in the serpentine edge 172 can be a single continuous elongate member (e.g., formed of a single piece of material) that passes in one of the strap slots 174, beneath a central portion of the flexible support structure 102, and through another of the strap slots 174. As with all other straps provided herein, the strap 176 generally can be flexible or rigid (e.g., allowing it to be used as a positioning device or handling device during deployment and/or fixation).

Figure 24:
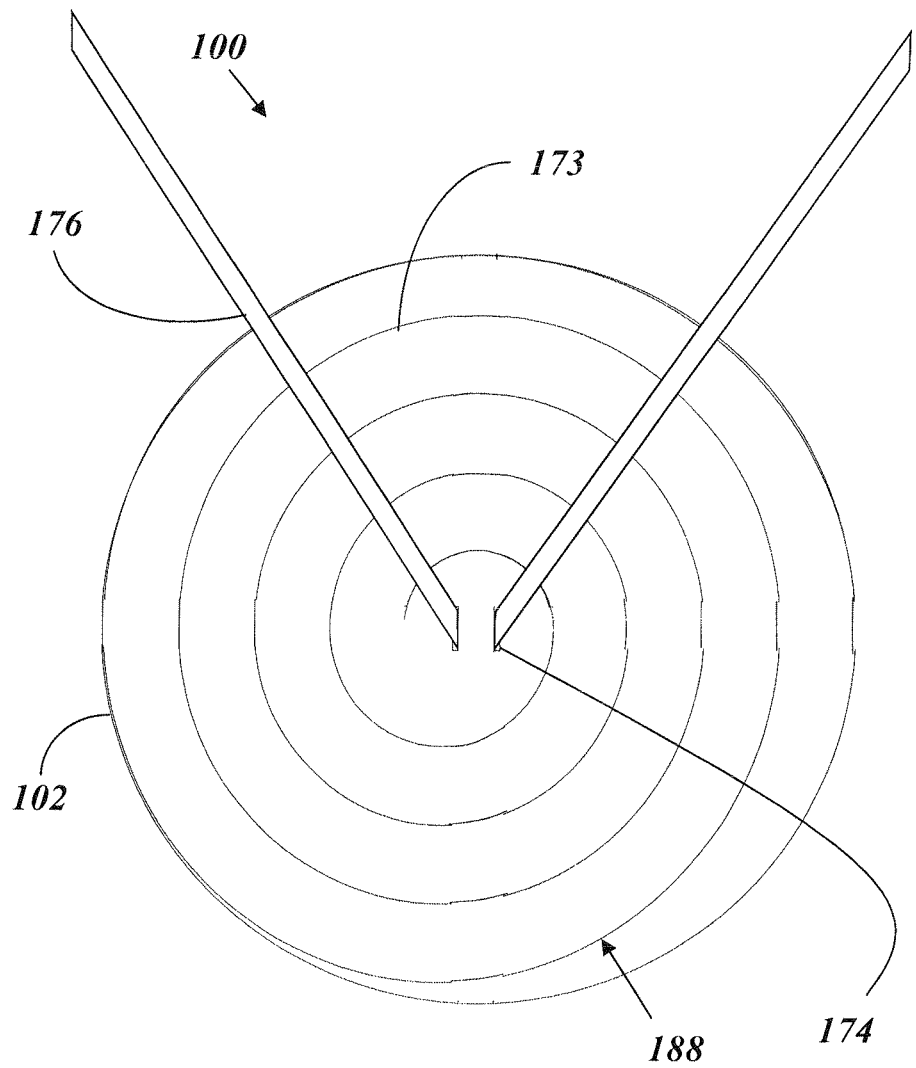
FIG. 24 depicts a perspective view of a deployment device having a serpentine separation line that includes a continuous strip of material, according to embodiments of the present invention.

Alternatively or additionally to providing the series of through-holes 184 between abutting portions of the flexible support structure 102 along the serpentine separation line 173, a relatively weaker (e.g., relatively thinner) strip of material can be disposed continuously in a serpentine along the flexible support structure 102 for forming the serpentine separation line 173. For example, FIG. 24 depicts one example embodiment of such a continuous strip 188 of material forming the serpentine separation line 173. The continuous strip 188 of material can be weaker (e.g., thinner) relative to a remainder of the flexible support structure 102. For example, the continuous strip 188 of material along the serpentine separation line 173 can be formed by directing a laser (e.g., at a particular power level) at the flexible support structure 102 and moving the laser in a serpentine path (or moving the flexible support structure 102 in a serpentine path relative to the laser), thereby thinning the material of the flexible support structure 102 at points contacted by the laser (a technique commonly referred to as "kiss cutting"). The depth of the cut can be selected to ensure easy separation mechanics along the serpentine separation line 173 as would be appreciated by one of skill in the art upon reading the present specification, e.g., based on material properties of the material being used (density, etc.), the size of the material (thickness, etc.), and the like. In addition, laser cuts can be implemented in such a way that is optimized to be thick enough to resist fracture during compression/folding of the flexible support structure 102, yet thin enough to enable easy separation/removal along the serpentine separation line 173. Alternatively to laser cutting, the continuous strip 188 of material can be formed by "kiss cutting" sheet stock with a steel rule die, as would be appreciated by one of skill in the art. Any other suitable methods of manufacturing the continuous strip 188 of material also may be used, such as micro-molding, injection molding, and other alternative manufacturing methods.

In some embodiments, the kiss cuts can be performed at varying thicknesses, such that some regions of the serpentine separation line 173 are more difficult to separation than other regions. For example, by using a more shallow kiss cut to form the serpentine separation line 173 at a central portion of the flexible support structure 102, the serpentine separation line 173 can be sufficiently strong and durable to withstand use of the straps 178 as rigid handles for intraoperative positioning and maneuvering of the prosthesis 112. Additionally, forming the serpentine separation line 173 of a deeper kiss cut at outer portions of the flexible support structure 102 allows the serpentine separation line 173 to be more easily torn during removal from the prosthesis 112. In addition, kiss cuts can be implemented in such a way that is optimized to be thick enough to resist fracture during compression/folding of the flexible support structure 102, yet thin enough to enable easy separation/removal along the serpentine separation line 173.

In the example embodiment of the deployment device 100 depicted in FIG. 24, the serpentine separation line 173 forms about four and a half revolutions. However, it should be understood that more or less revolutions can be included based on the intended medical applications and the particular implementation of the deployment device 100 (e.g., based on the size of the deployment device 100, the thickness of the flexible support structure 102, etc.). The particular number of revolutions formed by the serpentine separation line 173 can be selected to ensure that the flexible support structure 102 has a flexibility that is sufficient to allow the flexible support structure 102 to reconfigure and pass through the opening 122 in the prosthesis 112.

Figure 25A:
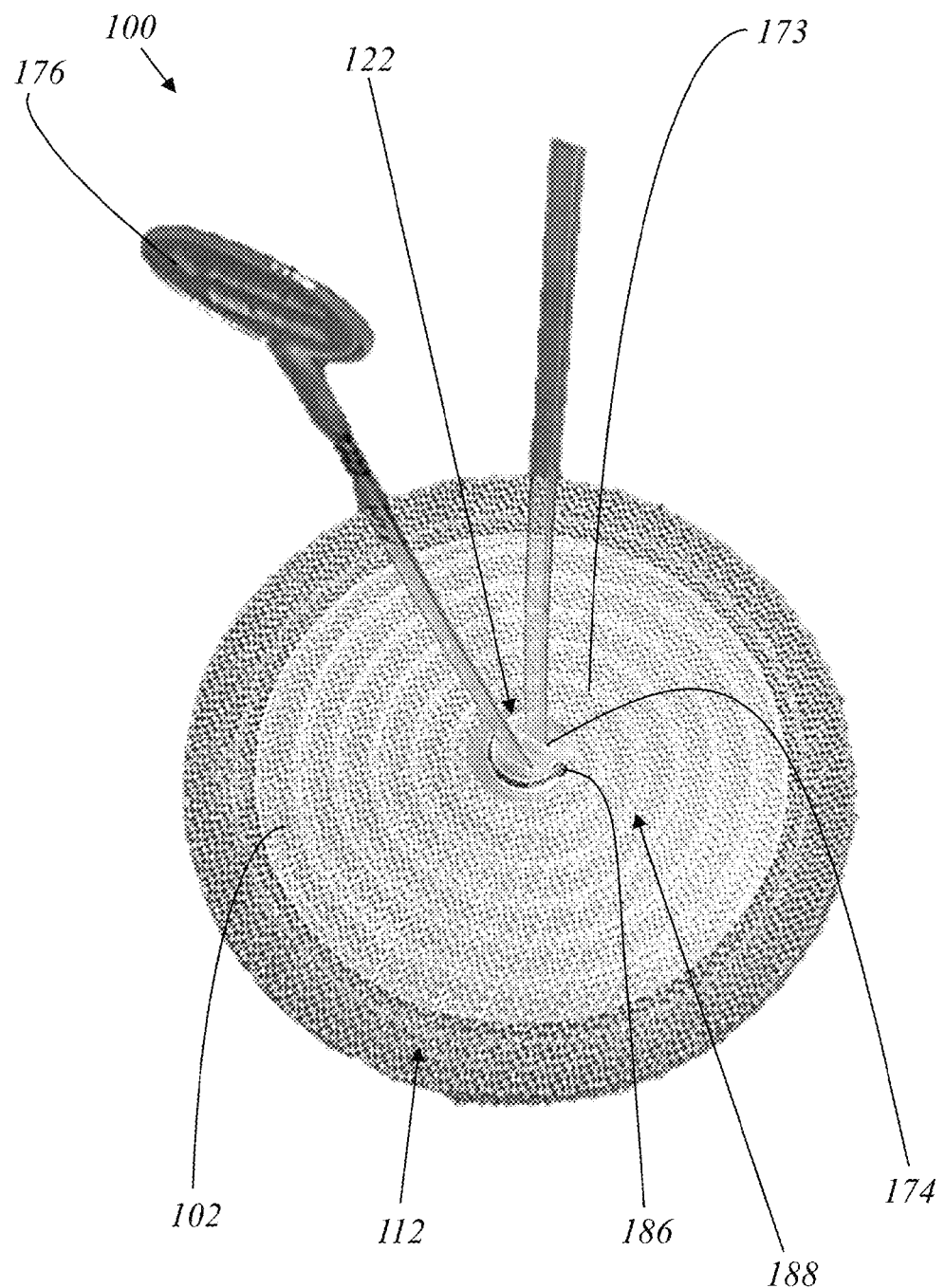
FIG. 25A depicts a perspective view of the deployment device of FIG. 24 situated within the prosthesis of FIGS. 2A through 2C.
Figure 25B:
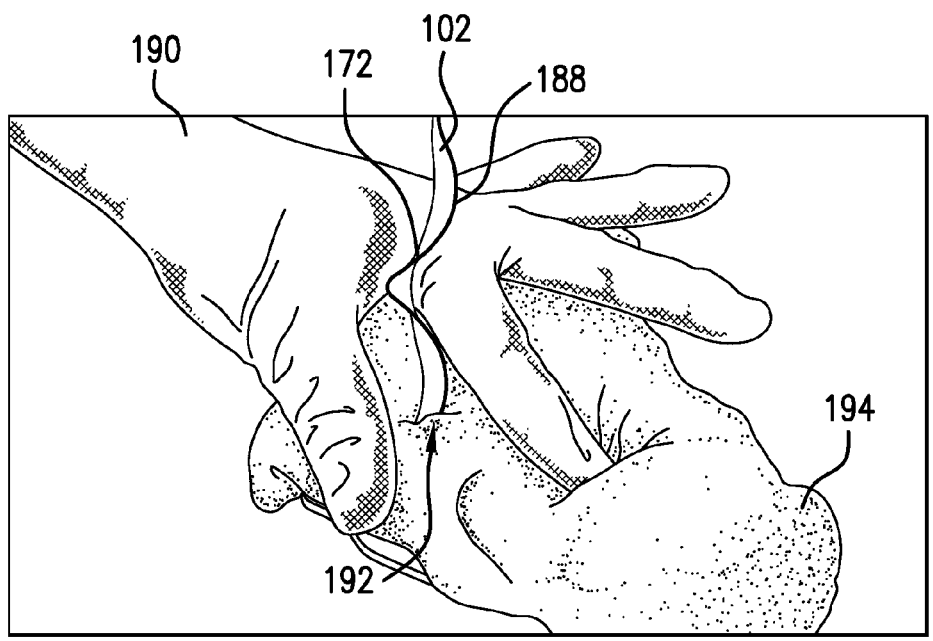
FIG. 25B depicts a perspective view of the deployment device of FIG. 25A assuming a helix (e.g., a conventional serpentine staircase) configuration during removal from a defect or opening in an artificial muscle wall, according to aspects of the present invention.

Furthermore, the invention is not limited to any particular value of density, thickness, etc. of the flexible support structure 102. For example, the flexible support structure 120 can be constructed of low density polyethylene, low density polypropylene, and the like. Rather, a wide variety of combinations of specific materials and structural properties (e.g., including number of revolutions of the serpentine separation line 173) can be selected to provide the flexible support structure 102 with a flexibility sufficient to reconfigure and pass through the opening 122 in the prosthesis 112. FIG. 25A depicts the deployment device 100 of FIG. 24 situated in the prosthesis 112 of FIGS. 2A through 2C. The deployment device 100 is removed by providing a sharp pull on the strap 176 to begin separating the continuous strip 188 of material at the stress relief hole 186, then by steadily pulling on the strap 176 in an upward direction away from the prosthesis 112 to progressively separate the remainder of the continuous strip 188 of material extending out from the stress relief hole 186. In this manner, abutting portions along the continuous strip 188 of material of the flexible support structure 102 become unconnected and are enabled to release upward so as to assume a reconfigured (e.g., bent, folded, buckled, overlapping, etc.) shape, e.g., resembling a helix or a conventional spiral staircase. The reconfigured shape allows the flexible support structure 102 to pass through the opening 122, which has a smaller total circumferential area than the total circumferential area of the flexible support structure 102 in the deployed (e.g., generally planar) state. For example, the flexible support structure 102 is depicted in a helix configuration in FIG. 25B. Specifically, FIG. 25B illustrates a perspective view of a surgeon 190 removing the flexible support structure 102 through a hole or defect 192 in an artificial muscle wall 194. The step shown in FIG. 25B occurs after implanting the prosthesis (not visible in FIG. 25B) through the hole or defect 192 and affixing it to the artificial muscle wall 194 (e.g., with tacks or sutures). The ability of the flexible support structure 102 to reconfigure into a helix affords the deployment device 100 great versatility. For example, this feature is particularly advantageous for the reason that it allows the deployment device 100 to reconfigure in a manner enabling extraction through nearly any size defect or orifice.

It should be noted that the continuous strip 188 that results from the flexible support structure 102 being reconfigured to enable removal of the structure can include the continuous strip 188 terminating in a loop or ring configuration. Specifically, referring back to FIG. 21B, the flexible support structure 102 is shown after having been reconfigured by separating the structure along the serpentine separation line, with a loop or ring 181. As shown and configured, the ring 181 is formed by the outer most perimeter of the original flexible support structure 102. As the flexible support structure is removed from the prosthesis, the ring 181 is maintained at the end of the elongate continuous strip 188 to signal to the surgeon that the entire flexible support structure 102 has been removed from the prosthesis (once the surgeon sees the ring 181 exiting from the prosthesis). Those of skill in the art will appreciate other ways to provide a signal or indication to the user of the last remaining portion of the flexible support structure 102 that is removed from the prosthesis, including the ring 181 or some other structure variation, or a color or label indicator, or other visual representation indicating the end of the device.

Figure 26A:
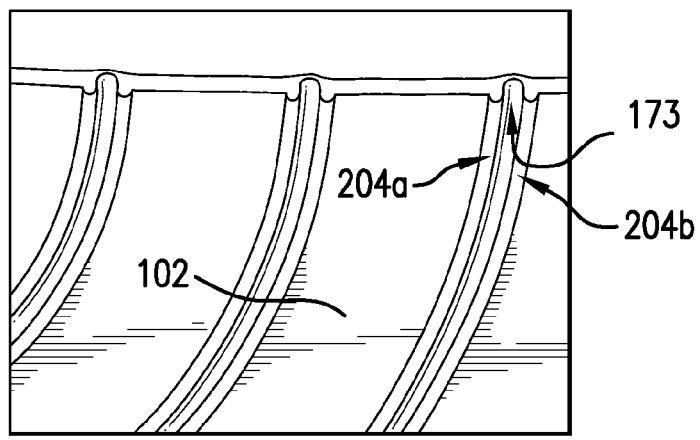
FIGS. 26A, 26B, and 26C depict a perspective view, a side view, and a close up view, respectively, of a cross section of reinforcing lips abutting the serpentine separation line, according to aspects of the present invention.
Figure 26B:
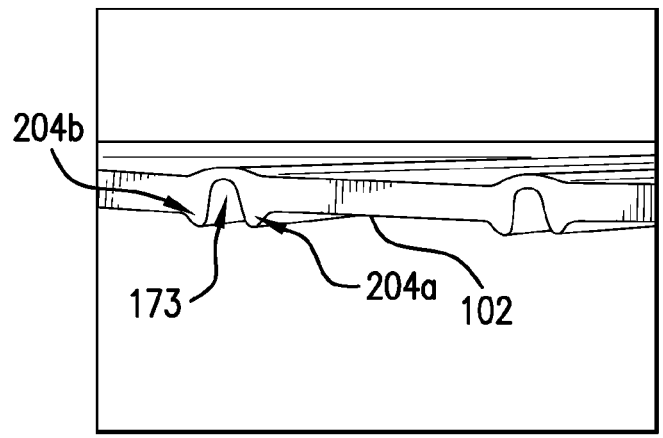
Figure 26C:
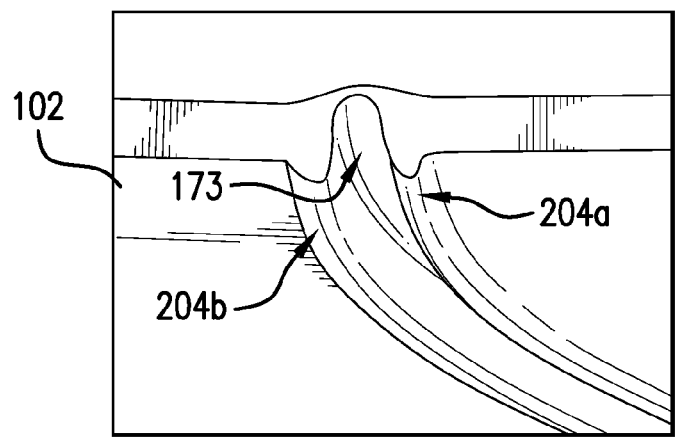

In some embodiments of the present invention, the flexible support structure 102 includes one or more reinforcing lips situated beside (e.g., adjacent to and/or contiguous with) the path of the serpentine separation line 173. For example, FIGS. 26A, 26B, and 26C depict a perspective view, a side view, and a close-up view, respectively, of a cross section of two such reinforcing lips 204a, 204b that can be formed in the flexible support structure 102. As depicted in FIGS. 26A through 26C, the flexible support structure 102 is depicted right-side up (upright and erect). In the example embodiments of FIGS. 26A through 26C, the reinforcing lips 204a, 204b are formed on both sides of the serpentine separation line 173. Each reinforcing lip 204a, 204b is contiguous with the serpentine separation line 173 at its respective side. The serpentine separation line 173 of the example embodiment of FIGS. 26A through 26C is defined by a thinner region in the material of the flexible support structure 102, e.g., formed as a depression in the flexible support structure 102. Each reinforcing lip 204a, 204b forms a slight elevation or wall on one side of the depression forming the serpentine separation line 173. The reinforcing lip 204a follows along the path of the separation line 173 on an inner side of the separation line 173. The reinforcing lip 204b follows along the path of the separation line 173 on an outer side of the separation line 173. In other embodiments, however, the reinforcing lips 204a, 204b are not included.

In one example embodiment, the flexible support structure 102 of FIGS. 26A through 26C is constructed from low-density polyethylene and has a thickness of about 0.020 inches, a density of about 0.92 g/cm$^3$, a melt flow index (MFI) of about 1.8 g/10 min, and an Elmendorf separation strength determined through various mechanical tests, e.g., of about 400 g in the machine direction (MD) and of about 280 g in the transverse direction (TD). One of skill in the art will appreciate that these dimensions and material properties are in no way limiting to the scope of the present invention. Rather, the dimensions and material properties provided herein are exemplary and described merely for purposes of illustration. Embodiments of the present invention can assume a wide variety of sizes, dimensions, shapes, material properties, and the like, as would be appreciated by one of skill in the art upon reading the present specification. The specific values can be selected based on the intended applications (e.g., the intended target site, the intended medical applications, etc.).

Figure 27A:
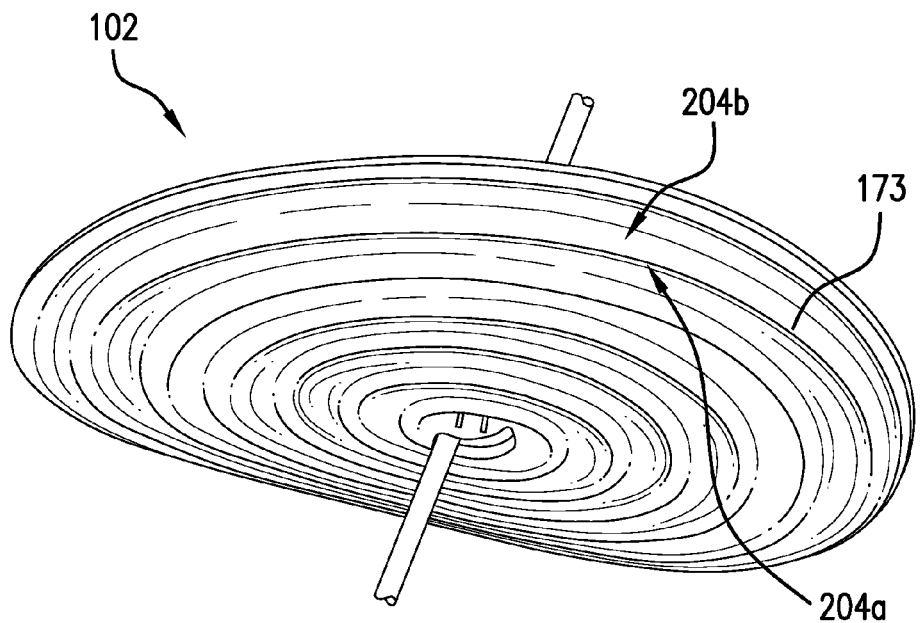
FIGS. 27A and 27B depict a perspective view and a bottom view, respectively, of the flexible support structure of FIGS. 26A through 26C, according to embodiments of the present invention.
Figure 27B:
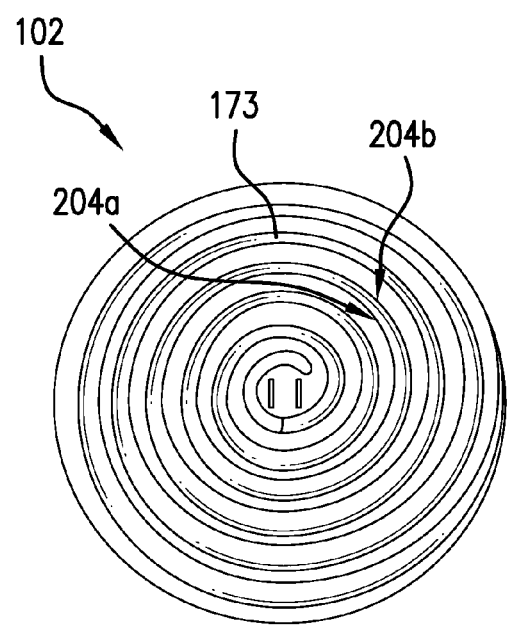

FIGS. 27A and 27B further depict the flexible support structure 102 of FIGS. 26A through 26C from a perspective view and a bottom view, respectively. As can be seen, the serpentine separation line 173 and the reinforcing lips 204a, 204b collectively form a serpentine path extending in revolutions from an inner position on the flexible support structure 102 to an outer position of the flexible support structure 102 (e.g., on a perimeter thereof).

Figure 28:
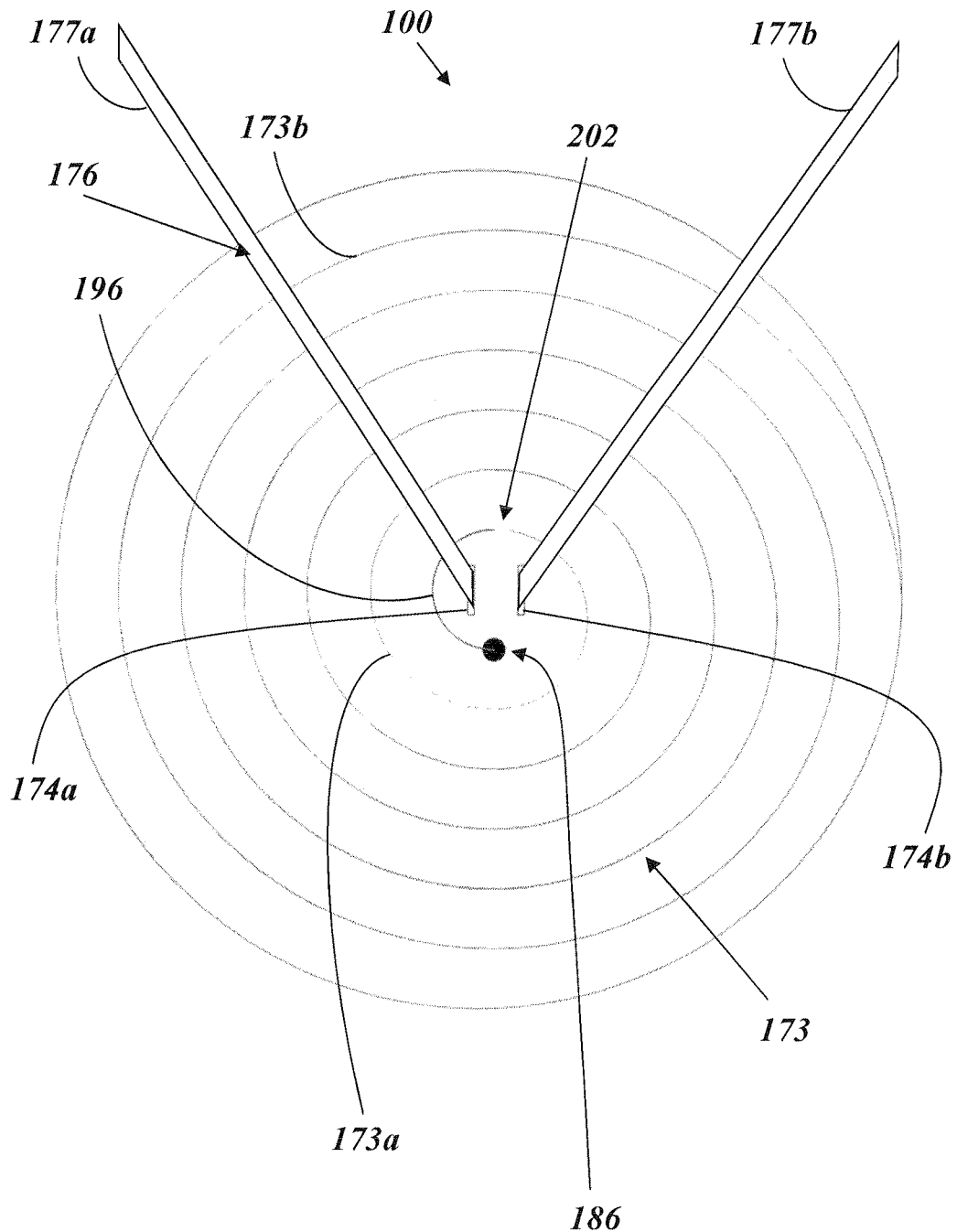
FIG. 28 depicts a perspective view of a deployment device having a serpentine separation line that includes two contiguous portions of unequal thicknesses, according to embodiments of the present invention.

As described previously herein, the serpentine separation line 173 can include multiple regions characterized by different thicknesses. For example, FIG. 28 depicts an additional embodiment of the deployment device 100 in which the serpentine line 173 includes an inner portion 173a (indicated in the figure by a green line) and an outer portion 173b (indicated in the figure by a red line). The inner portion 173a has a thickness that is greater than a thickness of the outer portion 173b, e.g., to promote easier separating/release along the outer portion 173b (e.g., when a surgeon truly intends to remove the deployment device 100), and more difficult separating/release along the inner portion 173a (e.g., to provide greater durability enabling a surgeon to manipulate the straps 176 as positioning/handling mechanisms). The inner portion of the serpentine separation line 173a and the outer portion of the serpentine separation line 173b can be continuous with one another, as depicted in the example embodiment of FIG. 28.

Furthermore, as depicted in FIG. 28, the serpentine separation line 173 can be preceded at its innermost end by a serpentine through-cut 196. The serpentine through-cut 196 can be a slit-like or slot-like opening situated in and extending entirely through the flexible support structure 102 (i.e., passing from a top surface of the flexible support structure 102 to a bottom surface of the flexible support structure 102). The serpentine through-cut 196 can follow a path that forms an extrapolation of the serpentine path followed by the serpentine separation line 173. Accordingly, including the through-cut 196 effectively forms a flap that, when pulled upward, initiates release of the serpentine separation line 173. At an innermost end, the serpentine through-cut 196 can terminate at the stress relief hole 186. At an outermost end, the serpentine through-cut 196 can terminate at a gap 202 of material on the flexible support structure 102 between the serpentine through-cut 196 and the innermost end of the serpentine separation line 173. For example, the gap 202 can have a thickness that is substantially equal to as the thickness of the majority of the flexible support structure 102 (e.g., can have a thickness equal to the thickness of portions situated between the revolutions of the serpentine separation line 173 with the reinforcing walls 204a, 204b).

In the example embodiment of FIG. 28, the strap slots 174a, 174b can be distinguished based on proximity to the serpentine through-cut 196. Accordingly, the ends 177a, 177b of the strap 176 similarly can be distinguished based on which strap slot 174a, 174b each passes through and extends from. In the example embodiment of FIG. 28, by providing the serpentine through-cut 196 in a position displaced from the center of the flexible support structure 102, the two strap ends 177a, 177b can be used for different functions by a surgeon during intraoperative handling and manipulation. The strap end 177a, being more proximate to the through-cut 196 and less proximate to the thicker inner portion 173a, will more effectively break the gap 202 of material and initiate release of the separation line 173 in response to a moderate tug or pull by the surgeon. Stated differently, tugging upward on the strap end 177a causes the semi-circular flap formed by the through-cut 196 to lift upward and eventually distribute enough tension on the gap 202 to separation the gap 202 and thereby initiate release of the spiral separation line 173. On the other hand, the strap end 177b, being less proximate to the through-cut 196 (i.e, more distal from the through-cut 196) and more proximate to the thicker inner portion 173a, will more effectively serve as a positioning tool which can better distribute tensile forces due to tugs and pulls without initiating release of the separation line 173.

Figure 29A:
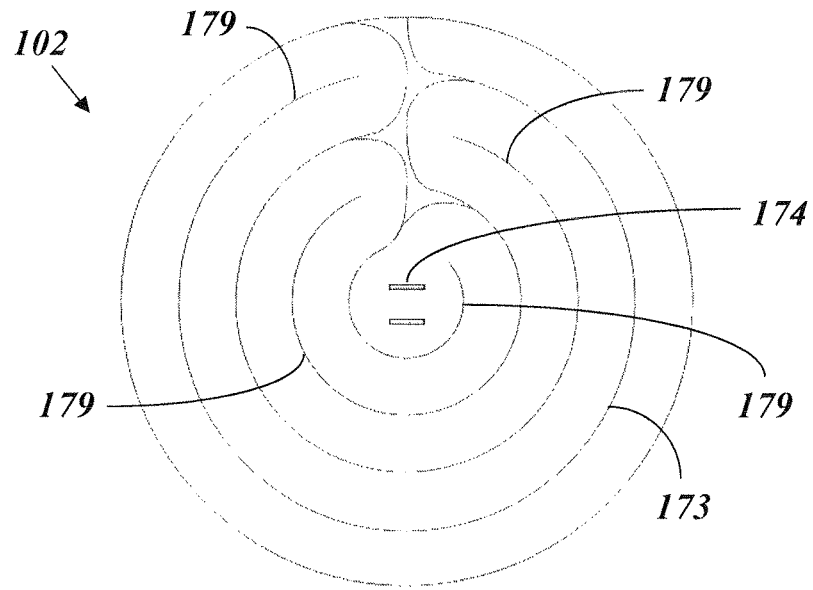
FIG. 29A depicts a top view of a flexible support structure having an alternative serpentine separation line with a plurality of branches, according to embodiments of the present invention.
Figure 29B:
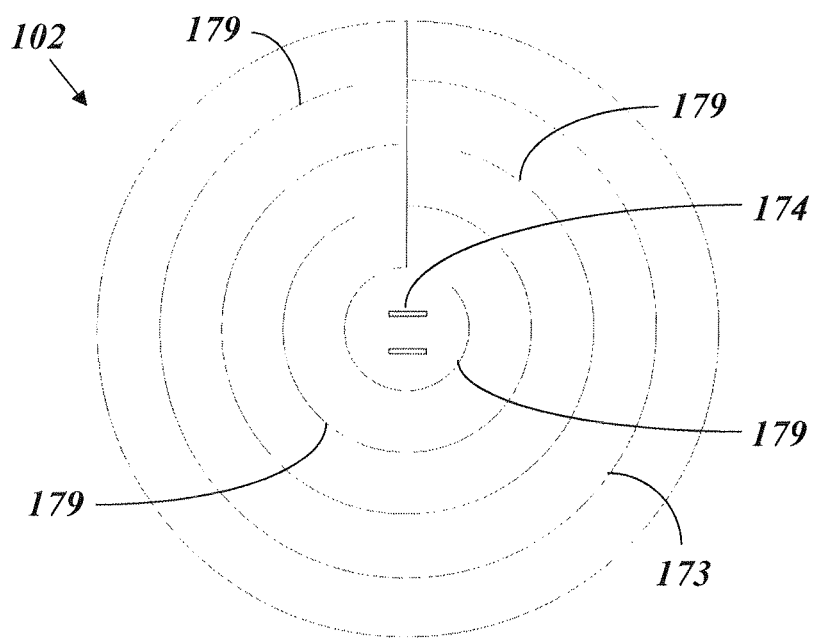
FIG. 29B depicts a top view of a flexible support structure having yet another alternative serpentine separation line with a plurality of branches, according to embodiments of the present invention.

It should be noted that the serpentine separation line 173 and the serpentine edge 172 can assume other types of serpentine shapes besides the exemplary smoothly curved serpentines and spirals depicted in the figures. For example, the serpentine separation line 173 and/or the serpentine edge 172 can be shaped as square serpentines/spirals, other shaped serpentines/spirals, or combinations thereof. As yet further examples, FIGS. 29A and 29B depict the flexible support structure 102 with alternative serpentine separation lines 173, according to embodiments of the present invention. As depicted in FIGS. 29A and 29B, the serpentine separation line 173 can include a plurality (e.g., two, three, four, five, etc.) of branches 179 that each terminates at one or more positions on the flexible support structure 102 and which are continuous with and connected to one another. As depicted in FIGS. 29A and 29B, the branches 179 of the serpentine separation line 173 can terminate at a position inward from the perimeter of the flexible support structure 102.

Figure 30:
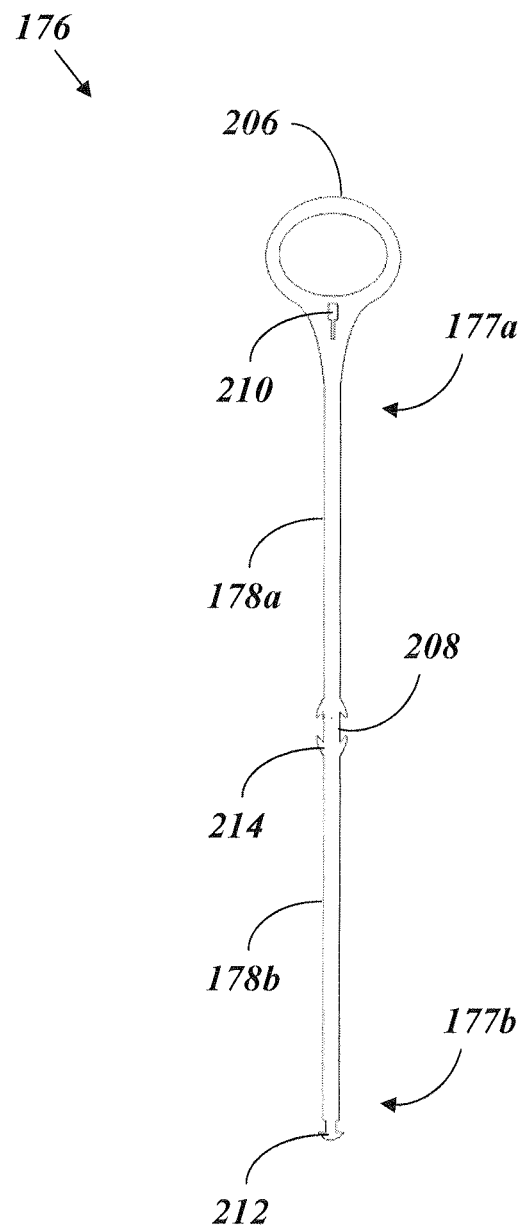
FIG. 30 depicts a strap in an unassembled (e.g., substantially flat) configuration that is adapted to serve as both a positioning device and deployment device removal tool, according to an example embodiment of the present invention.

FIG. 30 depicts the strap 176 according a further example embodiment of the present invention. As described previously, in such embodiments where the strap 176 is included, the strap 176 can form the tab 104. A medial portion 208 is slightly displaced from the center of the strap 176. The medial portion 208 thus divides the strap 176 into a longer appendage 178a and a shorter appendage 178b (relative to one another). As depicted in FIG. 30, the strap 176 is depicted in an unassembled form, such that the appendages 178a, 178b are aligned along the same plane. To assemble the strap 176, the appendages 178a, 178b are bent at the outer edges of the medial portion 208, such that the appendages 178a, 178b are erect and upright. A finger support ring 206 is adapted to receive the finger of a user and is situated at the end 177a of the longer appendage 178a. The base portion 180 is not included in the strap 176 of the example embodiment of FIG. 30. Each appendage 178a, 178b includes one or more barb mechanisms 214 extending therefrom that, once slid through the strap slots 174, act as mechanical stops that prevent the appendages 178a, 178b from sliding through the strap slots 174 in either direction. A slit 210 is situated in and through the end 177a of the longer appendage 178a, slightly inward of the finger support ring 206. The slit 210 is sized, shaped, and dimensioned to receive a protuberance 212 formed on the end 177b of the shorter appendage 178b. The protuberance 212 is sized, shaped, and dimensioned to pass through the slit 210 and subsequently lock in place by turning. The protuberance 212 is released by turning in the opposite direction to unlock. In illustrative embodiments, the strap 176 is formed of polypropylene, PETG (polyethylene terephthalate glycol-modified), or any other suitable (e.g., medical-grade) material. One of skill in the art will appreciate a variety of other materials herein that can be used to form the strap 176. All such alternatives and modifications are contemplated within the scope of the present invention.

Figure 31A:
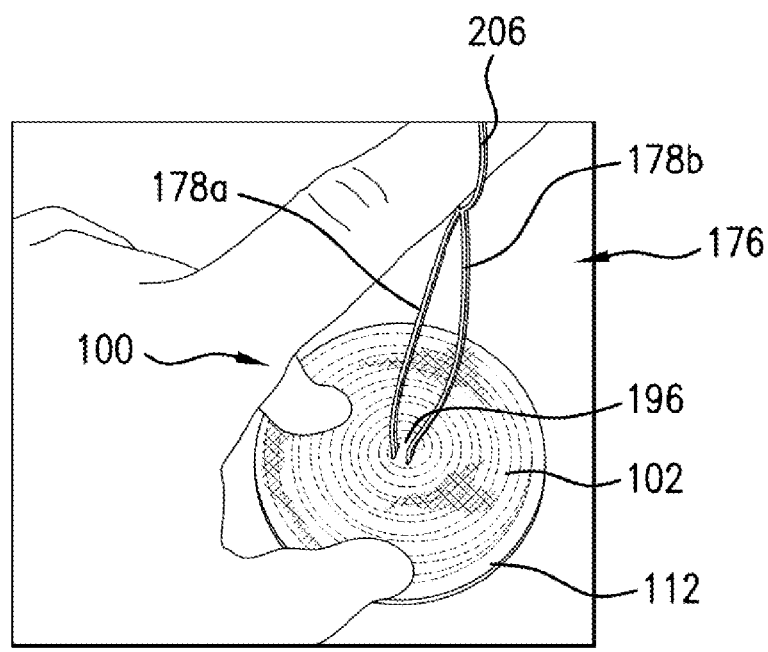
FIG. 31A depicts the strap of FIG. 30 in a deployment device situated in a prosthesis, and in a locked position forming a positioning tool, according to aspects of the present invention.

FIG. 31A depicts the strap 176 of FIG. 30 coupled to the flexible support structure 102 of the deployment device 100 depicted in FIG. 28. The deployment device 100 is situated within the prosthesis 112 of FIGS. 2A through 2C. The longer appendage 178a is adapted to be affixed to the flexible support structure 102 on the semi-circular flap formed by the serpentine through-cut 196. The shorter appendage 178b is adapted to be affixed at a location not on the semi-circular flap formed by the serpentine through-cut 196. The medial portion 208 of the strap 176 is situated on top of the flexible support structure 102, such that the barb mechanisms 214 pass down through the strap slots 174 to fixedly latch onto the flexible support structure 102. As shown in FIG. 31A, the strap 176 is in a locked configuration. When in the locked configuration of FIG. 31A, the strap 176 forms and serves as a positioning tool, as described previously herein with reference to FIG. 28. Specifically, due to the differences in length, the shorter appendage 178b is taught, whereas the longer appendage 178a is bent and includes some slack. Thus, forces on the finger support ring 206 are distributed along the shorter appendage 178b when the strap 176 is in the locked configuration. Given that the appendage 178b is not affixed on the semi-circular flap formed by the serpentine through-cut 196, forces on the finger support ring 206 are distributed more evenly across flexible support structure 102 in a manner that tends to avoid initiating release of the serpentine separation line 173 when the strap 176 is in the locked configuration.

Figure 31B:
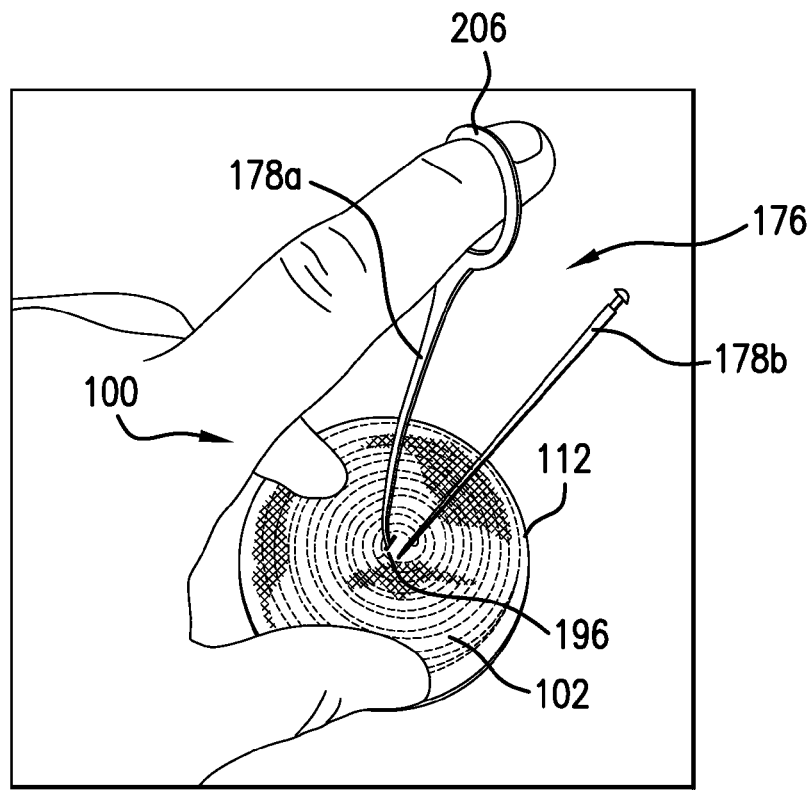
FIG. 31B depicts the strap of FIG. 31A in an unlocked position forming a deployment device removal tool, according to aspects of the present invention.

FIG. 31B depicts the strap 176 in an unlocked configuration. In the unlocked configuration, forces on the finger support ring 206 are distributed along the longer appendage 178a. Thus, the resulting tensile forces on the flexible support structure 102 are distributed on the semi-circular flap formed by the serpentine through-cut 196. This focusing of tensile forces on the semi-circular flap formed by the serpentine through-cut 196 enables the semi-circular flap to be lifted in such a way as to separation the gap 202 and initiate separation of the serpentine separation line 173. Accordingly, when the strap 176 is in a locked configuration, the strap 176 effectively serves as a positioning device, whereas when the strap 176 is in an unlocked configuration, the strap 176 effectively serves as the tab 104 for removing the deployment device 100 from the prosthesis 112.

Deployment devices 100 according to embodiments of the present invention can significantly improve prosthesis deployment for surgeons by easing the process of positioning a prosthesis during and after implantation. Moreover, deployment devices 100 according to embodiments of the present invention can eliminate the requirement for stitches or other fixation apparatuses used to secure a wire frame to a prosthesis. This can significantly reduce surgical time and operating room time, while providing a significantly easier mechanism for removing the deployment device 100. Rather than cutting or removing stitches at the periphery of a prosthesis, the deployment device 100 can be easily and immediately removed simply by pulling the tab 104 (e.g., straps, protruding segments, and any other tab described herein). As such, embodiments of the present invention eliminate risk of harm to a patient caused by cutting devices, etc.

Furthermore, deployment devices 100 utilizing a flexible support structure 102 forming a solid sheet or relatively solid sheet of material provide additional protection to a patient while a surgeon is affixing the prosthesis with tacks or sutures. The solid sheet layer prevents suture needles or tacks from being improperly placed therein, which helps a surgeon avoid accidental punctures to organs. For example, misplacing suture needles or tacks at an undesirable peripheral position on the prosthesis could result in a surgeon unintentionally piercing an organ below the prosthesis 112 that is hidden from view. Certain embodiments of the present invention overcome such risks by providing a deployment device 100 that is to be removed and thus is not to be affixed to surrounding tissue, etc.

Embodiments as depicted in FIGS. 24 through 31B that include a serpentine separation line 173 (e.g., formed of a continuous strip 188 of material) may be particularly beneficial for certain medical application. For example, embodiments having a continuous strip 188 of material create a surface for fixation guidance that can be wholly and entirely void of any openings or gaps, thereby presenting a surface for fixation guidance that is smooth and continuous prior to separating along the serpentine separation line 173. Furthermore, such continuous strips 188 of material create less risk of material being dispelled from the deployment device 100 during or after separating along the separation line 173. In addition, unlike the series of through-holes 184, separating the continuous strips 188 of material does not result in sharp or jagged edges being formed that could potentially create scrapes or scratches during removal, which may be beneficial in certain applications.

In providing a deployment device that is removable, embodiments of the present invention achieve a deployment device 100 that can greatly reduce dangerous post-operative complications and failures of a prosthesis caused by permanent rings or frame members currently used in prior art devices. In embodiments of the present invention, the full and complete removal of the deployment device 100 allows the prosthesis to be placed in the body without any additional rings or frame members permanently remaining therein. This creates a smooth surface in the prosthesis, which eliminates undesired surface tensions in the prosthesis that can cause failure and patient discomfort. By having less foreign material remain in the body, immunological complications can be minimized as well.

Furthermore, the deployment device 100 also functions as a barrier to prevent undesirable contact between the lower layer of mesh or underlying visceral tissue (e.g., bowel, etc.) and fixation elements (e.g., suture needles, tacks, etc.). The absence of voids across the smooth contiguous surface of the deployment device 100, which in illustrative embodiments spans across the entire interior of the prosthesis 112, can offer a solution to the potential problem of inadvertent surgical contact with surrounding tissue during the surgical procedure.

Notably, deployment devices 100 according to embodiments of the present invention achieve greater cost-effectiveness than existing prosthesis deployment devices, such as hernia patch deployment devices. For example, various component parts (e.g., including the flexible support structure 102) can be manufactured by cutting from a flat sheet of material. Accordingly, embodiments of the present invention enable greater manufacturing simplicity, thereby achieving improved cost savings. One of skill in the art will appreciate yet additional benefits not specifically mentioned herein upon reading the present specification.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A deployment device, comprising:
a flexible support structure configured in generally planar form having a first total circumferential area in a deployed configuration, and configured to independently apply a radial deployment force to achieve the deployed configuration;
a separation line in the flexible support structure extending in a generally serpentine shape from a central portion of the flexible support structure to a perimeter of the flexible support structure;
a through-cut disposed at an innermost end of the separation line at the central portion of the flexible support structure;
a first strap coupled with the flexible support structure in the central portion and proximal the through-cut;
a second strap coupled with the flexible support structure in the central portion and more distal from the through-cut than the first strap;
wherein a first pulling force applied to the first strap initiates separation along the separation line beginning at the through-cut;
wherein the first strap and the second strap are adapted to lock together at locations distal from the flexible support structure, and when in a locked configuration form a positioning tool for positioning the deployment device, and when in an unlocked configuration form a removal tool that enables the first pulling force applied to the first strap to initiate the separation along the separation line beginning at the through-cut; and
wherein the second strap is configured and positioned in such a way that the first pulling force applied to the second strap does not initiate separation along the separation line beginning at the through-cut, thereby enabling the second strap to at least partially form the positioning tool.

2. The deployment device of claim 1, wherein the flexible support structure is configured to be removed through an opening in a prosthesis having a second total circumferential area that is less than the first total circumferential area occupied by the flexible support structure when in the deployed configuration.

3. The deployment device of claim 1, wherein the separation line comprises a plurality of through-holes.

4. The deployment device of claim 1, wherein the separation line comprises a continuous strip of material.

5. The deployment device of claim 1, wherein the first strap and the second strap are coupled together at ends proximal the flexible support structure.

6. The deployment device of claim 1, wherein the first strap and the second strap are a continuous elongate strap.

7. The deployment device of claim 1, wherein the first total circumferential area of the flexible support structure configured in generally planar form in the deployed configuration is sized and dimensioned to fit within and completely expand and deploy a prosthesis into which the device is positioned, the prosthesis comprising a top layer and a bottom layer coupled together and forming an enclosure therebetween into which the device is configured for placement.

8. The deployment device of claim 1, wherein separation along the separation line terminates at a ring configuration formed by an outer perimeter of the flexible support structure.

9. A system, comprising:
a deployment device according to claim 1;
a prosthesis comprising a top layer and a bottom layer coupled together and forming an enclosure therebetween, the top layer having an aperture opening to the enclosure, wherein a second circumferential area of the aperture is less than the first total circumferential area of the deployment device and of a third circumferential area of the top layer in which the aperture is disposed; and
wherein the deployment device is removably disposed within the enclosure and configured to apply the radial deployment force on the prosthesis when positioned within the enclosure of the prosthesis; and
wherein if a suitable pulling force is applied to the first strap, separation occurs along the separation line such that the flexible support structure reconfigures from the generally planar form to an elongate continuous strip and continued pulling force causes the elongate continuous strip to pass through the aperture in such a way that the flexible support structure is ultimately removed from the prosthesis.

10. The system of claim 9, wherein the flexible support structure has an elasticity that generates a force sufficient to cause the prosthesis to assume a deployed configuration from a non-deployed configuration.

11. The system of claim 9, wherein the first total circumferential area of the flexible support structure configured in generally planar form in the deployed configuration is sized and dimensioned in such a way that the flexible support structure fits within and completely expands and deploys the prosthesis.

12. The deployment device of claim 1, further comprising a through-cut disposed at an innermost end of the separation line at the central portion of the flexible support structure.

13. The deployment device of claim 12, wherein the second strap is disposed more distal from the through-cut than the first strap.

14. The deployment device of claim 1, wherein portions of the flexible support structure along the separation line are coupled together prior to removal and are configured to separate for removal of the deployment device from the prosthesis.

15. The deployment device of claim 1, wherein the separation line comprises a plurality of through-holes or a continuous strip of material.

16. The deployment device of claim 1, further comprising a stress relief hole or opening situated in and through the flexible support structure proximate to an inner end of the separation line.

17. The deployment device of claim 1, wherein separation along the separation line terminates at a ring configuration formed by an outer perimeter of the flexible support structure.

18. The deployment device of claim 1, wherein the first strap is longer than the second strap such that when the first and second straps are in the locked configuration, the first strap becomes at least partially bent, and forces exerted on the first strap are thereby at least partially distributed along the second strap when in the locked configuration.

19. A deployment device, comprising:
a flexible support structure configured in generally planar form when in a deployed configuration;
a separation line in the flexible support structure extending in a generally serpentine shape;
a first strap coupled with the flexible support structure at a first location; and
a second strap coupled with the flexible support structure at a second location;

wherein the first and second locations are positioned such that there exists a separation force exertable on the flexible support structure that will initiate separation along the separation line when exerted at the first location, but will not initiate separation when exerted at the second location.

20. The deployment device of claim 19 further comprising a through-cut formed in the flexible support structure, wherein the first location is positioned relatively more proximal than the second location to the through-cut.

21. The deployment device of claim 19, wherein the first strap and the second strap are configured to selectively engage between an unlocked configuration in which the first strap exerts pulling forces on the flexible support structure at the first location, and a locked configuration in which the first strap exerts pulling forces at the second location via locked engagement with the second strap, such that separation is initiated along the separation line in response to the separation force applied to the first strap when the first and second straps are in the unlocked configuration, but separation along the separation line is resisted when the separation force is applied to the first strap when the first and second straps are in the locked configuration.

22. The deployment device of claim 21, further comprising a protuberance and a slit that are selectively engagable together to enable the first and second straps to transition between the locked configuration and the unlocked configuration.

23. A deployment device, comprising:
a flexible support structure having a separation line extending therealong;
a first strap coupled with the flexible support structure at a first location and configured to transfer forces exerted on the first strap to the flexible support structure at the first location; and
a second strap coupled with the flexible support structure at a second location and configured to transfer forces exerted on the second strap to the flexible support structure at the second location;
wherein the first and second straps are configured to lock together at locations distal from the flexible support structure such that a separation force exerted on the flexible support structure will initiate separation along the separation line when exerted by the first strap on the flexible support structure when the first and second straps are in an unlocked configuration but will not initiate separation along the separation line when exerted by the first and second straps on the flexible support structure when the first and second straps are in a locked configuration.

* * * * *